US010843990B2

(12) United States Patent
Haase et al.

(10) Patent No.: US 10,843,990 B2
(45) Date of Patent: Nov. 24, 2020

(54) PROCESSES FOR PREPARING CALIX[4]ARENES FROM CALIX[8]ARENES

(71) Applicant: SI GROUP, INC., Schenectady, NY (US)

(72) Inventors: Cornelius Haase, Schenectady, NY (US); Jeff Hiscock, Schenectady, NY (US); Philip David Atwood, Schenectady, NY (US)

(73) Assignee: SI GROUP, INC., Schenectady, NY (US)

( * ) Notice: Subject to any disclaimer, the term of this patent is extended or adjusted under 35 U.S.C. 154(b) by 0 days.

(21) Appl. No.: 16/271,554

(22) Filed: Feb. 8, 2019

(65) Prior Publication Data
US 2019/0248722 A1   Aug. 15, 2019

Related U.S. Application Data

(60) Provisional application No. 62/691,998, filed on Jun. 29, 2018, provisional application No. 62/628,472, filed on Feb. 9, 2018.

(51) Int. Cl.
| C07C 37/20 | (2006.01) |
| C07C 39/17 | (2006.01) |
| C07C 37/52 | (2006.01) |
| B01D 9/00 | (2006.01) |
| B01J 23/04 | (2006.01) |

(52) U.S. Cl.
CPC .............. *C07C 37/52* (2013.01); *C07C 37/20* (2013.01); *B01D 9/0054* (2013.01); *B01J 23/04* (2013.01); *C07C 39/17* (2013.01); *C07C 2603/92* (2017.05)

(58) Field of Classification Search
CPC ............ C07C 37/20; C07C 3/52; C07C 39/17
See application file for complete search history.

(56) References Cited

U.S. PATENT DOCUMENTS

| 2,868,844 | A | 1/1959 | Coffield et al. |
| 3,870,669 | A | 3/1975 | Hofel et al. |
| 5,378,791 | A | 1/1995 | Lancaster et al. |
| 5,952,526 | A | 9/1999 | Lamartine et al. |
| 6,200,936 | B1 | 3/2001 | Moreton |
| 6,271,337 | B1 | 8/2001 | Lamartine et al. |
| 6,984,599 | B2 | 1/2006 | Nagy |
| 7,524,469 | B2 | 4/2009 | Meikrantz et al. |
| 9,695,209 | B2 | 7/2017 | Dauvergne |
| 10,466,590 | B2 | 11/2019 | Imada |
| 2012/0145542 | A1 | 6/2012 | Nakamura et al. |
| 2015/0232603 | A1 | 8/2015 | Huc et al. |
| 2016/0108231 | A1 | 4/2016 | Aube et al. |
| 2017/0051224 | A1 | 2/2017 | Notari et al. |
| 2019/0100685 | A1 | 4/2019 | Cable |

FOREIGN PATENT DOCUMENTS

| EP | 0447977 A1 | 9/1991 |
| EP | 0480658 A2 | 4/1992 |
| EP | 2599814 A1 | 6/2013 |
| WO | 2017/025900 A1 | 2/2017 |
| WO | 2017/087115 A1 | 5/2017 |

OTHER PUBLICATIONS

Blanc, Alexandre, C. et al., "The preparation and use of novel immobilised guanidine catalysts in base-catalysed epoxidation and condensation reactions," Green Chemistry, Royal Society of Chemistry, GB, Nov. 1, 2000, pp. 238-288.
Dhawan, Balram , et al., "Calixarenes, 19a) Studies of the formation of calixarenes via condensation of p-alkylphenols and formaldehyde", Die Makomolekulare Chemie, vol. 188, Jan. 1, 1987, pp. 921-950.
Gutsche, C. David, et al., "Calixarenes. 4. The Synthesis, Characterization, and Properties of the Calixarenes from p-tert-Butylphenol," Journal of the American Chemical Society, Jul. 1, 1981, pp. 3782-3792.
Munch et al., "p-tert-Butylcalix[8]arene," Organic Syntheses, CV 8, 80 68: 243 (1990).
Gutsche et al., "Pathways for the Reversion of p-tert-Butylcalix[8]arene to p-tert-Butylcalix[4]arene," J. Org. Chem. 64: 3747-3750 (1999).
Burlini, "Synthesis of New Calixarene-Based Lubricant Additives," Doctoral Dissertation for Universita' Degli Studi di Parma, Dottorato di ricerca in Scienza e Tecnologia dei Materiali Innovativi, ciclo XXVIII (2016).
Stewart et al., "Isolation, Characterization, and Conformational Characteristics of p-tert-Butylcalix[9-20]arenes," J. Am. Chem. Soc. 121:4136-4146 (1999).
Dhawan et al., "Calixarenes. 10. Oxacalixarenes," J. Org. Chem. 48: 1536-1539 (1983).
Vocanson et al., "Characterization of synthetic precursors of p-tert-butycalix[4]arene and p-tert-butylcalix[8]arene. Mechanisms of formation of calix[4]arene and calix[8]arene", Supramolecular Chemistry 7:19-25 (1996).
Vocanson et al., "Characterization of precursors of p-tert-butycalix[6]arene synthesis. Mechanism of formation of p-tert-butylcalix[6]arene," Supramolecular Chemistry 4: 153-157 (1994).
Gutsche, "Calixarenes: An Introduction, 2nd Edition," RSC Publishing, pp. 30-31 and 236-237 (2008).
Neri et al., eds., "Calixarenes and Beyond," Springer, pp. 142-143 and 168-173 (2016).
Gutsche, "Synthesis of Calixarenes and Thiacalixarenes," in Calixarenes 2001: Kluwer Academic Publishers, pp. 1-25 (2001).
Gutsche, "Calixarenes," Royal Society of Chemistry: Chapters 2-3 (1989).

*Primary Examiner* — Sikarl A Witherspoon
(74) *Attorney, Agent, or Firm* — Jeffrey N. Townes; Cozen O'Connor

(57) ABSTRACT

This invention relates to a one-pot synthesis of a high-purity calix[4]arene compound by reacting a phenolic compound and an aldehyde in the presence of at least one nitrogen-containing base as a catalyst to form the calix[8]arene compound, and cleaving the calix[8]arene compound into a high-purity calix[4]arene compound, directly, without carrying out a purification step before the cleaving step. The invention also relates to an improved conversion of a calix[8]arene compound to a calix[4]arene compound, by cleaving a calix[8]arene compound in a glycol ether solvent having a boiling point of at least about 200° C., to result in a high-purity calix[4]arene compound, without using an antisolvent.

25 Claims, 12 Drawing Sheets

PROCESSES FOR PREPARING CALIX[4]ARENES FROM CALIX[8]ARENES

This application claims priority to U.S. Provisional Application No. 62/628,472, filed on Feb. 9, 2018, and U.S. Provisional Application No. 62/691,998, filed on Jun. 29, 2018; both of which are herein incorporated by reference in their entirety.

FIELD OF THE INVENTION

This invention generally relates to a process for preparing calixarenes.

BACKGROUND

Calixarenes have found widespread uses as complexation hosts and as frameworks for the construction of more complex structures.

Calix[4]arene compounds have been prepared from calix[8]arene compounds. However, those calix[8]arene compounds are typically synthesized by using an alkaline base, such as sodium hydroxide, as a catalyst, for instance, as described in Gutsche et al., *Organic Synthesis*, 68: 243-246 (1990). Such preparations, however, are typically low in yield and purity and need to be run in dilute reaction conditions. To obtain a high purity and high selectivity of a calix[4]arene compound, the calix[8]arene compounds typically need to be purified prior to converting to calix[4]arene compounds, for instance, as described in Gutsche et. al., *J. Org. Chem.*, 64: 3747-50 (1999).

EP 0447977A1 to Leuna-Werke A G, although discussing the preparation of para-alkylcalix[4]arenes from para-alkylcalix[8]arenes, discloses a process that is not an in-situ process starting from the preparation of high-purity calix[8]arene compounds; and the process is limited to the preparation of n-alkylcalix[4]arenes, iso-alkylcalix[4]arenes, and tert-alkylcalix[4]arenes.

Other ways have been described to prepare calix[4]arenes from alkylphenol and aqueous formaldehyde with no initial use of solvent, for instance, as described in Gutsche et al., *Organic Synthesis*, 68: 234-36 (1990). Such syntheses typically initially result in highly voluminous foams, and highly viscous, thick, unmanageable residues, thereby preventing these approaches from being used in a commercial scale synthesis.

There thus remains a need in the art to develop an improved process to prepare high-purity calix[4]arene compounds in a commercial feasible, highly efficient manner. This invention answers that need.

SUMMARY OF THE INVENTION

One aspect of the invention relates to a process for a one-pot synthesis of a high-purity calix[4]arene compound. The process comprises reacting a phenolic compound and an aldehyde in the presence of at least one nitrogen-containing base as a catalyst to form a calix[8]arene compound; and cleaving the calix[8]arene compound into a high-purity calix[4]arene compound, directly, without carrying out a purification step before the cleaving step.

In certain embodiments, the nitrogen-containing base is a sterically hindered primary amine, a sterically hindered secondary amine, a sterically hindered tertiary amine, a morpholine compound, a pyridine compound, an imidazole compound, a triamine compound, or an amino-containing ether compound.

In certain embodiments, the nitrogen-containing base is an amidine compound having the formula of

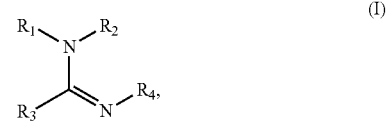

wherein $R_1$, $R_2$, $R_3$, and $R_4$ are each independently H, alkyl, cycloalkyl, heterocycloalkyl, aryl, or heteroaryl; or any two or more of $R_1$, $R_2$, $R_3$, and $R_4$ can be bonded together to form a five- to nine-membered ring structure. In one embodiment, the amidine compound is selected from the group consisting of 1,8-diazabicyclo[5.4.0]undec-7-ene (DBU), 1,5-diazabicyclo[4.3.0]non-5-ene (DBN), 1,2-dimethyl-1,4,5,6-tetrahydropyrimidine, 1-ethyl-2-methyl-1,4,5,6-tetrahydropyrimidine, 1,2-diethyl-1,4,5,6-tetrahydropyrimidine, 1-n-propyl-2-methyl-1,4,5,6-tetrahydropyrimidine, 1-isopropyl-2-methyl-1,4,5,6-tetrahydropyrimidine, 1-ethyl-2-n-propyl-1,4,5,6-tetrahydropyrimidine, and 1-ethyl-2-isopropyl-1,4,5,6-tetrahydropyrimidine.

In certain embodiments, the nitrogen-containing base is a guanidine compound having the formula of

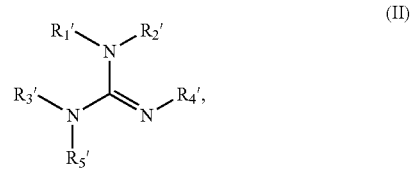

wherein $R_1'$, $R_2'$, $R_3'$, $R_4'$, and $R_5'$ are each independently H, alkyl, cycloalkyl, heterocycloalkyl, aryl, or heteroaryl; or any two or more of $R_1'$, $R_2'$, $R_3'$, $R_4'$, and $R_5'$ can be bonded together to form a five- to nine-membered ring structure. In one embodiment, the guanidine compound is selected from the group consisting of 1-methylguanidine, 1-n-butylguanidine, 1,1-dimethylguanidine, 1,1-diethylguanidine, 1,1,2-trimethylguanidine, 1,2,3-trimethylguanidine, 1,3-diphenylguanidine, 1,1,2,3,3-pentamethylguanidine, 2-ethyl-1,1,3,3-tetramethylguanidine, 1,1,3,3-tetramethyl-2-n-propylguanidine, 1,1,3,3-tetramethyl-2-isopropylguanidine, 2-n-butyl-1,1,3,3-tetramethylguanidine, 2-tert-butyl-1,1,3,3-tetramethylguanidine, 1,2,3-tricyclohexylguanidine, 1,5,7-triazabicyclo[4.4.0]dec-5-ene (TBD), 7-methyl-1,5,7-triazabicyclo[4.4.0]dec-5-ene (MTBD), 7-ethyl-1,5,7-triazabicyclo[4.4.0]dec-5-ene, 7-n-propyl-1,5,7-triazabicyclo[4.4.0]dec-5-ene, 7-isopropyl-1,5,7-triazabicyclo[4.4.0]dec-5-ene, 7-n-butyl-1,5,7-triazabicyclo[4.4.0]dec-5-ene, 7-isobutyl-1,5,7-triazabicyclo[4.4.0]dec-5-ene, 7-tert-butyl-1,5,7-triazabicyclo[4.4.0]dec-5-ene, 7-cyclohexyl-1,5,7-triazabicyclo[4.4.0]dec-5-ene, 7-n-octyl-1,5,7-triazabicyclo[4.4.0]dec-5-ene, 7-2-ethylhexyl-1,5,7-triazabicyclo[4.4.0]dec-5-ene, and 7-decyl-1,5,7-triazabicyclo[4.4.0]dec-5-ene.

In certain embodiments, the nitrogen-containing base is a tetraalkyl ammonium hydroxide. For instance, each alkyl moiety in the tetraalkyl ammonium hydroxide may be independently $C_1$ to $C_6$ alkyl.

In certain embodiments, the phenolic compound is phenol, an alkyl phenol, or an arylalkyl phenol. In one embodiment, the phenolic compound is an alkyl phenol and the alkyl group of the alkyl phenol is a tert-$C_4$-$C_{12}$ alkyl, such as a para-tert-$C_4$-$C_{12}$ alkyl phenol. In one embodiment, the phenolic compound is para-tert-butyl phenol, para-tert-amyl phenol, para-tert-octyl phenol, para-benzyl phenol, or para-benzyl phenol In certain embodiments, the aldehyde is formaldehyde or paraformaldehyde.

In certain embodiments, the reacting step is carried out in the presence of an organic solvent, and the reacting step further comprises heating the reaction mixture at an elevated temperature of about 140° C. to about 180° C. for a time period of 4 hours or longer, to remove water from the reaction mixture and selectively produce a calix[8]arene compound of at least 70% purity.

In certain embodiments, the process is carried out in the absence of a recrystallization step.

In certain embodiments, the reacting step is carried out in the presence of an organic solvent. In one embodiment, the organic solvent is an aromatic hydrocarbon, a straight-chain hydrocarbon having 11 to 20 carbon atoms, or a mixture containing thereof. In one embodiment, the organic solvent is an ether or a mixture containing thereof. For instance, the ether may be diphenyl ether or diethylene glycol dibutyl ether. In one embodiment, the step of cleaving comprises heating the calix[8]arene compound to a temperature of at least about 200° C., in the presence of a metal hydroxide catalyst. For instance, the step of cleaving may comprise heating the calix[8]arene compound at a temperature ranging from about 250 to about 260° C., in the presence of an alkali metal hydroxide catalyst, for a period of 30 minutes or longer. The process may further comprise lowering the temperature to precipitate the high-purity calix[4]arene compound. In one embodiment, the process further comprises adding an antisolvent to precipitate the calix[4]arene compound having a purity of at least 95%. For instance, the calixarene compound may contain at least 96% calix[4]arene. The antisolvent used may be an ester, ketone, alcohol, or acetonitrile. In one embodiment, the process further comprises adding an additional organic solvent to form azeotropes with water.

Another aspect of the invention relates to a process for a one-pot synthesis of a high-purity calix[4]arene compound comprising 4 units of formula (A-1):

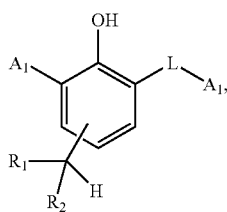

(A-1)

wherein:
each of $R_1$ and $R_2$ is independently linear, branched, or cyclic $C_1$-$C_{30}$ alkyl, aryl, alkylaryl, or arylalkyl;
each L is independently selected from the group consisting of —$CH_2$—, —C(O)—, —CH($R_3$)—, —($CH_2$)$_{n'}$—O—($CH_2$)$_{n'}$—, —C($R_3$)$_2$—;
each $R_3$ is independently a $C_1$-$C_6$ alkyl;
each n' is independently an integer from 1-2;
each $A_1$ represents a direct covalent bond to an adjacent unit of formula (A-1) such that there is one L group between adjacent units, whereby the total units in the calixarene compound form a ring.

The process comprises reacting a phenolic compound having a formula of

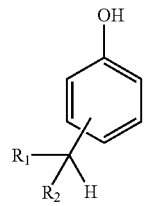

and an aldehyde in the presence of at least one nitrogen-containing base as a catalyst to form a calix[8]arene compound having 8 units of formula (A-1); and cleaving the calix[8]arene compound into the high-purity calix[4]arene compound, directly, without carrying out a purification step before the cleaving step.

In certain embodiments, each of $R_1$ and $R_2$ is independently linear $C_1$-$C_6$ alkyl. For instance, each $R_1$ is methyl, and each $R_2$ is methyl, ethyl, propyl, or hexyl.

In certain embodiments, the calix[4]arene compound is at least partially soluble in a hydrocarbon solvent at room temperature. In one embodiment, the hydrocarbon solvent is hexane, an aromatic hydrocarbon containing 7 to 12 carbon atoms, or a mixture containing thereof. In one embodiment, the solubility of the calix[4]arene compound in toluene is at least 5 wt % at about 21° C.

In certain embodiments, the reacting step is carried out in the presence of an organic solvent. In one embodiment, the organic solvent is an aromatic hydrocarbon, a straight-chain hydrocarbon having 11 to 20 carbon atoms, or a mixture containing thereof. In one embodiment, the organic solvent is an ether or a mixture containing thereof. For instance, the ether is diphenyl ether, diethylene glycol dimethyl ether, triethylene glycol dimethyl ether, or diethylene glycol dibutyl ether. In one embodiment, the step of cleaving comprises heating the calix[8]arene compound to a temperature of at least about 200° C., in the presence of a metal hydroxide catalyst. For instance, the step of cleaving comprises heating the calix[8]arene compound at a temperature ranging from about 250 to about 260° C., in the presence of an alkali metal hydroxide catalyst, for a period of 30 minutes or longer. The process may further comprise lowering the temperature to precipitate the high-purity calix[4]arene compound. The process may further comprise adding an antisolvent to precipitate the calix[4]arene compound having a purity of at least 94%. For instance, the calixarene compound may contain at least 95% calix[4]arene. The antisolvent used may be acetone or isopropanol. The process may further comprise, prior to adding the antisolvent, neutralizing the metal hydroxide catalyst by adding an acid; and removing, at least partially, the organic solvent by distillation. In one embodiment, the process further comprises adding an additional organic solvent to form azeotropes with water.

Another aspect of the invention relates to a process for improved conversion of a calix[8]arene compound to a calix[4]arene compound. The process comprises providing a calix[8]arene compound; and cleaving the calix[8]arene compound in a glycol ether solvent having a boiling point of at least about 200° C., to result in a high-purity calix[4]arene compound, without using an antisolvent.

In certain embodiments, the glycol ether solvent has a boiling point ranging from about 250 to about 260° C. For instance, the glycol ether solvent is diethylene glycol dibutyl ether.

In certain embodiments, the step of cleaving comprises heating the calix[8]arene compound at a temperature of at least about 200° C., in the presence of a metal hydroxide catalyst. In one embodiment, the step of cleaving comprises heating the calix[8]arene compound at a temperature ranging from about 250 to about 260° C., in the presence of an alkali metal hydroxide catalyst, for a period of about 30 minutes or longer; and lowering the temperature to precipitate the calix[4]arene compound having a purity of at least 98%. In one embodiment, the step of cleaving comprises heating the calix[8]arene compound at a temperature ranging from about 250 to about 260° C., in the presence of an alkali metal hydroxide catalyst, for a period of 2 hours or longer; and lowering the temperature to precipitate the calix[4]arene compound having a purity of at least 99%.

In certain embodiments, the step of providing a calix[8]arene compound comprises reacting a phenolic compound, an aldehyde, and a nitrogen-containing base as a catalyst, in the presence of an organic solvent; and heating the reaction mixture at an elevated temperature of about 140° C. to about 180° C. for a time period of 4 hours or longer, to remove water from the reaction mixture and selectively produce a calixarene compound containing at least 70% calix[8]arene. In one embodiment, the phenolic compound is phenol, an alkyl phenol, or an arylalkyl phenol. For instance, the phenolic compound may be an alkyl phenol and the alkyl group of the alkyl phenol is a tert-$C_4$-$C_{12}$ alkyl. In one embodiment, the phenolic compound is a para-tert-butyl phenol, para-tert-amyl phenol, or para-tert-octyl phenol, para-benzyl phenol, or para-benzyl phenol. In one embodiment, the aldehyde is formaldehyde or paraformaldehyde.

Yet another aspect of the invention relates to a process for improved conversion of a calix[8]arene compound to a calix[4]arene compound. The process comprises providing a calix[8]arene compound comprising 8 units of formula (A-1); and cleaving the calix[8]arene compound in an organic solvent having a boiling point of at least about 200° C., to result in a high-purity calix[4]arene compound, without using an antisolvent. Formula (A-1) is represented below:

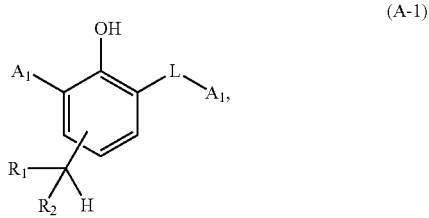

(A-1)

wherein:
each of $R_1$ and $R_2$ is independently linear, branched, or cyclic $C_1$-$C_{30}$ alkyl, aryl, alkylaryl, or arylalkyl;
each L is independently selected from the group consisting of —$CH_2$—, —C(O)—, —CH($R_3$)—, —($CH_2$)$_{n'}$—O—($CH_2$)$_{n'}$—, —C($R_3$)$_2$—;
each $R_3$ is independently a $C_1$-$C_6$ alkyl;
each n' is independently an integer from 1-2;
each $A_1$ represents a direct covalent bond to an adjacent unit of formula (A-1) such that there is one L group between adjacent units, whereby the total units in the calixarene compound form a ring.

In certain embodiments, the organic solvent has a boiling point ranging from about 250 to about 260° C.

In certain embodiments, organic solvent is a glycol ether solvent. For instance, the glycol ether solvent is diethylene glycol dibutyl ether.

In certain embodiments, the step of cleaving comprises heating the calix[8]arene compound at a temperature of at least about 200° C., in the presence of a metal hydroxide catalyst; and lowering the temperature to precipitate the calix[4]arene compound having a high purity. In one embodiment, the step of cleaving comprises heating the calix[8]arene compound at a temperature ranging from about 250 to about 260° C., in the presence of an alkali metal hydroxide catalyst, for a period of 30 minutes or longer; and lowering the temperature to precipitate the calix[4]arene compound having a purity of at least 98%. In one embodiment, the step of cleaving comprises heating the calix[8]arene compound at a temperature ranging from about 250 to about 260° C., in the presence of an alkali metal hydroxide catalyst, for a period of 2 hours or longer; and lowering the temperature to precipitate the calix[4]arene compound having a purity of at least 99%.

In certain embodiments, the step of providing a calix[8]arene compound comprises reacting a phenolic compound having a formula of

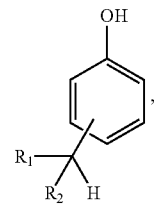

, an aldehyde, and a nitrogen-containing base as a catalyst, in the presence of an organic solvent; and heating the reaction mixture at an elevated temperature of about 140° C. to about 180° C. for a time period of 4 hours or longer, to remove water from the reaction mixture and selectively produce a calixarene compound containing at least 70% calix[8]arene. In one embodiment, each of $R_1$ and $R_2$ is independently linear $C_1$-$C_6$ alkyl. For instance, each $R_1$ is methyl, and each $R_2$ is methyl, ethyl, propyl, or hexyl. In one embodiment, the aldehyde is formaldehyde or paraformaldehyde.

DETAILED DESCRIPTION OF THE INVENTION

Preparation of a High-Purity Calix[8]Arene

Figure 1A:
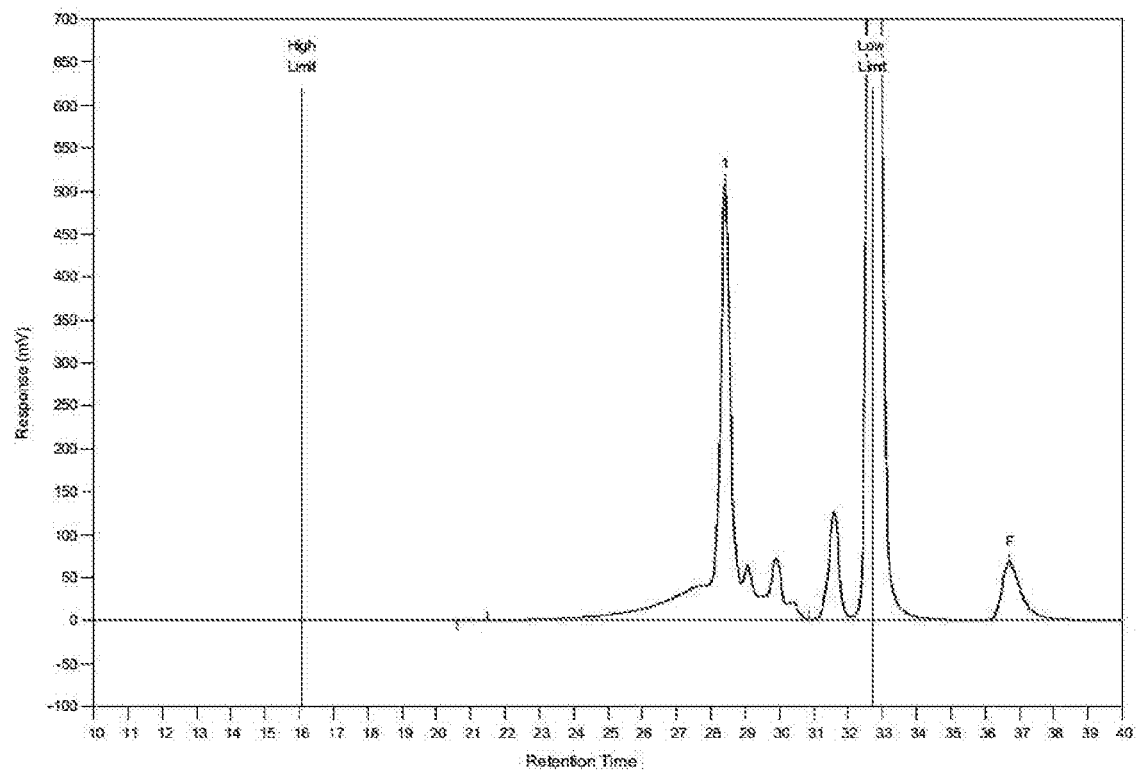
FIG. 1 shows the GPC results (FIG. 1A) and $^1$H-NMR results (FIG. 1B) of the intermediate tert-amylcalix[8]arene reaction mass, and the GPC results (FIG. 1C) and $^1$H-NMR results (FIG. 1D) of the tert-amylcalix[4]arene crude reaction mass prepared from the one-pot, in-situ process illustrated in Example 14.

One aspect of the invention relates to a process for preparing a high-purity calixarene compound, comprising reacting a phenolic compound and an aldehyde in the presence of at least one nitrogen-containing base as a catalyst to form a calixarene compound.

The phenolic compound may be a monohydric, dihydric, or polyhydric phenol, or its derivative, with or without substituent(s) on the benzene ring of the phenolic compound. Suitable monohydric, dihydric, or polyhydric phenols include, but are not limited to, phenol; dihydric-phenols such as resorcinol, catechol, and hydroquinone; trihydric-phenols such as pyrogallol, hydroxy quinol, or phloroglucinol; dihydroxybiphenol such as 4,4'-biphenol; alkylidenebisphenols (the alkylidene group can have 1-12 carbon atoms) such as 4,4'-methylenediphenol (bisphenol F), and 4,4'-isopropylidenediphenol (bisphenol A); trihydroxybiphenol; and thiobisphenols. Exemplary monohydric, dihydric, or polyhydric phenols include phenol, resorcinol, and pyrogallol. In one embodiment, the phenolic compound is phenol.

Suitable phenolic compounds also include a monoether derivative or diether derivative of the monohydric, dihydric, or polyhydric phenols. The ether derivative of the monohydric, dihydric, or polyhydric phenols may be an alkyl ether, an aryl ether, or an alkyl aryl ether, which may be optionally substituted with a hydroxy, alkoxy, alkylene oxide, or acryloxy group. For instance, the ether derivative may be a monoalkyl ether, dialkyl ether, monoglycidyl ether, diglycidyl ether, or benzyloxy ether group, or mixtures thereof.

The benzene ring of the monohydric, dihydric, or polyhydric phenol, or its derivative can be substituted in the ortho, meta, and/or para positions by one or more linear, branched, or cyclic $C_1$-$C_{30}$ alkyl, or halogen (F, Cl, or Br). The one or more substituents on the benzene ring of the phenolic compound may be $C_1$-$C_{30}$ alkyl, aryl, alkylaryl, or arylalkyl. For example, the benzene ring of the phenolic compound can be substituted by $C_1$-$C_{24}$ alkyl, $C_1$-$C_{16}$ alkyl, $C_4$-$C_{16}$ alkyl, or $C_4$-$C_{12}$ alkyl (such as tert-$C_4$-$C_{12}$ alkyl). Suitable substituents on the benzene ring also include aryl, such as phenyl; $C_1$-$C_{30}$ arylalkyl (such as benzyl or cumyl); or $C_1$-$C_{30}$ alkylaryl.

In certain embodiments, the phenolic compound is phenol, resorcinol, pyrogallol, 4,4'-biphenol, 4,4'-methylenediphenol, or 4,4'-isopropylidenediphenol, each having the benzene ring being substituted with H or $C_1$-$C_{24}$ alkyl (e.g., $C_4$ to $C_{12}$ alkyl).

In certain embodiments, the phenolic compound is a mono- or di-ether (e.g., a $C_1$-$C_6$ alkyl ether or glycidyl ether) of phenol, resorcinol, pyrogallol, 4,4'-biphenol, 4,4'-methylenediphenol, or 4,4'-isopropylidenediphenol, each having the benzene ring being substituted with H or $C_1$-$C_{24}$ alkyl (e.g., $C_4$ to $C_{12}$ alkyl).

When the phenolic compound is a substituted phenol, the phenolic compound typically contains one substituent at the para position. In one embodiment, the phenolic compound is phenol, an arylalkyl phenol (such as para-benzylphenol or para-cumylphenol), or an alkylphenol, particularly a para-$C_1$-$C_{24}$ (linear, branched, or cyclic) alkylphenol, such as para-methylphenol, para-ethylphenol, para-isopropylphenol, para-tert-butylphenol (PTBP), para-sec-butylphenol, para-tert-amylphenol (PTAP), para-tert-hexylphenol, para-cyclohexylphenol, para-sec-octylphenol, para-tert-octylphenol (PTOP), para-isooctylphenol, para-decylphenol, para-dodecylphenol, para-tetradecyl phenol, para-octadecylphenol, para-nonylphenol, para-pentadecylphenol, para-cetylphenol, para-adamantylphenol, and para-(2-isopropyl-5-methylcyclohexyl)phenol. Typical alkyl phenols include para-tert-$C_4$-$C_{12}$ alkylphenols, such as para-tert-$C_4$-$C_8$ alkylphenols.

Suitable phenolic compounds also include those phenols described in Gutsche, "Chapter 1. Synthesis of Calixarenes and thiacalixarenes," *Calixarenes* 2001 (Edited by M.-Z. Asfari et. al., Kluwer Academic Publishers, 2001), pages 1-25, which is incorporated herein by reference in its entirety, to the extent not inconsistent with the subject matter of this disclosure.

In certain embodiments, the process is used for preparing a calixarene compound with a high solid-content, or for the selective synthesis of a calix[8]arene compound. Exemplary phenolic compounds are phenol, a $C_4$ to $C_8$ alkyl phenol (linear, branched, or cyclic) (e.g., a para-tert-$C_4$-$C_8$ alkylphenol), and an arylalkyl phenol (such as benzyl phenol or cumyl phenol).

Any aldehyde known in the art for preparing a phenolic resin (linear or cyclic) is suitable in this process. Exemplary aldehydes include formaldehyde, methyl formcel (i.e., formaldehyde in methanol), butyl formcel, acetaldehyde, propionaldehyde, butyraldehyde, crotonaldehyde, valeraldehyde, caproaldehyde, heptaldehyde, benzaldehyde, as well as compounds that decompose to aldehyde such as paraformaldehyde, trioxane, furfural (e.g., furfural or hydroxymethylfurfural), hexamethylenetriamine, aldol, 3-hydroxybutyraldehyde, and acetals, and mixtures thereof. A typical aldehyde used is formaldehyde or paraformaldehyde.

To prepare a calixarene compound, the molar ratio of the total amount of the phenolic compounds to the total amount of the aldehyde added to the reaction typically ranges from about 0.5:1 to about 2:1, for instance, from about 1:1.5 to about 1.5:1, from about 1:1.3 to about 1.3:1, or from about 1:1.15 to about 1:1.

The term "calixarene" generally refers to a variety of derivatives that may have one or more substituent groups on the hydrocarbons of cyclo{oligo[(1,3-phenylene)methylene]}. The term "calixarene" also generally encompasses the cyclic structure formed by not only a monohydric phenol, such as phenol or alkylphenol, but also a dihydric or polyhydric phenol, or a derivative thereof. The calixarenes may contain a substituent on the benzene ring of calixarenes.

Exemplary cyclic structures of the calixarenes are those formed by phenol, resorcinol, or pyrogallol.

A typical calixarene compound based on phenols has a structure of Formula (A'):

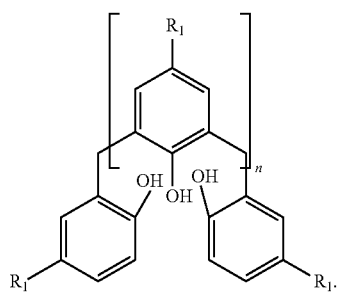

(A')

A typical calixarene compound based on resorcinols has a structure of Formula (B-1') or (B-2'):

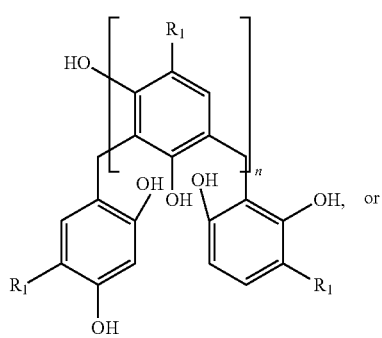

(B-1')

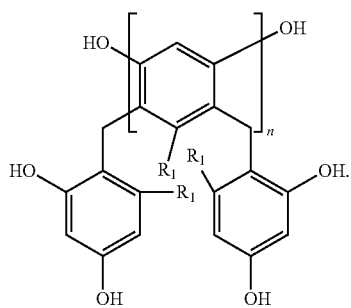

(B-2')

A typical calixarene compound based on pyrogallols has a structure of Formula (C'):

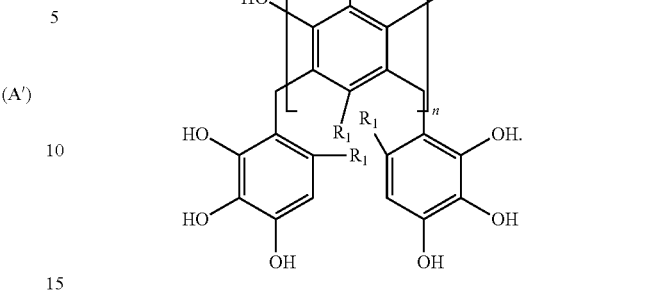

(C')

In Formulas (A'), (B-1'), (B-2'), and (C'), the substituent group $R_1$ on the benzene ring of the calixarene compound depends on the phenolic compounds used in the process to prepare the calixarene compound. For instance, $R_1$ may be H, $C_1$-$C_{30}$ alkyl, aryl, alkylaryl, or arylalkyl. All above descriptions in the context of the substituents on the benzene ring of the phenolic compound are applicable to the definition of $R_1$. The number of units of phenolic monomers of the calixarene (e.g., n in Formulas (A'), (B-1'), (B-2'), and (C')) may be 2 to 100, for instance, 2 to 50, 2 to 30, 2 to 20, 2 to 10, 2 to 8, 2 to 6, or 2 to 4, resulting in a molecular weight typically ranging from about 500 to about 25,000 daltons, from about 500 to about 10,000 daltons, from about 500 to about 5,000 daltons, from about 1,000 to about 5,000 daltons, from about 500 to about 3,000 daltons, or from about 500 to about 1,000 daltons.

In certain embodiments, the calixarene compound comprises n units of phenolic monomers of Formula (A):

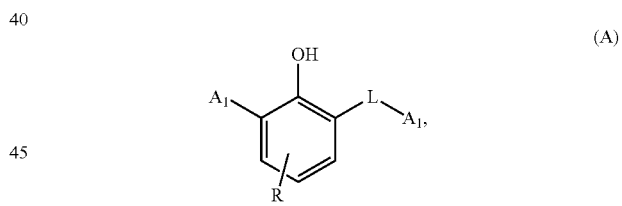

(A)

in which the substituent group R on the benzene ring of the calixarene compound depends on the phenolic compounds used in the process to prepare the calixarene compound. For instance, R may be H, $C_1$-$C_{30}$ alkyl, aryl, alkylaryl, or arylalkyl. All above descriptions in the context of the substituents on the benzene ring of the phenolic compound are applicable to the definition of R. Each $A_1$ represents a direct covalent bond to an adjacent unit of Formula (A) such that there is one L group between adjacent units, whereby the total units in the calixarene compound form a ring. The L group depends on the aldehyde used in the process to prepare the calixarene compound. For instance, each L may be independently selected from the group consisting of —$CH_2$—, —C(O)—, —CH($R_3$)—, —$(CH_2)_{n'}$—O—$(CH_2)_{n'}$—, and —C($R_3$)$_2$—; each $R_3$ may be independently a $C_1$-$C_6$ alkyl; and each n' may be independently an integer from 1 to 2. Typically, when formaldehyde is used, L may be —CH$_2$— or —CH$_2$—O—CH$_2$—.

Typically, in the case of a monohydric phenol with a substituent group being used to form the calixarene compound, if the substituent group is at the para position to the hydroxyl group of the phenolic compound, the resulting alkylene bridge (e.g., methylene bridge if formaldehyde is used) extends in the ortho positions to the hydroxyl group of the phenolic compound (see, e.g., Formula (A')). If the substituent group is at the ortho position to the hydroxyl group of the phenolic compound, the resulting alkylene bridge can extend in the para position to the hydroxyl group of the phenolic compound and the other substituted ortho position to the hydroxyl group of the phenolic compound. In the case of a dihydric phenol being used to form the phenolic resin, the location of the alkylene bridge (e.g., methylene bridge, if formaldehyde is used) can also vary depending on the relative position of the hydroxyl groups and the substituent groups. For instance, two possible connections of the phenolic units are shown in Formula (B-1') and (B-2') above. In the case of a trihydric phenol being used to form the phenolic resin, the location of the alkylene bridge (e.g., methylene bridge, if formaldehyde is used) can also vary depending on the relative positions of the hydroxyl groups and the substituent group. For instance, a possible connection of the phenolic units is shown in Formula (C') above.

The number of units of phenolic monomers in the calixarene compound (e.g., n in the context of Formula (A)) may be 2 to 100, for instance, 2 to 50, 2 to 30, 2 to 20, 2 to 10, 2 to 8, 2 to 6, or 2 to 4, resulting in a molecular weight typically ranging from about 500 to about 25,000 daltons, from about 500 to about 10,000 daltons, from about 500 to about 5,000 daltons, from about 1,000 to about 5,000 daltons, from about 500 to about 3,000 daltons, or from about 500 to about 1,000 daltons.

The term "calix[n]arene" typically specifies the number of units of phenolic monomers in the calixarene compound prepared. For instance, a calix[8]arene compound is a calixarene compound having 8 units of phenolic monomers.

An exemplary calix[8]arene structure is shown as below:

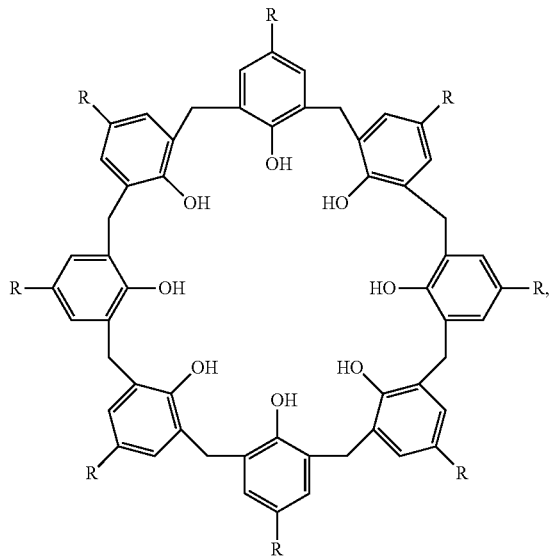

in which the phenolic compound used in the process has a substituent group, R, at the para position to the hydroxyl group of the phenolic compound and the aldehyde used in the process is formaldehyde.

The calixarene compound may be prepared from one or more phenolic compounds reacting with one or more aldehydes forming an oligomer of phenolic monomers. The resulting calixarene compound may be a homopolymer of the same phenolic monomer, or a copolymer containing different units of phenolic monomers, e.g., when two or more different phenolic compounds were reacted with an aldehyde.

In certain embodiments, the phenolic units in the calixarene compound can be resulting from the same or different phenolic compounds. The benzene ring of each phenolic unit can be independently substituted with a same or different substituent group R. For instance, the phenolic units in the calixarene compound are the same or different phenols, and the benzene ring of each phenol is independently substituted with H or $C_1$ to $C_{20}$ alkyl (e.g., $C_4$ to $C_{12}$ alkyl).

In certain embodiments, the calixarene compound comprises n units of phenolic monomers of Formula (A-1):

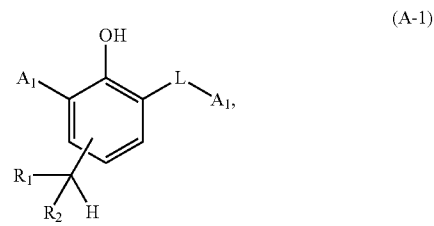

in which each of $R_1$ and $R_2$ is independently linear, branched, or cyclic $C_1$-$C_{30}$ alkyl, aryl, alkylaryl, or arylalkyl. For instance, each of $R_1$ and $R_2$ may be independently $C_1$-$C_{12}$ alkyl (linear, branched, or cyclic), or $C_1$-$C_6$ alkyl (linear). In one embodiment, each $R_1$ is methyl, and each $R_2$ is methyl, ethyl, propyl, or hexyl.

Each $A_1$ represents a direct covalent bond to an adjacent unit of Formula (A-1) such that there is one L group between adjacent units, whereby the total units in the calixarene compound form a ring. The L group depends on the aldehyde used in the process to prepare the calixarene compound. For instance, each L may be independently selected from the group consisting of —CH$_2$—, —C(O)—, —CH(R$_3$)—, —(CH$_2$)$_{n'}$—O—(CH$_2$)$_{n'}$—, and —C(R$_3$)$_2$—; each $R_3$ may be independently a $C_1$-$C_6$ alkyl; and each n' may be independently an integer from 1 to 2. Typically, when formaldehyde is used, L is —CH$_2$— or —CH$_2$—O—CH$_2$—.

The total number of units in the calixarene compound of Formula (A-1), i.e., n, is an integer that typically ranges from 2-20. In one embodiment, n is from 4-10, for instance, 4, 5, 6, 7, 8, 9, or 10.

In one embodiment, the substituent group

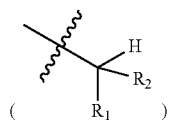

on the calixarene compound of Formula (A-1) is at the para position to the hydroxyl group.

The calixarene compounds described above can exist in one or more stereoisomeric forms, depending on the reaction conditions and/or the chirality of the starting phenolic compounds. For instance, when using a phenolic compound with a chiral center

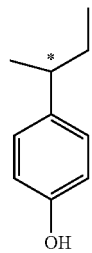

(* indicates the chiral center), the resulting calixarene compound may contain stereoisomeric forms, e.g.,

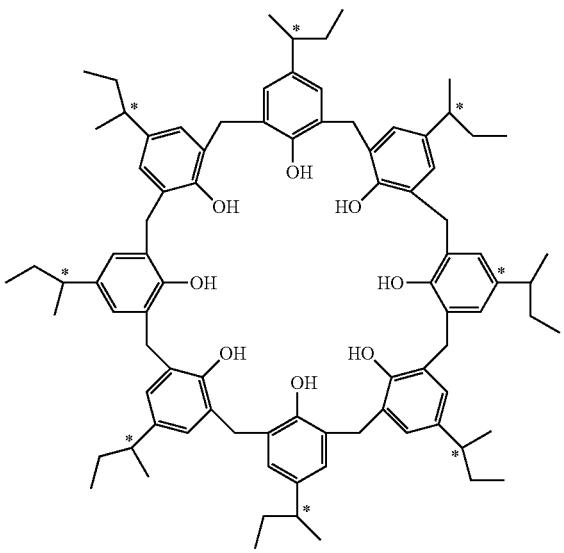 [SMILES: CCC(C)c1cc2c(O)c(c1)Cc1cc(C(C)CC)cc(c1O)Cc1cc(C(C)CC)cc(c1O)Cc1cc(C(C)CC)cc(c1O)Cc1cc(C(C)CC)cc(c1O)Cc1cc(C(C)CC)cc(c1O)Cc1cc(C(C)CC)cc(c1O)Cc1cc(C(C)CC)cc(c1O)C2]

(* indicates the chiral center). However, the calixarene compounds may be a mixture in which the stereoisomeric forms may not be easy to be separated. When the starting phenolic compound does not contain a chiral center (for instance, an isopropylphenol), the resulting calixarene compounds would not form different diastereomers.

Exemplary calixarene compounds for the calixarene compound of Formula (A-1) have the structures of

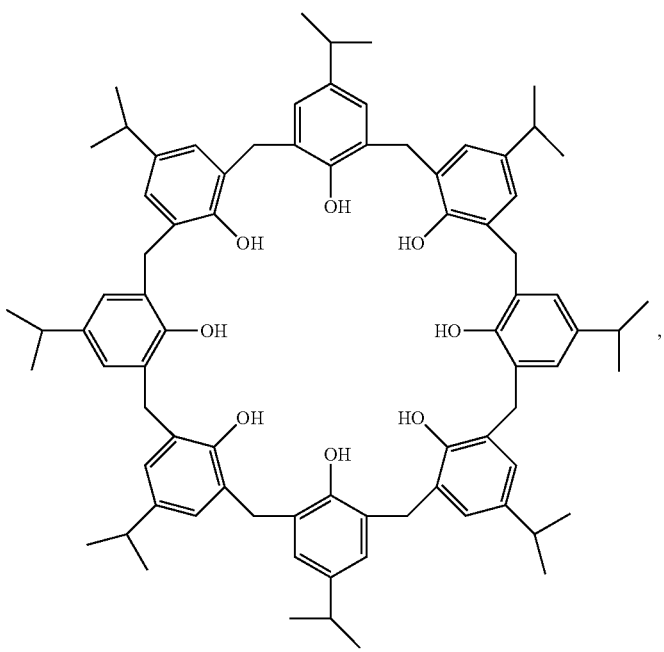

-continued
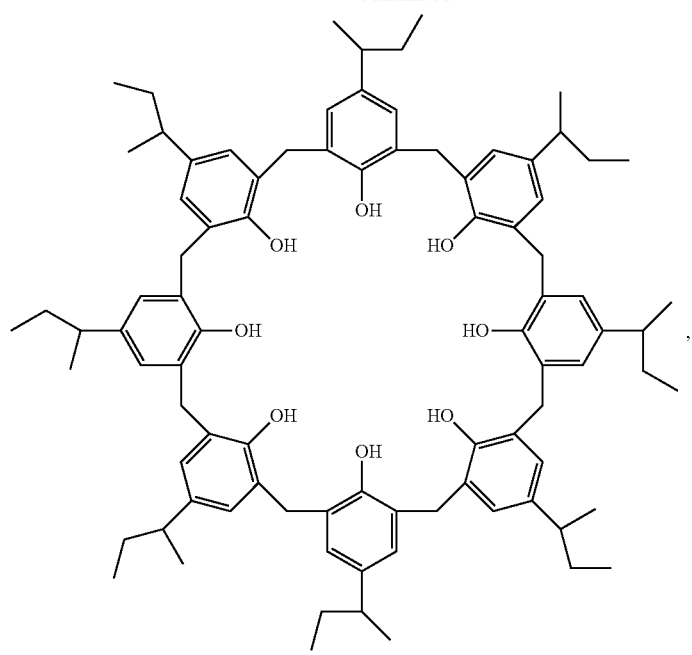
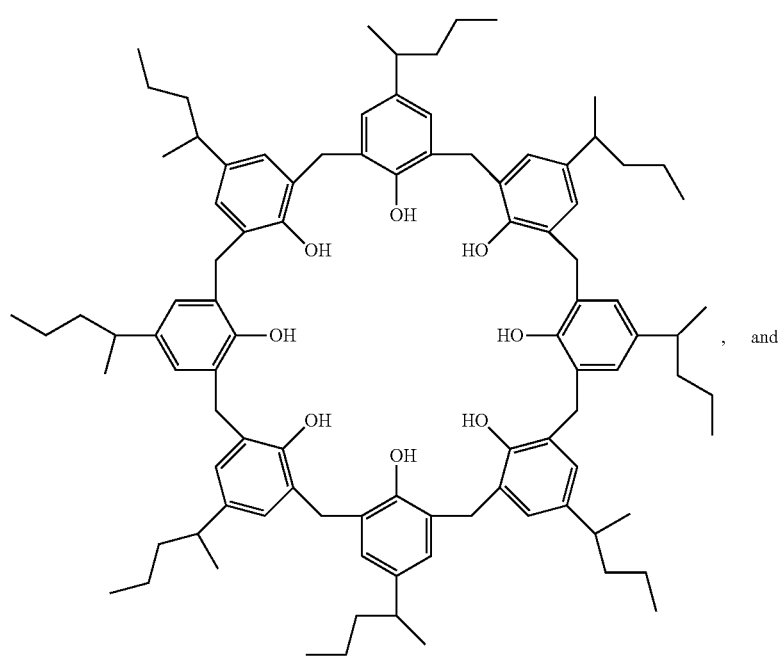

-continued

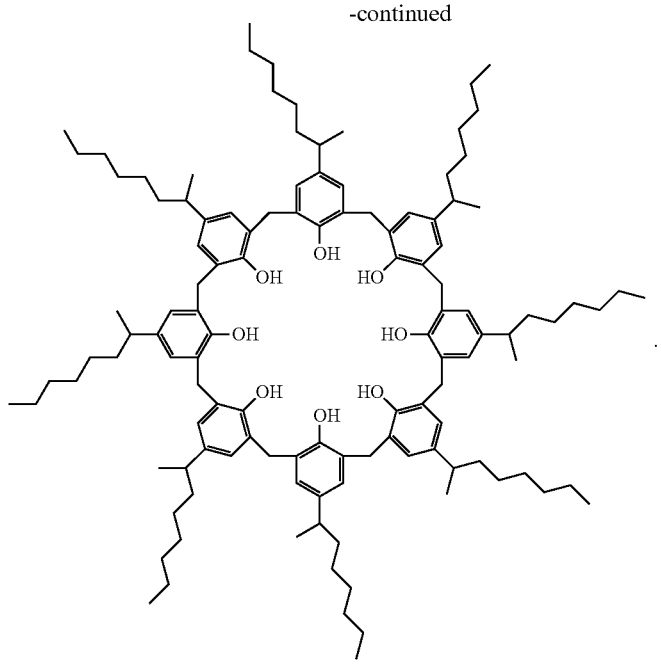

Catalyst

A nitrogen-containing base, such as a sterically hindered amine, has a weaker basicity than most alkaline base catalysts, such as sodium hydroxide or potassium hydroxide, the catalysts conventionally used for the synthesis of calixarene compounds, including a calix[8]arene compound. Thus, the conventional alkaline base catalysts convert the formaldehyde faster during the condensation reaction, following a kinetic route different than the kinetic route when using a nitrogen-containing base, such as a sterically hindered amine, as the catalyst. Because of this, these conventional alkaline base catalysts typically produce significant amounts of other ring-sized calixarenes (e.g., about 13% of calix[4]arenes and calix[6]arenes). The nitrogen-containing base catalysts discussed herein, however, allow for a slower build-up of desirable linear precursors for the cyclic compounds (calixarenes) formation, thereby eventually resulting in a higher selectivity toward calix[8]arenes. Because of their weaker basicity than conventional alkaline base catalysts, the nitrogen-containing base catalysts discussed herein also display milder reaction conditions.

The nitrogen-containing base used herein typically has a relatively high boiling point. For instance, the nitrogen-containing base may have a boiling point of no less than about 80° C., for instance, no less than about 90° C., no less than about 100° C., no less than about 110° C., no less than about 120° C., no less than about 130° C., or no less than about 140° C. Because of this high boiling point, the nitrogen-containing base is usually not removed during the reaction of the phenolic compounds and the aldehyde, under the reflux and/or distillation conditions.

In addition, when using the nitrogen-containing base as a catalyst for the reaction between the phenolic compound and aldehyde, the weak acid phenol can protonate the nitrogen atom in the nitrogen-containing base. This prevents, or substantially inhibits, the nitrogen-containing base from being removed during the reaction of the phenolic compounds and aldehyde, under the reflux and/or distillation conditions.

As defined herein, a nitrogen-containing base may generally include a sterically hindered amine (e.g., a sterically hindered primary amine, a sterically hindered secondary amine, and a sterically hindered tertiary amine) and a sterically hindered quaternary ammonium hydroxide, such as a tetraalkyl ammonium hydroxide.

Suitable sterically hindered amine compounds include an amidine compound having the formula of

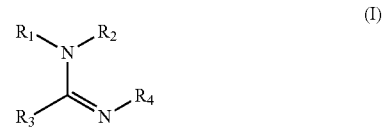

(I)

and a guanidine compound having the formula of

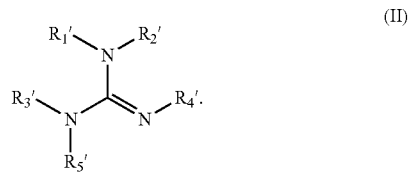

(II)

For the amidine compounds having the formula of

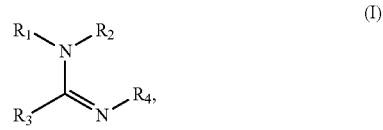

(I)

$R_1$, $R_2$, $R_3$, and $R_4$ are each independently H, alkyl, cycloalkyl, heterocycloalkyl, aryl, or heteroaryl; or any two or more of $R_1$, $R_2$, $R_3$, and $R_4$ can be bonded together to form a five- to nine-membered ring structure. For instance, $R_1$, $R_2$, $R_3$, and $R_4$ are each independently H, $C_1$ to $C_8$ alkyl, $C_5$ to $C_7$ cycloalkyl, $C_5$ to $C_7$ heterocycloalkyl, phenyl, or $C_5$ to $C_7$ heteroaryl; or any two or more of $R_1$, $R_2$, $R_3$, and $R_4$ can be bonded together to form a five-, six-, or seven-membered ring structure.

Suitable amidine compounds include 1,8-diazabicyclo[5.4.0]undec-7-ene (DBU), 1,5-diazabicyclo[4.3.0]non-5-ene (DBN), 1,2-dimethyl-1,4,5,6-tetrahydropyrimidine, 1-ethyl-2-methyl-1,4,5,6-tetrahydropyrimidine, 1,2-diethyl-1,4,5,6-tetrahydropyrimidine, 1-n-propyl-2-methyl-1,4,5,6-tetrahydropyrimidine, 1-isopropyl-2-methyl-1,4,5,6-tetrahydropyrimidine, 1-ethyl-2-n-propyl-1,4,5,6-tetrahydropyrimidine, and 1-ethyl-2-isopropyl-1,4,5,6-tetrahydropyrimidine. Exemplary amidine compounds used as the catalyst include DBU

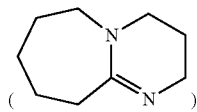

and DBN

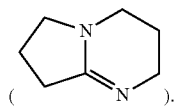

For the guanidine compounds having the formula of

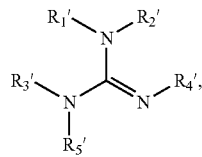

$R_1'$, $R_2'$, $R_3'$, $R_4'$, and $R_5'$ are each independently H, alkyl, cycloalkyl, heterocycloalkyl, aryl, or heteroaryl; or any two or more of $R_1'$, $R_2'$, $R_3'$, $R_4'$, and $R_5'$ can be bonded together to form a five- to nine-membered ring structure. For instance, $R_1'$, $R_2'$, $R_3'$, $R_4'$, and $R_5'$ are each independently H, $C_1$ to $C_8$ alkyl, $C_5$ to $C_7$ cycloalkyl, $C_5$ to $C_7$ heterocycloalkyl, phenyl, or $C_5$ to $C_7$ heteroaryl; or any two or more of $R_1'$, $R_2'$, $R_3'$, $R_4'$, and $R_5'$ can be bonded together to form a five-, six-, or seven-membered ring structure.

Suitable guanidine compounds include 1-methylguanidine, 1-n-butylguanidine, 1,1-dimethylguanidine, 1,1-diethylguanidine, 1,1,2-trimethylguanidine, 1,2,3-trimethylguanidine, 1,3-diphenylguanidine, 1,1,2,3,3-pentamethylguanidine, 2-ethyl-1,1,3,3-tetramethylguanidine, 1,1,3,3-tetramethyl-2-n-propylguanidine, 1,1,3,3-tetramethyl-2-isopropylguanidine, 2-n-butyl-, 1,3,3-tetramethylguanidine, 2-tert-butyl-1,1,3,3-tetramethylguanidine, 1,2,3-tricyclohexylguanidine, 1,5,7-triazabicyclo[4.4.0]dec-5-ene (TBD), 7-methyl-1,5,7-triazabicyclo[4.4.0]dec-5-ene (MTBD), 7-ethyl-1,5,7-triazabicyclo[4.4.0]dec-5-ene, 7-n-propyl-1,5,7-triazabicyclo[4.4.0]dec-5-ene, 7-isopropyl-1,5,7-triazabicyclo[4.4.0]dec-5-ene, 7-n-butyl-1,5,7-triazabicyclo[4.4.0]dec-5-ene, 7-isobutyl-1,5,7-triazabicyclo[4.4.0]dec-5-ene, 7-tert-butyl-1,5,7-triazabicyclo[4.4.0]dec-5-ene, 7-cyclohexyl-1,5,7-triazabicyclo[4.4.0]dec-5-ene, 7-n-octyl-1,5,7-triazabicyclo[4.4.0]dec-5-ene, 7-2-ethylhexyl-1,5,7-triazabicyclo[4.4.0]dec-5-ene, 7-decyl-1,5,7-triazabicyclo[4.4.0]dec-5-ene. Exemplary guanidine compounds used as the catalyst include TBD

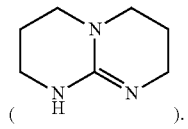

Other suitable nitrogen-containing bases include sterically hindered primary amines (e.g., triphenylmethylamine or 1,1-diethyl-n-propylamine); sterically hindered secondary amines (e.g., dicyclohexylamine, t-butylisopropylamine, di-t-butylamine, cyclohexyl-t-butylamine, di-sec-butylamine, dicyclopentylamine, di-(α-trifluoromethylethyl)amine, or di-(α-phenylethyl)amine)); sterically hindered tertiary amines (e.g., dicyclohexylmethylamine, ethyldiisopropylamine, dimethylcyclohexylamine, dimethylisopropylamine, methylisopropylbenzylamine, methylcyclopentylbenzylamine, isopropyl-sec-butyl-trifluoroethylamine, diethyl-(α-phenylethyl)amine, trialkylenediamine such as triethylenediamine (1,4-diazabicyclo[2.2.2]octane, DABCO), or trialkylamine such as trimethylamine, triethylamine, or tri-n-propylamine); morpholine compounds (e.g., morpholine, N-ethylmorpholine, N-methylmorpholine, dimorpholinodimethylether, or dimorpholinodiethyl ether); imidazole compounds (e.g., imidazole, 2-methylimidazole, n-methylimidazole, or 1,2-dimethylimidazole); pyridine compounds (e.g., pyridine, 4-methylaminopyridine, 2-methylaminopyridine, or 4-dimethylaminopyridine); triamine compounds (e.g., N,N,N',N',N",N"-pentamethyldiethylenetriamine, N,N,N',N',N",N"-pentaethyldiethylenetriamine, or N,N,N',N',N",N"-pentamethyldipropylenetriamine), and amino-containing ether compounds (e.g., bis(dimethylaminoethyl)ether, bis(diethylaminoethyl)ether, or bis(dimethylaminopropyl) ether). Exemplary nitrogen-containing bases from this group include triethylamine

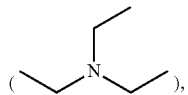

ethyldiisopropylamine

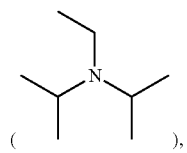

DABCO

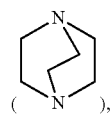

imidazole

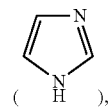

2-methylimidazole

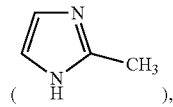

pyridine, and 4-dimethylaminopyridine

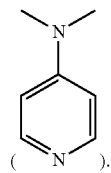

The sterically hindered quaternary ammonium hydroxide typically includes a tetraalkyl ammonium hydroxide. Each alkyl moiety in the tetraalkyl ammonium hydroxide can be independently $C_1$ to $C_6$ alkyl, for instance, $C_1$ to $C_4$ alkyl. Exemplary tetraalkyl ammonium hydroxides used as the catalyst include tetramethyl ammonium hydroxide

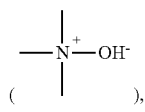

tetraethylammonium hydroxide

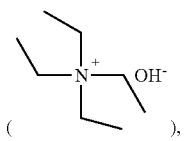

tetrapropylammonium hydroxide

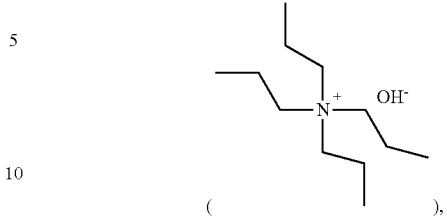

and tetrabutylammonium hydroxide

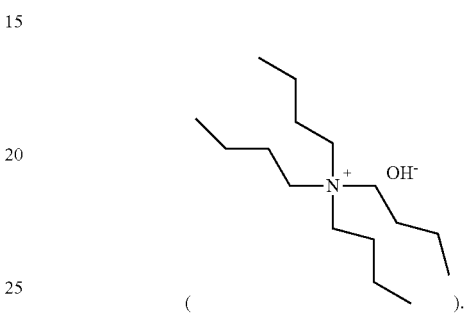

The molar ratio of the total amount of the phenolic compounds to the nitrogen-containing base catalyst added to the reaction typically ranges from about 200:1 to about 20:1, for instance, from about 100:1 to about 40:1, from about 70:1 to about 40:1, or from about 65:1 to about 45:1.

Solvent

The reaction of the phenolic compound and the aldehyde is typically carried out in the presence of an organic solvent. Suitable organic solvents are non-reactive and have low viscosity, including but not limited to, aliphatic solvents including alkanes (such as alkanes having 4 to 24 carbon atoms; e.g., alkanes having 11 to 20 carbon atoms, or having 5 to 16 carbon atoms) and cycloalkanes (such as cycloalkanes having 3 to 24 carbon atoms; e.g., cycloalkanes having 5 to 16 carbon atoms); aromatic solvents (such as alkylbenzenes or naphthalenes; e.g., an aromatic hydrocarbon solvent containing 7 to 12 carbon atoms); ethers including aromatic ethers (such as diphenyl ether) and ethers based on ethylene glycol (such as diethylene glycol dibutyl ether ("Diglybe") or diethylene glycol dimethyl ether); and mixtures containing thereof.

Exemplary organic solvents include xylene, toluene, benzene, naphthalene, an aromatic 150 fluid (i.e., an aromatic hydrocarbon solvent having a main component ranging from 9 to 12 carbon atoms, such as Solvesso™ 150 fluid or other similar aromatic hydrocarbon solvents marketed under different brands; A-150), diphenyl ether, diethylene glycol dimethyl ether, diethylene glycol dibutyl ether, Dowtherm A (a mixture of diphenylether and biphenyl), nonane, octane, hexadecane, and mixtures containing thereof.

Suitable organic solvents also include those hydrocarbon solvents having a high boiling point, such as a straight-chain $C_{11}$ to $C_{20}$ hydrocarbon having a boiling point ranging from about 250 to about 260° C., and mixtures containing thereof. Such solvents can be obtained from a petroleum middle distillate that contain a paraffin mixture having a distillation range from about 250 to about 260° C. Using high boiling point solvents may also result in a higher yield and higher selectivity toward cyclic compounds (calixarenes) over linear compounds (linear phenolic resins) in the cyclization phase, compared against the organic solvents with a lower boiling point (such as A-150). In one embodiment, tert-octylcalix[8]arenes prepared in hexadecane has an isolated yield of about 15% higher than the isolated yield of tert-octylcalix[8]arenes prepared in A-150, with the reaction reagents/conditions otherwise being the same.

It is believed that the polarity of the organic solvents may be used to adjust the kinetics of the reaction, resulting in different linear precursor formation during the reflux phase or different crystallization behavior during the cyclization phase (or distillation phase), thereby adjusting the selectivity of the resulting calixarene compounds. For instance, the organic solvents with a higher polarity or nucleophilicity (that is, the ability of the solvent to interact with polar transition states in the polycondensation reaction), such as diphenyl ether, may modify the activity of the nitrogen-containing base catalyst in a way to improve the formation of the amount of the desired linear precursor necessary to form the desired calixarene compounds. This could result in a higher yield and higher selectivity toward cyclic compounds (calixarenes) over linear compounds (linear phenolic resins) in the cyclization phase, compared against the organic solvents with a lower polarity or nucleophilicity (such as xylene or A-150). In one embodiment, tert-amylcalix[8]arenes prepared in diphenylether/xylene mixture has an isolated yield of about 5% higher than the isolated yield of tert-amylcalix[8]arenes prepared in A-150, with the reaction reagents/conditions otherwise being the same.

Additionally, when a high boiling point solvent is used, one or more other organic solvents may be added as an azeo-carrier. For instance, when a high-boiling-point solvent, such as diphenyl ether, is used in the reaction, this solvent alone does not form azeotropes with water due to its high boiling point. When water is produced in the reaction system, it is actually released above its boiling point of 100° C. and, thus, would enter the vapor phase causing significant foaming. Adding an azeo-carrier can mitigate this boil-over issue by forming azeotropes with water and constantly removing water from the reaction mass. Exemplary azeo-carrier solvents are xylene and ethyl acetate. An exemplary organic solvent used in the reaction is a mixture of diphenyl ether with xylene and/or ethyl acetate.

Typically, the calixarene compounds formed have poor solubility at room temperature in a typical hydrocarbon solvent, with some exceptions such as para-nonylcalixarenes and para-dodecylcalixarenes which may be liquid at room temperature. Conventionally, solid calixarene compounds are synthesized under high-dilution conditions, meaning that the reaction of the phenolic compound and the aldehyde are typically conducted in a large amount of an organic solvent (e.g., with the solvent concentration of about 80-85 wt %). A highly diluted system is typically needed for conventional methods to obtain a high amount of solid cyclic compounds (e.g., 17-20% solid contents); otherwise, a significant amount of linear phenolic resins will form.

In the process discussed in this application, however, the reaction can be carried out in a highly concentrated reaction system, yet still result in a significantly improved solid content (i.e., calixarene compounds) in the reaction products. To carry out the reaction in a highly concentrated reaction system, the mass ratio of the phenolic compound to the organic solvent at the starting of the reaction is typically no less than about 0.25:1, for instance, no less than about 0.4:1, no less than about 0.5:1, no less than about 1:1, no less than 1.25:1, or no less than about 1.5:1. Typically, the mass ratio of the phenolic compound to the organic solvent at the starting of the reaction ranges from about 0.5:1 to about 2:1, from about 1:1 to about 2:1, or from about 1.25:1 to about 1.8:1.

When the reaction of the phenolic compounds and the aldehyde undergoes reflux and/or distillation stages, as discussed infra, additional organic solvent may be added to the reaction mass, for instance, after the reflux stage (if the reflux stage is conducted) and/or before the distillation stage. This is typically carried out when the reaction mass contains a high amount of solid content and is relatively viscous for subsequent handling (for instance, the subsequent filtration and washing of the reaction product). The organic solvent added at this stage can be the same as the one initially loaded in the reaction system or a different one.

Even in the scenario when additional organic solvent is added to the reaction mass (e.g., after the reflux stage, if the reflux stage is conducted, and/or before the distillation stage), the total amount of organic solvent in the reaction system during the entire condensation reaction between the phenolic compound and the aldehyde can still be relative small compared to the conventional high-dilution reaction condition. To carry out the entire reaction in a highly concentrated reaction system, the mass ratio of the phenolic compound to the total amount of the organic solvent added during the entire reaction (including the reflux stage, if the reflux stage is conducted, and distillation stage) is typically no less than about 0.25:1, for instance, no less than about 0.3:1, no less than about 0.4:1, no less than about 0.5:1, or no less than about 1:1. Typically, the mass ratio of the phenolic compound to the total amount of the organic solvent added during the entire reaction ranges from about 0.25:1 to about 2:1, or from about 0.3:1 to about 1.5:1.

Reaction Kinetics

To assist the process in forming high yield, high purity, and high selectivity calix[8]arenes, the reaction of the phenolic compounds and the aldehyde may first undergo a reflux stage. The reaction is typically carried out at an elevated temperature. The temperature range at the reflux stage depends on the boiling point of the organic solvents used in the reaction system and their azeotropes with water/aldehyde. For alkanes or ethers such as aromatic hydrocarbons or aromatic ethers, the temperature to reach the reflux stage typically ranges from about 70° C. to about 130° C., for instance, from about 90° C. to about 120° C., or from about 95° C. to about 120° C. For instance, when using an aromatic 150 fluid (i.e., an aromatic hydrocarbon solvent having a main component ranging from 9 to 12 carbon atoms; A-150) or an aromatic ether (such as diphenyl ether) as the organic solvent in the reaction system, the temperature to reach the reflux stage typically ranges from about 95° C. to about 105° C.; when using xylene as the organic solvent in the reaction system, the temperature to reach the reflux stage typically ranges from about 90° C. to about 120° C.

The control of the timing of the initial reflux stage can help improve the yield and selectivity toward the calixarene compound. Typically, the reflux stage lasts for a time period of 10 hours or longer, 12 hours or longer, or 15 hours or longer. In one embodiment, the reaction kinetics of an exemplary calix[8]arene formation indicates that the selective formation of the calixarene compound over the linear phenolic resin or other cyclic byproducts in the distillation phase more likely occurs following the 10-hour, 12-hour, 15-hour, or longer initial reflux stage.

It is possible to reduce the reaction time at the reflux stage, yet still produce a composition having a high yield, high purity, and high selectivity toward calix[8]arenes. For instance, when the heating is conducted in a more rigorous manner to heat the reaction vessel at a temperature that is higher than the temperature needed for reaching a reflux stage, the reaction time at the reflux stage can be reduced significantly. Heating under pressure can achieve the same effect. For instance, when using A-150 as the organic solvent in the reaction system, the temperature needed to reach the reflux stage typically ranges from about 95° C. to about 105° C. However, when the heating is conducted in a more rigorous manner to raise the temperature of the reaction vessel to about 115° C., the reaction time at the reflux stage can be reduced from 10 hours to 5 hours. In one embodiment, a rigorous heating results in the temperature of the reaction vessel about 5 to 20° C. higher or about 10 to 15° C. higher than the temperature needed for reaching a reflux stage. This higher temperature increases the reaction rate and can reduce the reaction time at the reflux stage to about 80%, about 70%, about 60%, about 50%, about 40%, about 30%, or about 25% of the reaction time typically needed for the reflux stage. Accordingly, the reflux time can be reduced to about 4 hours, about 5 hours, about 6 hours, about 7 hours, or about 8 hours.

It is not necessary for the reaction to undergo a reflux stage. For instance, when paraformaldehyde is used in the reaction, the reaction may not undergo a reflux stage. This provides the benefit of a significantly shortened total reaction time, while still affording a high yield, high purity, and high selectivity toward calix[8]arenes.

The reaction may also undergo a distillation stage. If a reflux stage is conducted, the distillation stage is typically after the reflux stage. The reaction mixture may be heated at an elevated temperature of 140° C. to 180° C., for instance, from about 140° C. to about 160° C., or from about 140° C. to about 150° C., to remove water from the reaction mixture.

The longer the distillation stage, generally the higher the selectivity toward the calix[8]arene compound. Typically, the distillation stage lasts for a time period of 4 hours or longer, 5 hours or longer, 6 hours or longer, 7 hours or longer, 8 hours or longer, 9 hours or longer, or 10 hours or longer. In one embodiment, the reaction kinetics of an exemplary calix[8]arene formation indicates the increase of the selectivity toward calix[8]arene over calix[6]arene after 3-6 hours of distillation.

Purification

The process to produce a calix[8]arene compound with a high yield, high purity, and high selectivity can be carried out in a one-step reaction, and in a more efficient process, without utilizing a recrystallization step.

Instead, a high-purity calix[8]arene compound can be achieved by a filtration step. Accordingly, the process further comprises filtrating the reaction product directly and drying the filtrated reaction product, thereby producing a calixarene compound containing a high purity calix[8]arene, for instance, a purity of at least about 90%, at least about 92%, at least about 95%, at least about 98%, or at least about 99%. The purity of the calix[8]arene compound is characterized by HPLC analysis, not accounting for the attached solvent and the unreacted free phenolic monomers.

This process can also produce a calixarene compound with a reduced amount of free phenolic monomers, without utilizing more complicated post-synthesis treatments. For instance, simply washing the crude reaction product with an organic solvent can remove most, if not all, free phenolic monomers. The process can also further comprise the step of filtrating the washed reaction product and drying the filtrated reaction product, thereby producing a calixarene compound with a free phenolic monomer content of about 0.5% or lower, about 0.3% or lower, or about 0.1% or lower.

Another aspect of the invention relates to a process for a high-yield, high solid-content production of a calixarene compound. The process comprises reacting a phenolic compound, an aldehyde, and a base catalyst in the presence of an organic solvent, in a highly concentrated reaction system. The mass ratio of the phenolic compound to the organic solvent in the reaction system (the organic solvent added at the starting of the reaction, or the total amount of organic solvent added during the entire condensation reaction) is no less than about 0.25:1, for instance, no less than about 0.4:1, no less than about 0.5:1, no less than about 1:1, no less than 1.25:1, or no less than 1.5:1. The process produces a calixarene-containing product having at least 30% solids, for instance, at least 35%, at least 40%, at least 45%, at least 50%, at least 55%, at least 60%, or at least 65% solids. The base catalyst used is typically a nitrogen-containing base catalyst.

Also applicable to this aspect of the invention are all the descriptions and all embodiments regarding the phenolic compound, the aldehyde, the nitrogen-containing base catalyst, the organic solvent, and their relative amounts; the reaction kinetics (including the reflux stage and/or distillation stage); and the purification discussed above in the first aspect of the invention relating to the process for preparing a calixarene compound.

Another aspect of the invention relates to a process for the selective synthesis of a calix[8]arene compound. The process comprises reacting a phenolic compound, an aldehyde, and a nitrogen-containing base as a catalyst, in the presence of an organic solvent. Optionally, the reacting step is carried out, under reflux conditions, for a time period of 10 hours or longer, 12 hours or longer, or 15 hours or longer, at a normal reflux temperature range, or for a reduced reflux time if heating is conducted in a more rigorous manner or under pressure, as discussed above in the first aspect of the invention relating to the process for preparing a calixarene compound. When paraformaldehyde is used in the reaction, the reaction may not undergo a reflux stage. The process further comprises heating the reaction mixture at an elevated temperature of about 140° C. to about 180° C. for a time period of 4 hours or longer, for instance, 5 hours or longer, 6 hours or longer, 7 hours or longer, 8 hours or longer, 9 hours or longer, or 10 hours or longer, to remove water from the reaction mixture and selectively produce a calixarene compound containing at least 70% calix[8]arene, for instance, at least about 90%, at least about 92%, at least about 95%, at least about 98%, or at least about 99% of calix[8]arene.

Also applicable to this aspect of the invention are all the descriptions and all embodiments regarding the phenolic compound, the aldehyde, the nitrogen-containing base catalyst, the organic solvent, and their relative amounts; the reaction kinetics (including the reflux stage and/or distillation stage); and the purification discussed above in the first aspect of the invention relating to the process for preparing a calixarene compound.

Another aspect of the invention relates to a process for a one-step, selective synthesis of a high-purity calix[8]arene compound. The process comprises reacting, in a one-step process, a phenolic compound and an aldehyde in the presence of a base catalyst to form a high-purity calix[8]arene compound, without carrying out a recrystallization step. The base catalyst used is typically a nitrogen-containing base catalyst.

The process can further comprise the step of filtrating the reaction product and drying the filtrated reaction product, thereby producing a calix[8]arene compound with a purity of at least about 90%, at least about 92%, at least about 95%, at least about 98%, or at least about 99%.

Also applicable to this aspect of the invention are all the descriptions and all embodiments regarding the phenolic compound, the aldehyde, the nitrogen-containing base catalyst, the organic solvent, and their relative amounts; the reaction kinetics (including the reflux stage and/or distillation stage); and the purification discussed above in the first aspect of the invention relating to the process for preparing a calixarene compound.

Another aspect of the invention relates to a process for the selective synthesis of a calix[8]arene compound with a low free phenolic monomer content. The process comprises the steps of reacting a phenolic compound and an aldehyde in the presence of a base catalyst, and washing the reaction product to remove free phenolic compound monomers, to produce a calix[8]arene compound with a free phenolic monomer content of about 0.5% or lower, for instance, about 0.3% or lower, or about 0.1% or lower. The process does not include a recrystallization step. The base catalyst used is typically a nitrogen-containing base catalyst.

Also applicable to this aspect of the invention are all the descriptions and all embodiments regarding the phenolic compound, the aldehyde, the nitrogen-containing base catalyst, the organic solvent, and their relative amounts; the reaction kinetics (including the reflux stage and/or distillation stage); and the purification discussed above in the first aspect of the invention relating to the process for preparing a calixarene compound.

Other aspects of the invention also relate to a phenolic oligomer composition prepared by any one of the processes discussed above.

In-Situ, One-Pot Process for Preparation of Calix[4]Arenes from Calix[8]Arenes

One aspect of the invention relates to a process for a one-pot synthesis of a high-purity calix[4]arene compound. The process comprises reacting a phenolic compound and an aldehyde in the presence of at least one nitrogen-containing base as a catalyst to form a calix[8]arene compound; and cleaving the calix[8]arene compound into a high-purity calix[4]arene compound, directly, without carrying out a purification step before the cleaving step.

Unlike the conventional process that uses a pre-purified calix[8]arene compound or starts from an alkylphenol and aqueous formaldehyde in a solventless system which initially results in highly voluminous foams and highly viscous and unmanageable residues, the in-situ process described herein provides a one-pot synthesis of a high-purity calix[4]arene compound in a commercial scale without purifying the intermediate calix[8]arene compound and in a technically feasible manner.

The in-situ, one-pot process starts from the preparation of a high-purity calix[8]arene compound, which is used directly for cleaving into calix[4]arene compound, without carrying out a purification step to the in-situ formed calix[8]arene compound. This one-pot process is highly efficient, scalable in an industry production, and economically practical, yet produces calix[4]arene compounds with a high-purity.

The in-situ intermediate, high-purity calix[8]arene compound is formed by reacting a phenolic compound and an aldehyde in the presence of at least one nitrogen-containing base as a catalyst. The reacting step can be carried out in the presence of an organic solvent.

Accordingly, applicable to this aspect of the invention are all the descriptions and all embodiments regarding the phenolic compound, the aldehyde, the nitrogen-containing base catalyst, the organic solvent, and their relative amounts; and the reaction kinetics (including the reflux stage and/or distillation stage) discussed supra in the context of preparation of a high-purity calix[8]arene.

In certain embodiments, the nitrogen-containing base catalyst in the reacting step is a sterically hindered amine (e.g., a sterically hindered primary amine, a sterically hindered secondary amine, or a sterically hindered tertiary amine). Suitable sterically hindered amines and the amounts used are the same as described supra in the context of preparation of a high-purity calix[8]arene.

In one embodiment, the nitrogen-containing base catalyst is an amidine compound having the formula of

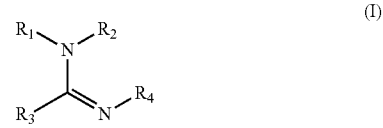

or a guanidine compound having the formula of

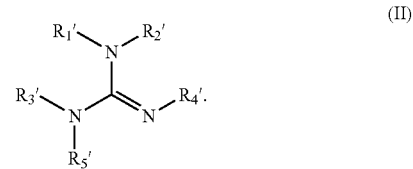

Suitable amidine and guanidine compounds and the amounts used are the same as described supra in the context of preparation of a high-purity calix[8]arene.

In one embodiment, the nitrogen-containing base catalyst is a morpholine compound, an imidazole compound, a pyridine compound, a triamine compound, or an amino-containing ether compound. Suitable morpholine, imidazole, pyridine, triamine, and amino-containing ether compounds and the amounts used are the same as described supra in the context of preparation of a high-purity calix[8]arene.

In certain embodiments, the nitrogen-containing base catalyst is a tetraalkyl ammonium hydroxide. Suitable tetraalkyl ammonium hydroxides and the amounts used are the same as described supra in the context of preparation of a high-purity calix[8]arene.

In certain embodiments, the aldehyde in the reacting step is formaldehyde or paraformaldehyde. Other suitable aldehydes and the amounts used are the same as described supra in the context of preparation of a high-purity calix[8]arene.

In certain embodiments, the phenolic compound in the reacting step is phenol or an alkyl phenol, in particular a para-alkyl phenol (e.g., a para-$C_1$-$C_{24}$ alkyl; linear, branched, or cyclic). In one embodiment, the alkyl group of the alkyl phenol is a tert-$C_4$-$C_{12}$ alkyl (such as tert-$C_4$-$C_8$ alkyl). For instance, the alkyl group of the alkyl phenol is a para-tert-butyl, para-tert-amyl, or para-tert-octyl; resulting in a calix[4]arene compound of para-tert-butylcalix[4]arene, para-tert-amyl calix[4]arene, or para-tert-octyl calix[4]arene, respectively.

In certain embodiments, the phenolic compound in the reacting step is an arylalkyl phenol, in particular a para-arylalkyl phenol (e.g., a para-benzyl phenol or para-cumyl-phenol).

In certain embodiments, the reacting step is carried out in the presence of an organic solvent. Suitable organic solvents used in the reacting step include an aromatic hydrocarbon or a mixture containing thereof, for instance, the organic solvent may be an aromatic hydrocarbon having 7 to 12 carbon atoms, or a mixture containing thereof. In one embodiment, the organic solvent is an aromatic hydrocarbon having 9 to 12 carbon atoms, or a mixture containing thereof.

Alternatively, the organic solvent used in the reacting step may be a straight-chain hydrocarbon having 11 to 20 carbon atoms, or a mixture containing thereof. For instance, the organic solvent used is hexadecane, or a mixture containing thereof.

Alternatively, the organic solvent used in the reacting step may be an ether, or a mixture containing thereof. Exemplary ether include aromatic ethers such as diphenyl ether, and glycol ethers, such as diethylene glycol dibutyl ether. Suitable organic solvents also include a mixture of solvents containing ethers, e.g., Dowtherm A (a mixture of diphenylether and biphenyl).

Other suitable organic solvents and the amounts used are the same as described supra in the context of preparation of a high-purity calix[8]arene. Suitable organic solvents also include the combination of one or more different organic solvents described herein.

Any of the embodiments described supra regarding the reaction conditions in the context of preparation of a high-purity calix[8]arene is applicable to the reacting step in this aspect of the invention for the in-situ preparation of a calix[8]arene. For instance, the reaction between the phenolic compound and the aldehyde can be carried out in the presence of an organic solvent. Optionally, the reacting step is carried out under reflux conditions, optionally for a time period of 10 hours or longer, at a normal reflux temperature range, or for a reduced reflux time if heating is conducted in a more rigorous manner or under pressure, as discussed above in the first aspect of the invention relating to the process for preparing a calixarene compound. When paraformaldehyde is used in the reaction, the reaction may not undergo a reflux stage. The reacting step may further comprise heating the reaction mixture at an elevated temperature of about 140° C. to about 180° C., optionally for a time period of 4 hours or longer, to remove water from the reaction mixture and selectively produce a calix[8]arene compound of at least 70% purity. As discussed above, depending on the reaction conditions used, the calix[8]arene compound produced in-situ can have a high-purity, for instance, a purity of at least about 90%, at least about 92%, at least about 95%, at least about 98%, or at least about 99%.

Because the calix[8]arene compound is produced with a high yield, high purity, and high selectivity, the crude calix[8]arene compound from the reacting step is used directly for cleaving into a calix[4]arene compound, without carrying out a purification step to the in-situ formed calix[8]arene compound, such as recrystallization or filtration. Because no further purification is carried out prior to the cleaving step, the in-situ system may contain residual organic solvent, if used in the reaction step.

The in-situ prepared crude, high-purity calix[8]arene compound is then cleaved into a high-purity calix[4]arene compound.

The cleaving step typically comprises heating the in-situ prepared calix[8]arene compound to a temperature of at least about 200° C., for instance, at least about 205° C., at least about 210° C., at least about 215° C., at least about 220° C., at least about 225° C., at least about 230° C., at least about 235° C., at least about 240° C., at least about 245° C., at least about 250° C., at least about 255° C., or from about 250° C. to about 260° C., to form the calix[4]arene compound. The temperature range at the cleaving step can depend on the boiling point of the organic solvents, if present in the in-situ system. The temperature is typically elevated gradually to the target temperature.

Once the temperature reaches the target temperature, the heating generally lasts for a time period of about 10 minutes or longer, about 15 minutes or longer, about 30 minutes or longer, about 1 hour or longer, about 2 hours or longer, about 3 hours or longer, about 4 hours or longer, about 5 hours or longer, or about 6 hours or longer.

Additional organic solvent(s), different from the organic solvent(s) used in the in-situ reaction may be added during and/or prior to the cleaving step, before the heating. For instance, when a high-boiling-point solvent, such as diphenyl ether, is used in the in-situ reaction, one or more other organic solvents may be added as an azeo-carrier. For instance, when diphenyl ether is used in the in-situ reaction, a xylene solvent or combination of xylene and ethyl acetate solvents can be added to control the water removal by forming azeotropes with water and avoiding boilovers. Diphenyl ether alone does not form azeotropes with water due to its high boiling point. When water is produced in the reaction system, it is actually released above its boiling point of 100° C. and, thus, would enter the vapor phase causing significant foaming if it was not addressed by an azeo-carrier.

The cleaving step is typically carried out in the presence of a metal hydroxide catalyst, such as an alkali metal hydroxide (e.g., sodium hydroxide, potassium hydroxide, lithium hydroxide, rubidium hydroxide, or caesium hydroxide) or an alkaline earth metal hydroxide (e.g., calcium hydroxide, strontium hydroxide, or barium hydroxide).

In one embodiment, the cleaving step comprises heating the calix[8]arene compound at a temperature ranging from about 250 to about 260° C., in the presence of an alkali metal hydroxide catalyst, optionally for a period of 30 minutes or longer.

The molar ratio of the metal hydroxide catalyst relative to the calix[8]arene compound (assuming all the starting phenolic compound has converted to the calix[8]arene compound) typically ranges from about 1:200 to about 1:1, for instance, from about 1:100 to about 1:1, from about 1:50 to about 1:1, from about 1:20 to about 1:2, or from about 1:10 to about 1:2.5.

Once the calix[4]arene compound is formed in the in-situ system, a high-purity calix[4]arene compound can be precipitated out of the reaction solution by lowering the temperature. This is because, in general, calix[4]arene compounds, such as para-tert-alkylcalix[4]arenes, have poor solubility in the typical organic solvents used in the in-situ reaction. Typically, the temperature can be lowered to below 100° C., or about room temperature to precipitate the solid calix[4]arene compound.

An antisolvent can be added to facilitate the precipitation of the calix[4]arene compounds with a high purity. The antisolvent is selected so that the resulting calix[4]arene compound is poorly soluble in, or has less solubility in compared to, the organic solvent used in the in-situ reaction. Suitable antisolvents are polar solvents such as an ester (e.g., methyl acetate, ethyl acetate, or butyl acetate), ketone (e.g., acetone, methyl ethyl ketone, methyl isobutyl ketone, or cyclohexanone), nitrile (e.g., acetonitrile, propionitrile, butyronitrile, or benzonitrile,), or alcohol (e.g., methanol, ethanol, isopropanol, isopentanol, or cyclohexanol).

After the calix[4]arene compound precipitates out of the reaction solution as a solid, a high-purity calix[4]arene compound can be isolated by a filtration step. Accordingly, the process further comprises filtrating the precipitated calix[4]arene compound directly and drying the filtrated calix[4]arene compound, thereby producing a high purity calix[4]arene compound.

The calix[4]arene compounds produced from the in-situ, one-pot process can have a high purity, for instance, a purity of at least about 90%, at least about 91%, at least about 92%, at least about 93%, at least about 94%, at least about 95%, at least about 96%, at least about 97%, at least about 98%, at least about 99%, or at least about 99.5%. The purity of the calix[4]arene compound is characterized by HPLC analysis, not accounting for the attached solvent and/or the unreacted free phenolic monomers.

Another aspect of the invention relates to a process for a one-pot synthesis of a high-purity calix[4]arene compound comprising 4 units of formula (A-1):

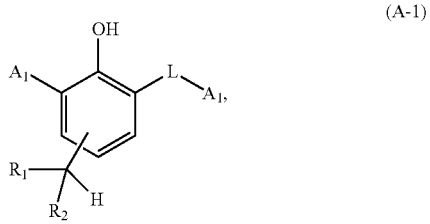

wherein:
each of $R_1$ and $R_2$ is independently linear, branched, or cyclic $C_1$-$C_{30}$ alkyl, aryl, alkylaryl, or arylalkyl;
each L is independently selected from the group consisting of —$CH_2$—, —$C(O)$—, —$CH(R_3)$—, —$(CH_2)_{n'}$—O—$(CH_2)_{n'}$—, —$C(R_3)_2$—;
each $R_3$ is independently a $C_1$-$C_6$ alkyl;
each n' is independently an integer from 1-2;
each $A_1$ represents a direct covalent bond to an adjacent unit of formula (A-1) such that there is one L group between adjacent units, whereby the total units in the calixarene compound form a ring.

The process comprises reacting a phenolic compound having a formula of

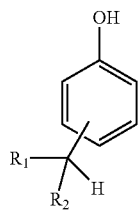

and an aldehyde in the presence of at least one nitrogen-containing base as a catalyst to form a calix[8]arene compound having 8 units of formula (A-1); and cleaving the calix[8]arene compound into the high-purity calix[4]arene compound, directly, without carrying out a purification step before the cleaving step.

Applicable to this aspect of the invention are all the descriptions and all embodiments regarding the phenolic compound, the aldehyde, the nitrogen-containing base catalyst, the organic solvent, and their relative amounts; and the reaction kinetics (including the reflux stage and distillation stage) discussed supra in the context of preparation of a high-purity calix[8]arene.

Also applicable to this aspect of the invention are all the descriptions and all embodiments regarding Formula (A-1), and the definitions of the variables $A_1$, L, $R_1$, and $R_2$ discussed supra in the embodiments relating to the calixarene compound comprising phenolic monomers of Formula (A-1).

Also applicable to this aspect of the invention are all the descriptions and all embodiments regarding the in-situ, one-pot process, including the reaction conditions (temperature, time, catalyst, and organic solvent) for the reacting step between the phenolic compound and aldehyde and the reaction conditions for the cleaving step (temperature, time, catalyst, organic solvent, and amounts of the catalyst), discussed supra in the aspect of the invention relating to the one-pot synthesis of a high-purity calix[4]arene compound.

In certain embodiments, the substituent group

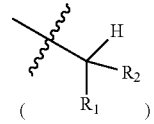

on the calixarene compound of Formula (A-1) is at the para position to the hydroxyl group. In one embodiment, each $R_1$ is methyl, and each $R_2$ is methyl, ethyl, propyl, or hexyl.

The inventors have surprisingly discovered that the calix[4]arene compound having formula (A-1), i.e., a sec-alkylcalix[4]arene, has an unexpectedly high solubility in a hydrocarbon solvent, as compared to, for instance, tert-alkylcalix[4]arenes. A typical calixarene compound, such as tert-butylcalix[4]arene, is usually only soluble in particular solvents such as chloroform and pyridine at room temperature, whereas the solubility in hydrocarbon solvents is usually poor. Thus, further utilization of the calixarene compounds is limited. The improved solubility greatly increases the scope and ease of the application of the alkylcalix[4]arene compounds.

The solubility of a calixarene compound in a solvent can be characterized by the concentration of the calixarene compound in the solvent at certain dissolution temperatures. For instance, the solubility of sec-butylcalix[4]arene in toluene at room temperature (e.g., about 21° C.) is 13.7 wt % (see, for instance, FIG. 4).

The sec-alkylcalix[4]arene is typically at least partially soluble in an organic solvent typically used in the in-situ reaction. The term "partially soluble" is used to refer to the situation where there is certain concentration of soluble calix[4]arene compound in the solvent at room temperature, for instance, the concentration is at least 1%, at least 2%, at least 3%, at least 4%, at least 5%, at least 7%, at least 10%, at least 12%, at least 13%, at least 15%, at least 17%, or at least 20%.

The sec-alkylcalix[4]arene can have a solubility increase in a hydrocarbon solvent at room temperature, compared to the corresponding tert-alkylcalix[4]arene (i.e., the tert-alkyl substituent on the tert-alkylcalix[4]arene has the same number of carbon atoms as the sec-alkyl substituent on the sec-alkylcalix[4]arene), of at least about 1%, at least about 2%, at least about 3%, at least about 4%, at least about 5%, at least about 7%, at least about 10%, at least about 12%, at least about 13%, at least about 15%, at least about 17%, or at least about 20%.

Figure 5:
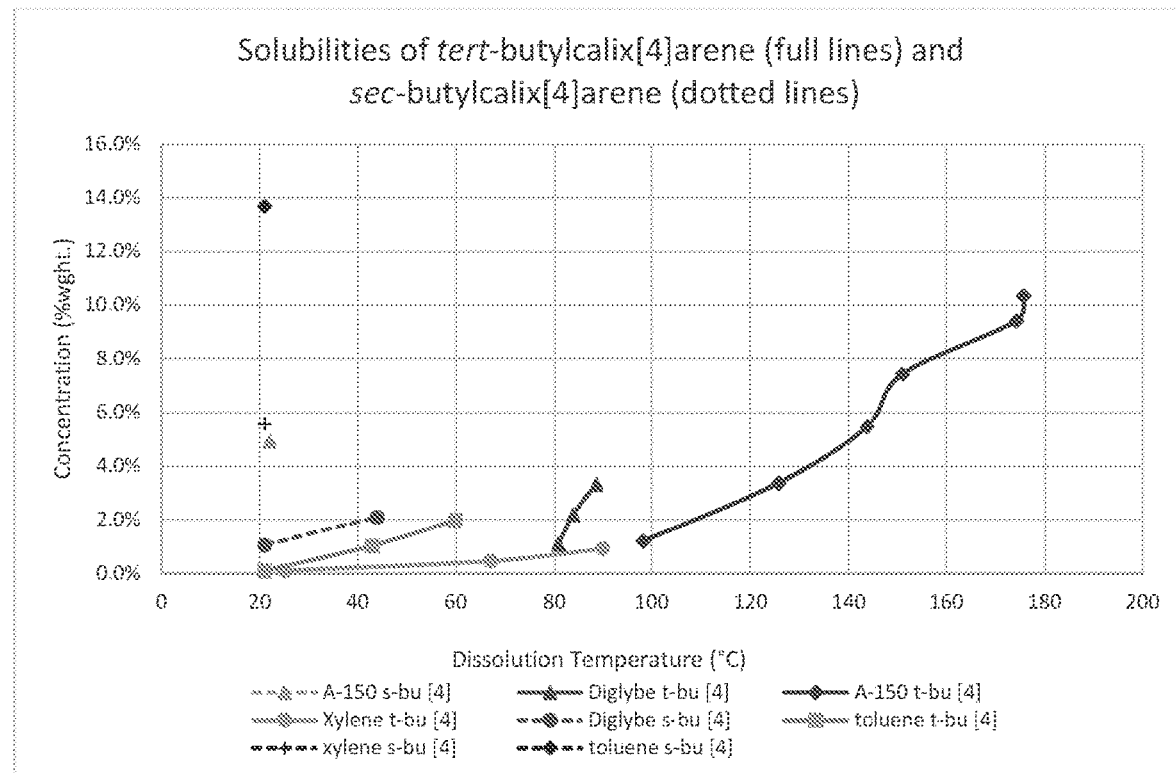
FIG. 5 compares the solubility of sec-butylcalix[4]arene in various organic solvents, at various dissolution temperatures, against the solubility of tert-butylcalix[4]arene. "Diglybe" refers to diethylene glycol dibutyl ether"; "t-bu [4]" refers to tert-butylcalix[4]arene; and "s-bu [4]" refers to sec-butylcalix[4]arene.

As shown in FIG. 5, in a typical hydrocarbon solvent, xylene, tert-butylcalix[4]arene is insoluble at room temperature (solubility is about 0% or 0.1%), whereas at room temperature, sec-butylcalix[4]arene has a solubility of at least 5% in xylene. Accordingly, sec-butylcalix[4]arene has a solubility increase of at least 5% in xylene at room temperature, compared to that of tert-butylcalix[4]arene. FIG. 5 also shows that in another typical hydrocarbon solvent, toluene, tert-butylcalix[4]arene is insoluble at room temperature (solubility is about 0% or 0.1%), whereas at room temperature, sec-butylcalix[4]arene has a solubility of at least 13% in toluene. Accordingly, sec-butylcalix[4]arene has a solubility increase of at least 13% in toluene at room temperature, compared to that of tert-butylcalix[4]arene.

In some embodiments, the sec-alkylcalix[4]arene is at least partially soluble in a hydrocarbon solvent. The hydrocarbon solvent can be an aliphatic solvent including alkanes (such as alkanes having 4 to 24 carbon atoms; e.g., alkanes having 5 to 16 carbon atoms) or an aromatic solvent (such as alkyl benzenes or naphthalenes; e.g., an aromatic hydrocarbon solvent containing 7 to 12 carbon atoms). Exemplary solvents that the sec-alkylcalix[4]arene has a high solubility in are hexane, xylene, toluene, A-150 solvent.

As discussed above, the calixarene compounds prepared herein can exist in one or more stereoisomeric forms, for instance, when prepared using a starting phenolic compound with a chiral center. The resulting calixarene compounds may be a mixture of diastereomers in which the stereoisomeric forms may not be easy to be separated. The formation of such a mixture of diastereomeric forms may result in an increased solubility of the calixarene compound in a hydrocarbon solvent.

In one embodiment, the cleaving step comprises heating the calix[8]arene compound at a temperature of at least about 200° C., for instance, at least about 205° C., at least about 210° C., at least about 215° C., at least about 220° C., at least about 225° C., at least about 230° C., at least about 235° C., at least about 240° C., at least about 245° C., at least about 250° C., at least about 255° C., or from about 250 to about 260° C., in the presence of an alkali metal hydroxide catalyst, optionally for a period of 30 minutes or longer.

As discussed above, once the calix[4]arene compound is formed in the in-situ system, a high-purity calix[4]arene compound can be precipitated out of the reaction solution by lowering the temperature, for instance, to below 100° C., or about room temperature.

However, because the high solubility of the sec-alkylcalix[4]arene in a typical organic solvent used in the in-situ reaction system, the sec-alkylcalix[4]arene is typically precipitated out of the reaction solution by using a specific type of antisolvent that the sec-alkylcalix[4]arene has a poor solubility in, or has less solubility in compared to the organic solvent used in the in-situ reaction. Exemplary antisolvents are acetone and isopropanol.

The process may further comprise, prior to adding the antisolvent, adding an acid to the in-situ reaction solution to neutralize the metal hydroxide catalyst. The resulting metal salts may be removed by filtration. The process may further comprise a distillation stage to remove, at least partially, the organic solvent used in the in-situ reaction.

After the calix[4]arene compound precipitates out of the reaction solution as a solid, a high-purity calix[4]arene compound can be isolated by a filtration step. Accordingly, the process further comprises filtrating the precipitated calix[4]arene compound directly, optionally washing the filtrated calix[4]arene compound, and drying the filtrated calix[4]arene compound, thereby producing a high purity calix[4]arene compound.

The calix[4]arene compounds produced from the in-situ, one-pot process can have a high purity, for instance, a purity of at least about 90%, at least about 92%, at least about 93%, at least about 94%, at least about 95%, at least about 96%, at least about 97%, at least about 98%, at least about 99%, or at least about 99.5%. The purity of the calix[4]arene compound is characterized by HPLC analysis, not accounting for the attached solvent and/or the unreacted free phenolic monomers.

Improved Conversion of Calix[8]Arenes to Calix[4]Arenes

Another aspect of the invention relates to a process for improved conversion of a calix[8]arene compound to a calix[4]arene compound. The process comprises providing a calix[8]arene compound; and cleaving the calix[8]arene compound in a glycol ether solvent having a boiling point of at least about 200° C., to result in a high-purity calix[4]arene compound, without using an antisolvent.

The calix[8]arene compound used in this aspect of the invention may be prepared by an alkali base catalyst such as sodium hydroxide or potassium hydroxide, using methods known to one skilled in the art. The crude calix[8]arene compound prepared by a conventional method may be low in yield and purity, but may be further purified, such as by recrystallization, to obtain a high-purity calix[8]arene compound prior to the cleaving step.

Alternatively, a high-purity calix[8]arene compound may be prepared by using the nitrogen-containing base catalyst according to this invention. Accordingly, applicable to this aspect of the invention are all the descriptions and all embodiments regarding the phenolic compound, the aldehyde, the nitrogen-containing base catalyst, the organic solvent, and their relative amounts; and the reaction kinetics (including the reflux stage and distillation stage) discussed supra in the context of preparation of a high-purity calix[8]arene.

Also applicable to this aspect of the invention are all the descriptions and all embodiments regarding the reaction conditions for the cleaving step (temperature, time, catalyst, and amounts of the catalyst), discussed supra in the aspects of the invention relating to the one-pot synthesis of a high-purity calix[4]arene compound.

Typically, to facilitate the precipitation of a high-purity calix[4]arene compound, an antisolvent is used after the calix[4]arene compound is formed. The inventors have discovered that, when a selected solvent is used in the cleaving step, the formed calix[4]arene compound can precipitate directly from the reaction solution, without adding an antisolvent. Because this additional step is eliminated, this process allows for a high efficiency production of a calix[4]arene compound, yet with a high-purity.

The term "glycol ether" generally refers to an alkylene glycol alkyl/aryl ether, including but not limited to, a monoalkylene glycol monophenyl ether (e.g., ethylene glycol monophenyl ether), dialkylene glycol monoalkyl ether (e.g., diethylene glycol monobutyl ether), dialkylene glycol dialkyl ether (e.g., diethylene glycol dibutyl ether), trialkylene glycol monoalkyl ether (e.g., triethylene glycol monoethyl ether), and trialkylene glycol dialkyl ether. In one embodiment, the glycol ether solvent is diethylene glycol dibutyl ether.

The solvent used in the cleaving step is a glycol ether solvent having a boiling point of at least about 200° C., for instance, a boiling point of at least about 205° C., at least about 210° C., at least about 215° C., at least about 220° C., at least about 225° C., at least about 230° C., at least about 235° C., at least about 240° C., at least about 245° C., at least about 250° C., at least about 255° C., or from about 250 to about 260° C.

Once the calix[4]arene compound is formed from the cleaving step, a high-purity calix[4]arene compound can be precipitated out of the reaction solution, directly, by lowering the temperature, without using an antisolvent, due to the poor solubility of the calix[4]arene compound in the specifically selected solvents used in the cleaving step. Typically, the temperature can be lowered to below 100° C., or about room temperature to precipitate the solid calix[4]arene compounds.

In certain embodiments, the cleaving step comprises heating the calix[8]arene compound at a temperature of at least about 200° C., in the presence of a metal hydroxide catalyst. In one embodiment, the cleaving step comprises heating the calix[8]arene compound at a temperature ranging from about 250 to about 260° C., in the presence of an alkali metal hydroxide catalyst, for a period of about 10 minutes or longer, about 15 minutes or longer, about 30 minutes or longer, about 1 hour or longer, about 2 hours or longer, about 3 hours or longer, about 4 hours or longer, or about 5 hours or longer; and lowering the temperature to precipitate a high-purity calix[4]arene compound.

After the calix[4]arene compound precipitates out of the reaction solution as a solid, a high-purity calix[4]arene compound can be isolated by a filtration step. Accordingly, the process further comprises filtrating the precipitated calix[4]arene compound directly and drying the filtrated calix[4]arene compound, thereby producing a high purity calix[4]arene compound.

The calix[4]arene compounds produced from the this process can have a high purity, for instance, a purity of at least about 90%, at least about 92%, at least about 93%, at least about 94%, at least about 95%, at least about 96%, at least about 97%, at least about 98%, at least about 99%, or at least about 99.5%. The purity of the calix[4]arene compound is characterized by HPLC analysis, not accounting for the attached solvent and/or the unreacted free phenolic monomers.

In certain embodiments, the calix[4]arene compound is a phenolcalix[4]arene (i.e., having a monomeric unit of phenol) or an alkylcalix[4]arene (i.e., having a monomeric unit of an alkyl phenol), in particular a para-alkylcalix[4]arene (e.g., the alkyl group is a para-$C_1$-$C_{24}$ alkyl; linear, branched, or cyclic). In one embodiment, the alkyl group of the alkylcalix[4]arene is a tert-$C_4$-$C_{12}$ alkyl (such as tert-$C_4$-$C_8$ alkyl). For instance, the calix[4]arene compound is a para-tert-butylcalix[4]arene, para-tert-amylcalix[4]arene, or para-tert-octylcalix[4]arene.

In certain embodiments, the calix[4]arene compound is an arylalkylcalix[4]arene (i.e., having a monomeric unit of an arylalkyl phenol), in particular a para-arylalkylcalix[4]arene (e.g., the arylalkyl group is a para-benzyl or para-cumyl).

Yet another aspect of the invention relates to a process for improved conversion of a calix[8]arene compound to a calix[4]arene compound. The process comprises providing a calix[8]arene compound comprising 8 units of formula (A-1); and cleaving the calix[8]arene compound in an organic solvent having a boiling point of at least about 220° C., to result in a high-purity calix[4]arene compound, without using an antisolvent. Formula (A-1) is represented below:

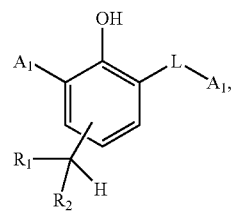

(A-1)

wherein:
each of $R_1$ and $R_2$ is independently linear, branched, or cyclic $C_1$-$C_{30}$ alkyl, aryl, alkylaryl, or arylalkyl;
each L is independently selected from the group consisting of —$CH_2$—, —$C(O)$—, —$CH(R_3)$—, —$(CH_2)_{n'}$—O—$(CH_2)_{n'}$—, —$C(R_3)_2$—;
each $R_3$ is independently a $C_1$-$C_6$ alkyl;
each n' is independently an integer from 1-2;
each $A_1$ represents a direct covalent bond to an adjacent unit of formula (A-1) such that there is one L group between adjacent units, whereby the total units in the calixarene compound form a ring.

A high-purity calix[8]arene compound comprising 8 units of formula (A-1) may be prepared by using the nitrogen-containing base catalyst according to this invention. Accordingly, applicable to this aspect of the invention are all the descriptions and all embodiments regarding the phenolic compound, the aldehyde, the nitrogen-containing base catalyst, the organic solvent, and their relative amounts; and the reaction kinetics (including the reflux stage and distillation stage) discussed supra in the context of preparation of a high-purity calix[8]arene.

Also applicable to this aspect of the invention are all the descriptions and all embodiments regarding Formula (A-1), and the definitions of the variables $A_1$, L, $R_1$, and $R_2$ discussed supra in the embodiments relating to the calixarene compound comprising phenolic monomers of Formula (A-1).

Also applicable to this aspect of the invention are all the descriptions and all embodiments regarding the reaction conditions for the cleaving step (temperature, time, catalyst, and amounts of the catalyst), discussed supra in the aspects of the invention relating to the one-pot synthesis of a high-purity calix[4]arene compound.

The solvent used in the cleaving step is selected so that the resulting high-purity calix[4]arene compound can precipitate directly from the reaction solution, without adding an antisolvent.

The solvent used in the cleaving step is an organic solvent having a boiling point of at least about 200° C., for instance, a boiling point of at least about 205° C., at least about 210° C., at least about 215° C., at least about 220° C., at least about 225° C., at least about 230° C., at least about 235° C., at least about 240° C., at least about 245° C., at least about 250° C., at least about 255° C., or about 250 to about 260° C. In certain embodiments, the organic solvent is a glycol ether solvent having a boiling point of at least about 200° C., for instance, a boiling point of at least about 205° C., at least about 210° C., at least about 215° C., at least about 220° C., at least about 225° C., at least about 230° C., at least about 235° C., at least about 240° C., at least about 245° C., at least about 250° C., at least about 255° C., or about 250 to about 260° C. Suitable glycol ether solvents are the same as described supra in the aspect of the invention relating to a process for improved conversion of a calix[8]arene compound to a calix[4]arene compound.

In certain embodiments, the cleaving step comprises heating the calix[8]arene compound at a temperature of at least about 200° C., in the presence of a metal hydroxide catalyst. In one embodiment, the cleaving step comprises heating the calix[8]arene compound at a temperature ranging from about 250 to about 260° C., in the presence of an alkali metal hydroxide catalyst, for a period of about 10 minutes or longer, about 15 minutes or longer, about 30 minutes or longer, about 1 hour or longer, about 2 hours or longer, or about 5 hours or longer; and lowering the temperature to precipitate a high-purity calix[4]arene compound.

After the calix[4]arene compound precipitates out of the reaction solution as a solid, a high-purity calix[4]arene compound can be isolated by a filtration step. Accordingly, the process further comprises filtrating the precipitated calix[4]arene compound directly and drying the filtrated calix[4]arene compound, thereby producing a high purity calix[4]arene compound.

The calix[4]arene compounds produced from this process can have a high purity, for instance, a purity of at least about 90%, at least about 92%, at least about 93%, at least about 94%, at least about 95%, at least about 96%, at least about 97%, at least about 98%, at least about 99%, or at least about 99.5%. The purity of the calix[4]arene compound is characterized by HPLC analysis, not accounting for the attached solvent and/or the unreacted free phenolic monomers.

In certain embodiments, the substituent group

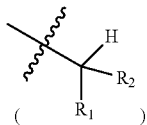

on the calixarene compound of Formula (A-1) is at the para position to the hydroxyl group. In one embodiment, each $R_1$ is methyl, and each $R_2$ is methyl, ethyl, propyl, or hexyl.

Applications

The calixarene compounds or phenolic oligomer compositions prepared by the processes disclosed herein can be used in a wide range of applications.

One aspect of the invention relates to a demulsifier or dehazer composition comprising the calixarene compounds or phenolic oligomer compositions prepared by the processes discussed above. The demulsifier or dehazer composition may further comprise one or more other components commonly used in a demulsifier or dehazer composition, as understood by those of skill in the art. The demulsifier or dehazer composition may be used for a wide variety of applications for oil and water separation, such as refinery and fuel dehazing. The demulsifier or dehazer composition may further act as salt-sequestering agents in crude oil, for instance, to sequester salt from crude oil and as a result, reduce salt levels in crude oil.

The calixarene compounds or phenolic oligomer compositions prepared by the processes disclosed herein may also be used as the starting material for overbasing. For instance, calixarene compounds or phenolic oligomer compositions or their functional derivatives can be attached with metal base moieties forming an overbased metal salt, to neutralize the acidic materials and disperse sludge in lubricating oil compositions or fuel compositions. See, e.g., salicyclic calixarenes and their use as lubricant additives, described in U.S. Pat. No. 6,200,936, which is incorporated herein by reference in its entirety, to the extent not inconsistent with the subject matter of this disclosure. As another example, an additive package based on overbased calixarene compounds or phenolic oligomer compositions prepared by the processes disclosed herein, e.g., a p-didecylcalixarene compound (such as p-dodecylcalix[5,6,8]arene compounds), can perform well in the TEOST HMT test (Thermo-Oxidation Engine Oil Simulation Test), which is employed to evaluate the ability of an engine oil to control the formation of deposits at high temperatures. See, e.g., salicyclic calixarenes and their use as lubricant additives, described in a doctoral thesis by Alessandro Burlini, entitled "SYNTHESIS OF NEW CALIXARENE-BASED LUBRICANT ADDITIVES," published by University of Parma, Department of Chemistry (Italy) on Mar. 18, 2016, which is incorporated herein by reference in its entirety, to the extent not inconsistent with the subject matter of this disclosure.

Another aspect of the invention relates to a paraffin-containing fluid composition comprising a resin containing the calixarene compounds or phenolic oligomer compositions prepared by the processes discussed above, and one or more paraffin-containing fluids. The resin is at least partially soluble in the paraffin-containing fluid, and disperses the paraffin in the fluid composition and/or inhibits the deposition of the paraffin crystals. The fluid can be any hydrocarbon fluid in the oilfield including, but not limited to, a crude oil, home heating oil, lubricating oil (such as an engine oil), and natural gas. These oilfield hydrocarbon fluids typically contain paraffin or paraffin wax. The composition containing the calixarene compounds or phenolic oligomer compositions prepared by the processes may be used for a wide variety of applications to disperse paraffin crystals and/or inhibit paraffin crystal deposition, such as for treating a well or vessel surface to reduce the deposition of paraffin crystals on the well or vessel surface. Additional details on the methods of using calixarene compounds in inhibiting paraffin crystal deposition may be found in U.S. patent application Ser. No. 15/879,293 to Cable, entitled "Paraffin inhibition by solubilized calixarenes," filed on Jan. 24, 2018, which is incorporated herein by reference in its entirety, to the extent not inconsistent with the subject matter of this disclosure.

The calixarene compounds or phenolic oligomer composition prepared by the processes disclosed herein may be used as various other agents or intermediates to prepare other useful agents.

For instance, the calixarene compounds or phenolic oligomer compositions prepared by the processes disclosed here may be used as charge control agents to create a desired charge level and polarity, which may be useful as coating additives that can be applied to surfaces (e.g., aluminum oil cans), as chemical sensors for determining onset of rusting in applications such as marine coatings or aerospace applications, or in toners for developing electrostatic images used for electrophotography, electrostatic recording, electrostatic printing, etc.

The calixarene compounds or phenolic oligomer composition prepared by the processes disclosed here may be used as host molecules, to form a complex or an association with one or more guest molecules, such as ions, metals, organic compounds of various sizes, compounds carrying charges, and salts. By doing so, they may aid in compound delivery (e.g., drug-delivery vehicles) by encapsulating a compound within the cavity of the calixarene compound, thereby aiding in the solubilization of the guest molecule. Or they may be used as extractants to extract small molecules or metal ions (e.g., via chelation or complexation), useful in, for instance, the declassification of nuclear waste, or act as ionophores to transport the metal ions across cell membranes. These technologies are further illustrated in U.S. Pat. No. 7,524,469, and U.S. Patent Application Publication No. 2012/0145542; both of which are hereby incorporated by reference in their entirety, to the extent not inconsistent with the subject matter of this disclosure.

The calixarene compounds or phenolic oligomer compositions prepared by the processes disclosed here may be used as adhesion promoters to accelerate polymerization of monomers in an adhesive composition. This technology is further illustrated in Gutsche, "Calixarenes, An Introduction," page 236 ($2^{nd}$ Edition, RSC Publishing, Cambridge, UK) (2008), which is hereby incorporated by reference in its entirety, to the extent not inconsistent with the subject matter of this disclosure.

The calixarene compounds or phenolic oligomer composition prepared by the processes disclosed here may be used as positive or negative resists, for pattern formation and etching to form a hyperfine structure. The resulting resists can be used to fabricate printed circuit boards, sand carving, microelectronics, and patterning and etching of substrates.

The calixarene compounds or phenolic oligomer composition prepared by the processes disclosed here may be used as catalysts for a variety of chemical reactions. For example, because of their unique topology, complexes in which a calixarene ligand coordinates to a transition metal are potentially valuable for olefin polymerization. This technology is further illustrated in U.S. Pat. No. 6,984,599, which is hereby incorporated by reference in its entirety, to the extent not inconsistent with the subject matter of this disclosure.

The calixarene compounds or phenolic oligomer composition prepared by the processes disclosed here may be used as antifoulants that may be applied to surfaces that normally undergo biofouling (e.g., ship hulls), to inhibit biofouling, or disperse preexisting biofouling.

The calixarene compounds or phenolic oligomer composition prepared by the processes disclosed here may be used as thermal stabilizers, for instance, as curing agents, to aid in cross-linking in the curing processes of polymers.

Additionally, the calixarene compounds or phenolic oligomer composition prepared by the processes disclosed here can be used in any other applications involving the use of a calixarene compound, such as accelerators, additives, binding agents, stabilizing agents, flame retardants (in which the calixarene compounds or phenolic oligomer composition prepared by the processes disclosed here can be a host compound in a flame retardant composition; see, e.g., WO 2017/087115, which is incorporated herein by reference in its entirety, to the extent not inconsistent with the subject matter of this disclosure), adsorbent/absorbant materials, sequestering agents, hardeners, API-transportation, etc.

The calixarene compounds or phenolic oligomer compositions prepared by the processes disclosed here may be further de-alkylated via sulfonation by sulfuric acid or via nitration by nitric acid, using the methods described in U.S. Pat. Nos. 5,952,526 and 2,868,844; which are incorporated herein by reference in their entirety. The sulfonated or nitrated calixarenes are typically soluble and may be used for various applications as described herein.

The calixarene compounds or phenolic oligomer compositions prepared by the processes disclosed here may be used as tackifier resins in a rubber compound for tire applications. For instance, the calixarene compounds or phenolic oligomer compositions or their functional derivatives may be incorporated into rubber compounds as a phenolic tackifier resin or a part of a phenolic tackifier resin to increase the adhesion strength between a fabric or metal wire with the rubber compound.

The calixarene compounds or phenolic oligomer compositions prepared by the processes disclosed here may be further treated or reacted with another polymer component to for form a radial polymer, using the methods described in, e.g., U.S. Patent Application Publication No. 2017/0051224, which is incorporated herein by reference in its entirety. The resulting calixarene-based radial polymer can be used as viscosity index improver additives in lubricant compositions.

Additional aspects, advantages and features of the invention are set forth in this specification, and in part will become apparent to those skilled in the art on examination of the following, or may be learned by practice of the invention. The inventions disclosed in this application are not limited to any particular set of or combination of aspects, advantages and features. It is contemplated that various combinations of the stated aspects, advantages and features make up the inventions disclosed in this application.

EXAMPLES

The following examples are given as particular embodiments of the invention and to demonstrate the practice and advantages thereof. It is to be understood that the examples are given by way of illustration and are not intended to limit the specification or the claims that follow in any manner.

Example 1. Synthesis of Tert-Butylcalix[8]Arenes Using 1,8-Diazabicyclo[5.4.0]Undec-7-Ene (DBU) as the Catalyst

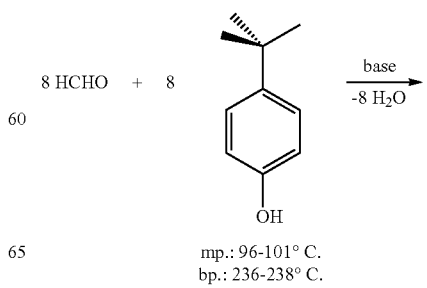

mp.: 96-101° C.
bp.: 236-238° C.

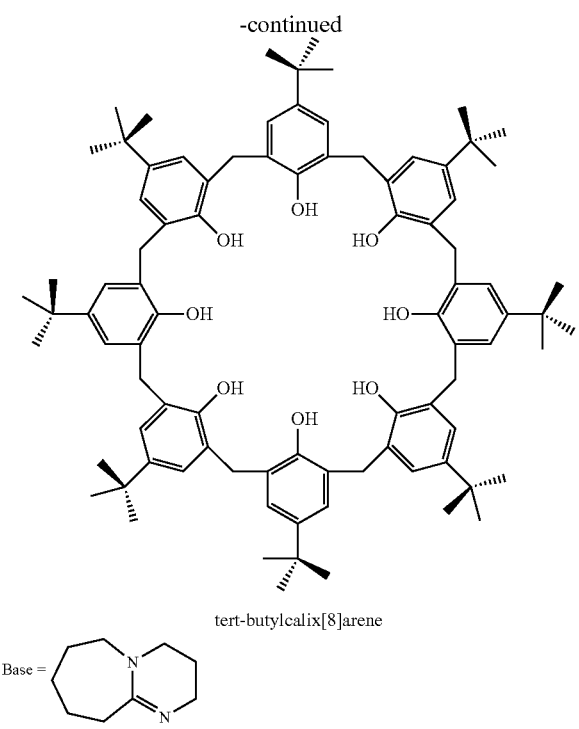

tert-butylcalix[8]arene

Base =

A 2 L round bottom flask, equipped with an overhead stirrer, thermocouple (having a gas inlet, through which nitrogen stream can be applied), and condenser, was loaded with 550.2 g para-tert-butylphenol (PTBP) briquettes (3.66 mol) and 370.0 g A-150 (Solvesso™ 150 Fluid). A gentle nitrogen flow was applied on the surface of the hot reaction mass and the reactor was heated to about 80° C. within 20 minutes. Mixing was set to 112 rpm. Five minutes later, when all the PTBP and A-150 formed a clear solution, 8.8 g DBU (98%, 0.058 mol) was added dropwise at a temperature of 80° C., and a slight exotherm was observed. The reaction mixture was heated to 85° C. and 220 g of 50 wt % formaldehyde solution (3.66 mol) was added within 1 hour and 20 minutes, while the formaldehyde solution was heated periodically with a heat gun to prevent formaldehyde from solidification.

After the formaldehyde addition, the temperature was increased to 90° C., the nitrogen flow was decreased while the circulating cooling water flow was increased to combat extra moisture in the condenser, and the conditions were held for 30 minutes. A formaldehyde trap was placed under the condenser, with the arm to the trap wrapped with aluminum foil. The reaction mixture was heated to reflux for a total of 15 hours. At the end of the reflux, the reaction mass was about 103° C.

The formaldehyde trap was then exchanged against a Dean-Stark trap which was filled with A-150. The condenser was placed on top of the Dean-Stark trap and the heating was resumed to remove the water in the reaction system. About 2.5 hours later, the temperature of the reaction mass reached 111° C., and additional 55.9 g of A-150 was added to the pot. The water removal was facilitated by a slight nitrogen sweep over the surface of the reaction mass. The temperature of the reaction mass reached 145° C. 70 minutes later, and was held at this temperature for additional 5 hours. The reaction mass became progressively thicker. A total of 165.2 g distillate was taken out, and the product weighed 1028.3 g.

Theoretically, the solid content of the crude reaction mass was calculated to be 57.75 wt % (assuming all water from formaldehyde solution and produced from the reaction were removed; and all excess formaldehyde was removed). The final reaction mass contained 2.2 wt % free PTBP (which corresponds to 22.6 g or 4.1 mol % of unreacted PTBP) and less than 15 ppm free formaldehyde.

The yields of the cyclic phenolic resins were determined by further analysis of the $^1$H-NMR results of the crude reaction mass. Although the $^1$H-NMR does not show the unreacted PTBP, the ratio of the integrals of the free phenolic OH signals from the calixarenes (between 8.5 and 11 ppm; see e.g., Stewart et al., *J. Am. Chem. Soc.* 121:4136-46 (1999), which is hereby incorporated by reference in its entirety, to the extent not inconsistent with the subject matter of this disclosure) to the integrals of the proton signals from the methylene bridges for linear and cyclic resins (between 3.4 to 4.5 ppm) provided an estimate for the yields of the respective calixarenes. The signals of methylols and dibenzylethers are low since they are the precursors of the calixarene synthesis—the lower their integral values, the better the conversion.

The analysis results of the $^1$H-NMR results of the final reaction mass are as follows.

| | |
|---|---|
| Integrals for calixarene phenolic OH protons (for all calixarenes) | 0.121 |
| Integrals for two protons of all methylene bridges (cyclic and linear resins) | 0.295 |
| Integrals for one proton of all methylene bridges (cyclic and linear resins) | 0.1475 |
| Ratio of calixarene phenolic OH protons to the protons of all methylene bridges | 0.121/0.1475 = 82.0% |

Taking into account the 4.1 mol % unreacted PTBP in the yield calculation (i.e., 95.9 mol % of the PTBP had reacted) resulted in a crude calixarene yield of 78.7% (i.e., 82.0%× 0.959). That is to say, the theoretical yield of all cyclic components in this crude reaction mass was 78.7%.

Applying the same calculation for the tert-butylcalix[8] arene provided the following results.

| | |
|---|---|
| Integrals for tert-butylcalix[8]arene phenolic OH protons | 0.115 |
| Integrals for one proton of all methylene bridges (cyclic and linear resins) | 0.1475 |
| Ratio of tert-butylcalix[8]arene phenolic OH protons to the protons of all methylene bridges | 0.115/0.1475 = 78.0% |

Taking into account the 4.1 mol % unreacted PTBP in the yield calculation resulted in a crude tert-butylcalix[8]arene yield of 74.8% (i.e., 78.0%×0.959). That is to say, the theoretical yield of tert-butylcalix[8]arene in this crude reaction mass was 74.8%.

Example 2. Synthesis of Tert-Butylcalix[8]Arenes Using Tetraethylammonium Hydroxide (TEAOH) as the Catalyst (in a More Diluted System)

A 500 ml round bottom flask, equipped with an overhead stirrer, thermocouple, overhead addition tank, moisture trap, and condenser was loaded with 112.7 g PTBP briquettes (0.75 mol) and 100.2 g A-150 (Solvesso™ 150 Fluid). A gentle nitrogen flow was applied on the surface of the hot reaction mass and the reactor was heated to about 90° C. When all the PTBP and A-150 formed a clear solution, 5.5 g TEAOH solution (40 wt % in water, 0.015 mol) was added dropwise at a temperature of 87° C., and this temperature was held for 20 minutes. Starting at 87° C., a total of 43.6 g of 51.7 wt % formaldehyde solution (0.75 mol) was added within 12 minutes.

After the formaldehyde addition, the reaction was kept at about 87° C. for one hour. Then, the reaction mixture was heated to reflux for a total of 12 hours. At the end of the reflux, the reaction mass was about 101° C.

The reaction mass was diluted with 100.1 g more A-150 solvent. The reactor was then heated and the temperature target was set to 145° C. to remove the water, and was kept at about 145° C. for about 10 hours until a total of 33.9 g of the lower layer was removed. The crude reaction mass contained 3.8 wt % PTBP.

With a theoretical reaction mass of 324.2 g (assuming all water from formaldehyde solution and produced from the reaction were removed; and all excess formaldehyde was removed), the crude reaction mass contained 3.82 wt % free PTBP (which corresponds to 12.38 g or 11.0 mol % of unreacted PTBP).

The yields of the cyclic phenolic resins were determined by further analysis of the $^1$H-NMR results of the crude reaction mass, using the calculation methodology discussed in Example 1.

The analysis results of the $^1$H-NMR results of the crude reaction mass are as follows.

| | |
|---|---|
| Integrals for calixarene phenolic OH protons (for all calixarenes) | 1.051 |
| Integrals for two protons of all methylene bridges (cyclic and linear resins) | 2.567 |
| Integrals for one proton of all methylene bridges (cyclic and linear resins) | 1.2835 |
| Ratio of calixarene phenolic OH protons to the protons of all methylene bridges | 1.051/1.2835 = 81.9% |

Taking into account the 11.0 mol % unreacted PTBP in the yield calculation (i.e., 89.0 mol % of the PTBP had reacted) resulted in a crude calixarene yield of 72.9% (i.e., 81.9%× 0.89). That is to say, the theoretical yield of all cyclic components in this crude reaction mass was 72.9%.

Applying the same calculation for the tert-butylcalix[8] arene provided the following results.

| | |
|---|---|
| Integrals for tert-butylcalix[8]arene phenolic OH protons | 1.000 |
| Integrals for one proton of all methylene bridges (cyclic and linear resins) | 1.2835 |
| Ratio of tert-butylcalix[8]arene phenolic OH protons to the protons of all methylene bridges | 1.000/1.2835 = 77.9% |

Taking into account the 11.0 mol % unreacted PTBP in the yield calculation resulted in a crude tert-butylcalix[8]arene yield of 69.3% (i.e., 77.9%×0.89). That is to say, the theoretical yield of tert-butylcalix[8]arene in this crude reaction mass was 69.3%.

This crude reaction mass obtained above was then cooled to about 80° C., and was easily filtered through a Büchner funnel. The filter cake was successively washed with portions of A-150 (a total of 102.8 g) to result in a wet filter cake. After drying in vacuum at 130° C., the product tert-butylcalix[8]arene was obtained in an isolated yield of 72.2% (theoretical yield), with an HPLC purity of 98.8% (area % at 281 nm) and less than 0.05 wt % PTBP (GC).

Example 3. Synthesis of Tert-Butylcalix[8]Arenes Using Tetramethylammonium Hydroxide (TMAOH) as the Catalyst and Paraformaldehyde as the Aldehyde Source A 500 ml round bottom flask, equipped with an overhead stirrer, thermocouple, Dean-Stark trap, and condenser was loaded with 112.62 g PTBP briquettes (0.75 mol), 22.68 g paraformaldehyde (0.755 mol), and 204.65 g xylene. The azeo receiver was filled with 27.3 g xylene. A gentle nitrogen flow was applied on the surface of the reaction mass while stirring was switched on at 150 rpm. A 5.51 g TMAOH solution (25 wt % in methanol, 0.015 mol) was added at a low temperature.

The reaction mixture was then heated, and reflux (when xylene formed azeotropes with the formed water) was observed at ~119° C.

About 2.5 hours after heating was started, the temperature of the reaction mass reached about 140° C., and was kept for about 10.5 hours to remove the formed water as completely as possible. Eventually, a total of 17.35 g lower layer (water) was removed from the Dean-Stark trap. The crude reaction mass contained 4.92 wt % free PTBP as well as 58.9 wt % xylene.

This crude reaction mass was then cooled to ~80° C., and was easily filtered through a Büchner funnel. The filter cake was successively washed with five portions of xylene (a total of 533.1 g) to result in a filter cake with 0.12 wt % free PTBP and 8.94 wt % xylene. After drying, the product tert-butylcalix[8]arene was obtained in an isolated yield of 69.3% (of theoretical yield), with an HPLC purity of 95.2% (area % at 281 nm) and possibility of 2.9% tert-butylcalix [9]arene as a side product, and 0.08 wt % PTBP (GC).

Example 4. Synthesis of Tert-Amylcalix[8]Arenes Using Tetramethylammonium Hydroxide (TMAOH) as the Catalyst

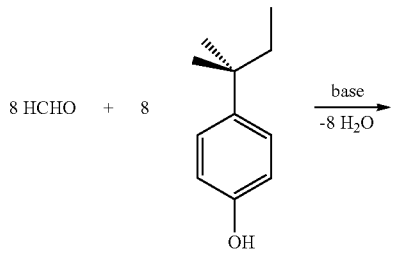

mp.: 88-89° C.
bp.: 255° C.

-continued

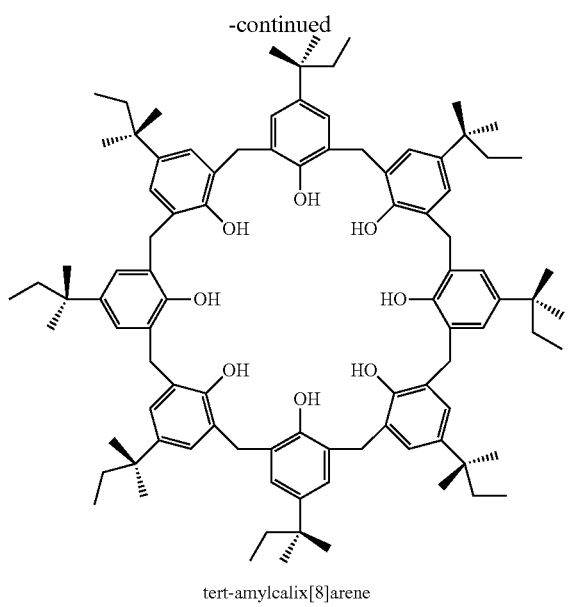

tert-amylcalix[8]arene

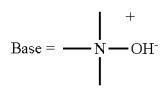

A 500 ml round bottom flask, equipped with an overhead stirrer, thermocouple, overhead addition tank, moisture trap, and condenser was loaded with 123.2 g para-tert-amylphenol (PTAP) briquettes (0.75 mol) and 90.1 g A-150 (Solvesso™ 150 Fluid). A gentle nitrogen flow was applied on the surface of the hot reaction mass and the reactor was heated to about 90° C. When all the PTAP and the A-150 formed a clear solution, 5.5 g of TMAOH solution (25 wt % in methanol, 0.015 mol) was added dropwise at a temperature of 89.3° C. over the course of 3 minutes, and this temperature was held for 60 minutes. At 89.6° C., a total of 51.4 g of 50 wt % formaldehyde solution (0.86 mol) was added within 18 minutes.

After the formaldehyde addition, the reaction was kept at 90° C. for 1.75 hours. The reaction mixture was then heated to reflux at about 99° C. for a total of 12 hours. At the end of the reflux, the reaction mass was at 99.9° C.

The reaction mass was diluted with 70.2 g more A-150 solvent and the empty leg of the azeo trap was filled with 24.5 g A-150. The reactor was then heated and the temperature target was set to 145° C. to remove the water. A lower layer of 13.1 g was removed at 118.2° C. About 62 minutes after the heating was started, the temperature of the reaction mass reached about 145° C., and was kept for about 10 hours until a total of 30.8 g of the lower layer was removed (not all the water/methanol had come out). The crude reaction mass contained 1.3 wt % PTAP as well as 48.5 wt % A-150.

Theoretically, the solid content of the crude reaction mass was calculated to be 45.2 wt % (assuming all water from formaldehyde solution and produced from the reaction were removed; all methanol was removed; and all excess formaldehyde was removed). The crude reaction mass contained 1.3 wt % free PTAP (which corresponds to 3.8 g or 3.1 mol % of unreacted PTAP).

The yields of the cyclic phenolic resins were determined by further analysis of the $^1$H-NMR results of the crude reaction mass, using the calculation methodology discussed in Example 1. It was understood that the $^1$H-NMR does not allow the quantification of the free monomer content; but the GPC results of the final reaction mass display all components in the reaction mass (with their respective resonances at the picked wavelength (here 280 nm)).

The analysis results of the $^1$H-NMR of the crude reaction mass are as follows.

| | |
|---|---|
| Integrals for calixarene phenolic OH protons (for all calixarenes) | 0.075 |
| Integrals for two protons of all methylene bridges (cyclic and linear resins) | 0.181 |
| Integrals for one proton of all methylene bridges (cyclic and linear resins) | 0.0905 |
| Ratio of calixarene phenolic OH protons to the protons of all methylene bridges | 0.075/0.0905 = 82.9% |

Taking into account the 3.1 mol % unreacted PTAP in the yield calculation (i.e., 96.9 mol % of the PTAP had reacted) resulted in a crude calixarene yield of 80.3% (i.e., 82.9%× 0.969). That is to say, the theoretical yield of all cyclic components in this crude reaction mass was 80.3%.

Applying the same calculation for the tert-amylcalix[8] arene provided the following results.

| | |
|---|---|
| Integrals for tert-amylcalix[8]arene phenolic OH protons | 0.073 |
| Integrals for two protons of all methylene bridges (cyclic and linear resins) | 0.181 |
| Integrals for one proton of all methylene bridges (cyclic and linear resins) | 0.0905 |
| Ratio of tert-amylcalix[8]arene phenolic OH protons to the protons of all methylene bridges | 0.073/0.0905 = 80.7% |

Taking into account the 3.1 mol % unreacted PTAP in the yield calculation resulted in a crude tert-amylcalix[8]arene yield of 78.2% (i.e., 80.7%×0.969). That is to say, the theoretical yield of tert-amylcalix[8]arene in this crude reaction mass was 78.2%. This is close to the observed isolated yield.

This crude reaction mass obtained above was then cooled to about 80° C., and was easily filtered through a Büchner funnel. The filter cake was successively washed with three portions of A-150 (a total of 454.3 g) to result in a wet filter cake with 0.3 wt % free PTAP and 6.9 wt % A-150. After drying, the product tert-amylcalix[8]arene was obtained in an isolated yield of 76.6% (theoretical yield), with an HPLC purity of 99.3% (area % at 281 nm).

Example 5. Synthesis of Tert-Octylcalix[8]Arenes Using Tetraethylammonium Hydroxide (TEAOH) as the Catalyst

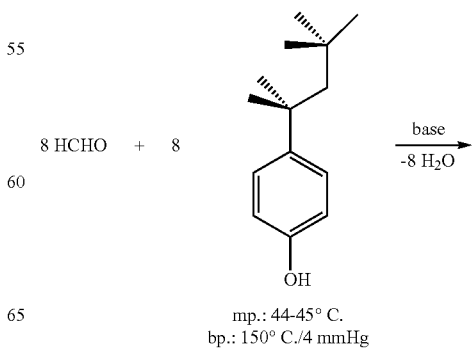

mp.: 44-45° C.
bp.: 150° C./4 mmHg

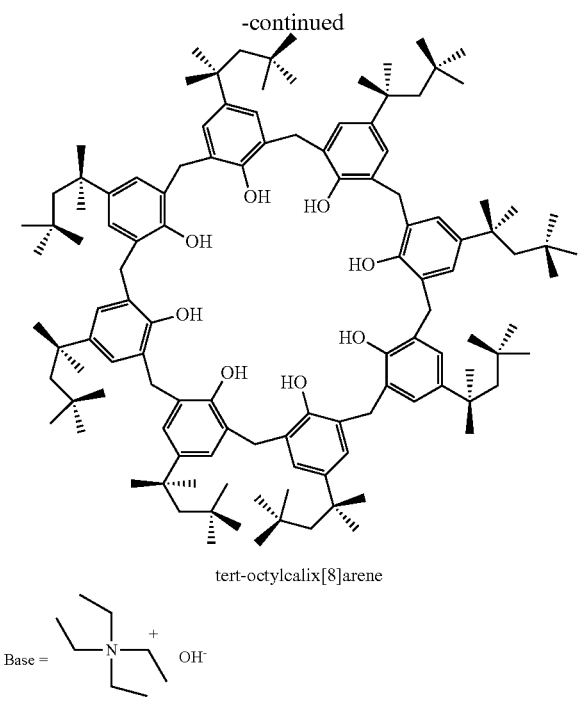

tert-octylcalix[8]arene

Base = [triethylammonium hydroxide structure] OH⁻

A 500 ml round bottom flask, equipped with an overhead stirrer, thermocouple, overhead addition tank, moisture trap, and condenser was loaded with 154.7 g para-tert-octylphenol (PTOP) briquettes (0.75 mol) and 89.6 g A-150 (Solvesso™ 150 Fluid). A gentle nitrogen was applied on the surface of the hot reaction mass and the reactor was heated to about 90° C. When all the PTOP and the A-150 formed a clear solution, 5.5 g of a 40% solution of TEAOH (40 wt % in water, 0.015 mol) was added dropwise at a temperature of 92.1° C. over the course of 5 minutes, and this temperature was hold for 100 minutes. At 90.1° C., a total of 50.5 g of 50 wt % formaldehyde solution (0.84 mol) was added within 23 minutes.

After the formaldehyde addition, the reaction was kept at 90° C. for 1 hour. The reaction mixture was then heated to reflux at about 100° C. for a total of 12 hours. At the end of the reaction, the reaction mass was about 100° C.

The reaction mass was diluted with 13.5 g more A-150 solvent and the empty leg of the azeo trap was filled with 24.4 g A-150. The reactor was then heated and the temperature target was set to 145° C. to remove the water. A lower layer of 16.9 g was removed at 120.5° C. About 1.75 hours after the heating was started, the temperature of the reaction mass reached about 145° C., and was kept for about 10 hours until a total of 36.3 g of the lower layer was removed (not all the water/methanol had come out). The crude reaction mass contained 1.4 wt % PTOP as well as 37.9 wt % A-150.

Theoretically, the solid content of the crude reaction mass was calculated to be 60.85 wt % (assuming all water from formaldehyde solution and produced from the reaction were removed; and all excess formaldehyde was removed). The crude reaction mass contained 1.4 wt % free PTOP (which corresponds to 3.8 g or 2.4 mol % of unreacted PTOP).

The yields of the cyclic phenolic resins were determined by further analysis of the $^1$H-NMR results of the crude reaction mass, using the calculation methodology discussed in Example 1. It was understood that the $^1$H-NMR does not allow the quantification of the free monomer content; but the GPC results of the final reaction mass display all components in the reaction mass (with their respective resonances at the picked wavelength (here 280 nm)).

The analysis results of the $^1$H-NMR results of the crude reaction mass are as follows.

| | |
|---|---|
| Integrals for calixarene phenolic OH protons (for all calixarenes) | 0.084 |
| Integrals for two protons of all methylene bridges (cyclic and linear resins) | 0.210 |
| Integrals for one proton of all methylene bridges (cyclic and linear resins) | 0.105 |
| Ratio of calixarene phenolic OH protons to the protons of all methylene bridges | 0.084/0.105 = 80.0% |

Taking into account the 2.4 mol % unreacted PTOP in the yield calculation (i.e., 97.6 mol % of the PTOP had reacted) resulted in a crude calixarene yield of 78.1% (i.e., 80.0%× 0.976). That is to say, the theoretical yield of all cyclic components in this crude reaction mass was 78.1%.

Applying the same calculation for the tert-octylcalix[8]arene provided the following results.

| | |
|---|---|
| Integrals for tert-octylcalix[8]arene phenolic OH protons | 0.078 |
| Integrals for two protons of all methylene bridges (cyclic and linear resins) | 0.210 |
| Integrals for one proton of all methylene bridges (cyclic and linear resins) | 0.105 |
| Ratio of tert-octylcalix[8]arene phenolic OH protons to the protons of all methylene bridges | 0.078/0.105 = 74.3% |

Taking into account the 2.4 mol % unreacted PTOP in the yield calculation resulted in a crude tert-octylcalix[8]arene yield of 72.5% (i.e., 74.3%×0.976). That is to say, the theoretical yield of tert-octylcalix[8]arene in this crude reaction mass was 72.5%.

This crude reaction mass obtained above was then cooled to about 80° C., and was easily filtered through a Büchner funnel. The filter cake was successively washed with three portions of A-150 (a total of 452.3 g), and dried in the vacuum oven to result in a product tert-octylcalix[8]arene in an isolated yield of 64.6% (theoretical yield), with an HPLC purity of 98.9% (area % at 281 nm), and less than 0.05 wt % free PTOP and 0.13 wt % A-150.

Example 6. Synthesis of Tert-Butylcalix[8]Arene Using Tetramethylammonium Hydroxide (TMAOH) as the Catalyst in Diphenyl Ether

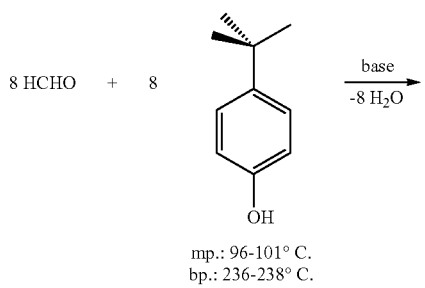

mp.: 96-101° C.
bp.: 236-238° C.

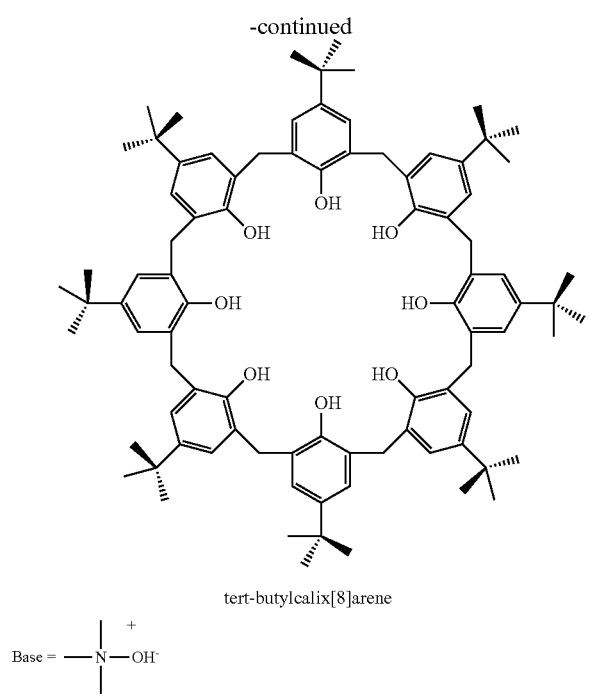

tert-butylcalix[8]arene

Base = —N⁺—OH⁻

A 500 ml round bottom flask, equipped with an overhead stirrer, thermocouple (having a gas inlet, through which nitrogen stream can be applied), and condenser was loaded with 112.34 g PTBP briquettes (0.75 mol) and 108.25 g diphenyl ether. A gentle nitrogen flow was on the surface of the hot reaction mass and the reactor was heated to about 80° C. within 20 minutes. Mixing was set to 200 rpm. Five minutes later, when all the PTBP and diphenyl ether formed a clear solution, 5.5 g TMAOH solution (25% in methanol, 0.015 mol) was added dropwise through addition funnel at a temperature of 89° C. The reaction mixture was heated to 90° C. and 49.7 g of 50 wt % formaldehyde solution (0.83 mol) was added through the addition funnel within 30 minutes, while the formaldehyde solution was heated periodically with a heat gun to prevent formaldehyde from solidification.

Fifteen minutes after the end of the formaldehyde addition, the temperature was increased to 100° C., the nitrogen flow was decreased while the circulating cooling water flow was increased to combat extra moisture in the condenser, and the conditions were held for 12 hours. At the end of the reflux, the reaction mass was about 100° C.

The condenser was then exchanged against a Dean-Stark trap which was left empty. The condenser was placed on top of the Dean-Stark trap, the temperature target was set to 110° C., and the stirring speed was set to 200 rpm. The heating was then started to remove the water. The reactor temperature reached 111° C. after 72 minutes, and 140.6 g more diphenyl ether was added to the reactor. A 21.2 g water layer was removed from the side arm of the Dean-Stark trap seven minutes later. The reaction mass was then heated to 120° C. and, after an additional forty minutes, to 130° C. The reaction mass became foamy and the heating blanket, which was covering the upper parts of the flask, was loosened. This foam was likely from the dissolved water in diphenyl ether, which evaporated 25 minutes later, and the heating was increased to 135° C. The nitrogen stream over the surface of the reaction mass was slightly enhanced to facilitate further water removal. Two hours later, the temperature was increased to 140° C. and continued for 1.5 more hours, until a total of 35.06 g of the lower layer was removed (theoretically, the lower layer should be 43.3 g). The distillation was resumed at 140° C. and subsequently increased to 160° C. over the course of 7 hours. Only 0.97 g more distillate was obtained (a total of 36.03 g). The crude reaction mass contained 1.13 wt % free PTBP.

Theoretically, the solid content of the crude reaction mass was calculated to be 32.65 wt % (assuming all water from formaldehyde solution and produced from the reaction were removed; and all excess formaldehyde was removed). The crude reaction mass contained 1.13 wt % free PTBP (which corresponds to 4.15 g or 3.7 mol % of unreacted PTBP.

The yields of the cyclic phenolic resins were determined by further analysis of the $^1$H-NMR results of the crude reaction mass, using the calculation methodology discussed in Example 1. It was understood that the $^1$H-NMR does not allow the quantification of the free monomer content; but the GPC results of the final reaction mass display all components in the reaction mass (with their respective resonances at the picked wavelength (here 280 nm)).

The analysis results of the $^1$H-NMR results of the crude reaction mass are as follows.

| | |
|---|---|
| Integrals for calixarene phenolic OH protons (for all calixarenes) | 1.077 |
| Integrals for two protons of all methylene bridges (cyclic and linear resins) | 2.423 |
| Integrals for one proton of all methylene bridges (cyclic and linear resins) | 1.2115 |
| Ratio of calixarene phenolic OH protons to the protons of all methylene bridges | 1.077/1.2115 = 88.9% |

Taking into account the 3.7 mol % unreacted PTBP in the yield calculation (i.e., 96.3 mol % of the PTBP had reacted) resulted in a crude calixarene yield of 85.6% (i.e., 88.9%× 0.963). That is to say, the theoretical yield of all cyclic components in this crude reaction mass was 85.6%.

Applying the same calculation for the tert-butylcalix[8]arene provided the following results.

| | |
|---|---|
| Integrals for tert-butylcalix[8]arene* phenolic OH protons | 1.054 |
| Integrals for two protons of all methylene bridges (cyclic and linear resins) | 2.423 |
| Integrals for one proton of all methylene bridges (cyclic and linear resins) | 1.2115 |
| Ratio of tert-butylcalix[8]arene phenolic OH protons to the protons of all methylene bridges | 1.054/1.2115 = 87.0% |

*As shown in the HPLC analysis below, a small amount of tert-butylcalix[9]arene side product presented in this sample. Thus, the $^1$H-NMR peaks for tert-butylcalix[8]arene presumably also included tert-butylcalix[9]arene.

Taking into account the 3.7 mol % unreacted PTBP in the yield calculation resulted in a crude tert-butylcalix[8]arene yield of 83.8% (i.e., 87.0%×0. 963). That is to say, the theoretical yield of tert-butylcalix[8]arene in this crude reaction mass was 83.8%. This is close to the actual isolated yield of 84.2%.

This crude reaction mass obtained above was then cooled down and was easily filtered through a Büchner funnel. The filter cake was successively washed with three portions of ethyl acetate (100 g each portion). After drying, a white filter cake was obtained, showing the following compositions: 0.12 wt % PTBP, 4.81 wt % diphenyl ether and 0.18 wt % ethyl acetate. The HPLC analysis (which did not account for solvents and unreacted alkylphenols) showed a purity of 92.3% (area % at 281 nm) of tert-butylcalix[8]arene and 5.14% (area % at 281 nm) of a side product believed to be tert-butylcalix[9]arene. The isolated yield was 84.2%.

Example 7. Synthesis of Sec-Butylcalix[8]Arenes Using Tetramethylammonium Hydroxide (TMAOH) as the Catalyst

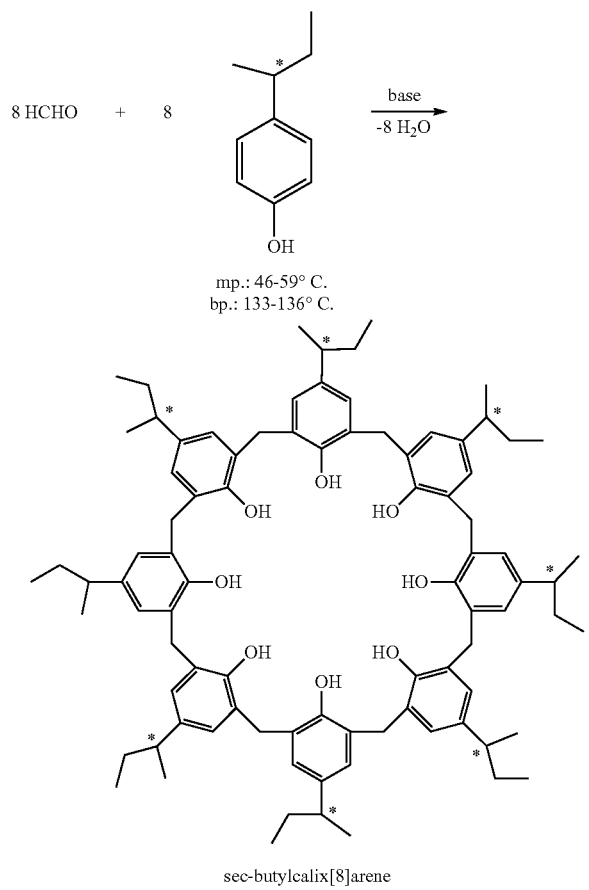

sec-butylcalix[8]arene

A 500 ml round bottom flask, equipped with an overhead stirrer, thermocouple, overhead addition tank, moisture trap, and condenser was loaded with 112.7 g para-sec-butylphenol (PSBP) powder (>98%, 0.75 mol) and 100.2 g A-150 (Solvesso™ 150 Fluid). A gentle nitrogen flow was applied on the surface of the hot reaction mass and the reactor was heated to about 90° C. When all the PSBP and the A-150 formed a clear solution, 5.5 g of TMAOH solution (25 wt % in methanol, 0.015 mol) was added dropwise at a temperature of 85-90° C., and this temperature was hold for 30 minutes. At 90° C., a total of 46.0 g of 48.9 wt % formaldehyde solution (0.749 mol) was added within 16 minutes.

After the formaldehyde addition, the reaction was kept at 90° C. for 1 hour. The reaction mixture was then heated to reflux for a total of 12 hours. At the end of the reflux, the reaction mass was at about 99° C.

The reaction mass was diluted with 99.7 g more A-150 solvent. The reactor was then heated and the temperature target was set to 145° C. to remove the water. About 2 hours after the heating was started, the temperature of the reaction mass reached about 142° C., and was kept at 142-145° C. for about 10 hours until a total of 26.8 g of the lower layer was removed. The crude reaction mass contained 3.43 wt % PSBP.

Theoretically, the solid content of the crude reaction mass was calculated to be 37.7 wt % (assuming all water from formaldehyde solution and produced from the reaction were removed; and all excess formaldehyde was removed). The crude reaction mass contained 3.43 wt % free PSBP (which corresponds to 11.08 g or 9.8 mol % of unreacted PSBP).

The yields of the cyclic phenolic resins were determined by further analysis of the $^1$H-NMR results of the crude reaction mass, using the calculation methodology discussed in Example 1. It was understood that the $^1$H-NMR does not allow the quantification of the free monomer content; but the GPC results of the final reaction mass display all components in the reaction mass (with their respective resonances at the picked wavelength (here 280 nm)).

The analysis results of the $^1$H-NMR results of the crude reaction mass are as follows.

| | |
|---|---|
| Integrals for calixarene phenolic OH protons (for all calixarenes) | 0.055 |
| Integrals for two protons of all methylene bridges (cyclic and linear resins) | 0.130 |
| Integrals for one proton of all methylene bridges (cyclic and linear resins) | 0.065 |
| Ratio of calixarene phenolic OH protons to the protons of all methylene bridges | 0.055/0.065 = 84.6% |

Taking into account the 9.8 mol % unreacted PSBP in the yield calculation (i.e., 90.2 mol % of the PSBP had reacted) resulted in a crude calixarene yield of 76.3% (i.e., 84.6%× 0.902). That is to say, the theoretical yield of all cyclic components in this crude reaction mass was 76.3%.

Applying the same calculation for the sec-butylcalix[8] arene provided the following results.

| | |
|---|---|
| Integrals for sec-butylcalix[8]arene phenolic OH protons | 0.051 |
| Integrals for two protons of all methylene bridges (cyclic and linear resins) | 0.130 |
| Integrals for one proton of all methylene bridges (cyclic and linear resins) | 0.065 |
| Ratio of sec-butylcalix[8]arene phenolic OH protons to the protons of all methylene bridges | 0.051/0.065 = 78.5% |

Taking into account the 9.8 mol % unreacted PSBP in the yield calculation resulted in a crude sec-butylcalix[8]arene yield of 70.8% (i.e., 78.5%×0.902). That is to say, the theoretical yield of sec-butylcalix[8]arene in this crude reaction mass was 70.8%. This is close to the observed isolated yield.

This crude reaction mass obtained above was then cooled to about 80° C., and was easily filtered through a Büchner funnel. The filter cake was successively washed with a total of 105.4 g of A-150. After drying, the product sec-butylcalix [8]arene was obtained in an isolated yield of 66.3% (theoretical yield), with an HPLC purity of 99.2% (area % at 281 nm), and less than 0.05 wt % free PSBP and less than 0.05 wt % A-150.

As noted above and demonstrated through these examples, it has been discovered that calix[8]arenes are obtained in a higher yield and higher solid content, and with a significantly improved purity and selectivity. The use of a nitrogen-containing base as a catalyst assists this process. The purity of calix[8]arenes can be further improved by a simple filtration, without the need for recrystallization.

As a comparison, the conventional process using an alkaline base (such as sodium hydroxide) as the catalyst in a highly diluted reaction system (e.g., 100 g PTBP reacting with 35 g paraformaldehyde in 600 ml xylene solvent; see Munch et al., Organic Syntheses 68: 243-46 (1990)) produced with about 20% solid content, and needed a recrystallization step to remove at least 13% of other calixarene oligomers (e.g., calix[4]arene and calix[6]arene) produced in the crude cyclic reaction product. The process disclosed in this application was able to produce about 33% or more solid content, with a purity of calix[8]arene of 98% or more (characterized by HPLC analysis; not accounting for the attached solvent and the unreacted free phenolic monomers), after a filtration and drying step. See Examples 1 and 5. No recrystallization was needed.

Example 8. Synthesis of Tert-Amylcalix[8]Arenes Using Tetramethylammonium Hydroxide (TMAOH) as the Catalyst in Diphenylether/Xylene A 500 ml round bottom flask, equipped with an overhead stirrer, thermocouple, overhead addition tank, moisture trap, and condenser was loaded with 123.2 g para-tert-amylphenol (PTAP) briquettes (0.75 mol), 90.2 g diphenylether (DPE), and 10.2 g xylene. A gentle nitrogen flow was applied on the surface of the reaction mass and the reactor was heated to about 90° C. When all the PTAP and the DPE/xylene formed a clear solution, 5.5 g of TMAOH solution (25 wt % in methanol, 0.015 mol) was added dropwise at a temperature of 89° C. over the course of 3 minutes, and this temperature was held for 75 minutes. At 89° C., a total of 52.2 g of 49.2 wt % formaldehyde solution (0.86 mol) was added within 25 minutes.

After the formaldehyde addition, the reaction was kept at 90° C. for 1 hour. The reaction mixture was then heated to reflux at about 96° C. for a total of 12 hours. At the end of the reflux, the reaction mass was at about 100° C.

The reaction mass was diluted with 60.1 g DPE and 20.1 g xylene solvent mixture. Xylene was added to) remove the formed water from the reaction mass to avoid boilovers (due to the high boiling point of diphenyl ether as it cannot form effective azeotropes with water by itself).

The reactor was then heated and the temperature target was set to 145° C. to remove the water. The temperature of the reaction mass was kept at 145° C. for a total of 10 hours until a total of 34.5 g of lower layer was removed. This water layer contained 6.4 wt % formaldehyde, which correlates to 8.6% of the total formaldehyde load. The crude reaction mass contained 1.02 wt % PTAP (which corresponds to 2.6% of the starting load of PTAP).

This crude reaction mass obtained above was then cooled to about 50° C., and was filtered through a Buechner funnel. The filter cake was successively washed with xylene (a total of 106.2 g), and dried in a vacuum oven at 130° C. The final product tert-amylcalix[8]arene was obtained in an isolated yield of 81.2% (theoretical yield) with an HPLC purity of 98.8% (area % at 281 nm) and less than 0.05 wt % free PTAP and 2.78% DPE.

Example 9. Synthesis of Tert-Octylcalix[8]Arenes Using Tetraethylammonium Hydroxide (TEAOH) as the Catalyst in Hexadecane A 500 ml round bottom flask, equipped with an overhead stirrer, thermocouple, overhead addition tank, moisture trap, and condenser was loaded with 154.7 g para-tert-octylphenol (PTOP) briquettes (0.75 mol) and 100.0 g hexadecane. A gentle nitrogen was applied on the surface of the reaction mass and the reactor was heated to about 90° C. When all the PTOP and the A-150 formed a clear solution, 5.5 g of a 40% solution of TEAOH (40 wt % in water, 0.015 mol) was added dropwise over the course of 9 minutes. At 90° C., a total of 55.3 g of 46.8 wt % formaldehyde solution (0.86 mol) was added within 25 minutes.

After the formaldehyde addition, the reaction was kept at 90° C. for 1 hour. The reaction mixture was then heated to reflux at about 100° C. for a total of 12 hours. At the end of the reaction, the reaction mass was about 100° C.

The reaction mass was diluted with 70.1 g more hexadecane solvent. The reactor was then heated and the temperature target was set to 145° C. to remove the water. About 2 hours after the heating was started, the temperature of the reaction mass reached about 145° C., and was kept for about 10 hours. The crude reaction mass contained 0.68 wt % PTOP.

This crude reaction mass obtained above was then cooled to about 70-80° C., and was filtered through a Buechner funnel. The filter cake was successively washed with portions of isopropanol (a total of 100.6 g), and dried in the vacuum oven at about 130° C. to result in a product tert-octylcalix[8]arene in an isolated yield of 79.4% (theoretical yield), with an HPLC purity of 97.0% (area % at 281 nm), and 0.13 wt % free PTOP and 0.13 wt % hexadecane (both determined by GC).

Example 10. Synthesis of Para-Cumylcalix[8]Arenes Using Tetramethylammonium Hydroxide (TMAOH) as the Catalyst A 500 ml round bottom flask, equipped with an overhead stirrer, thermocouple, overhead addition tank, moisture trap, and condenser was loaded with 160.1 g para-cumylphenol (PCP) (0.75 mol) and 100.5 g A-150 (Solvesso™ 150 Fluid). A gentle nitrogen flow was applied on the surface of the hot reaction mass and the reactor was heated to about 90° C. When all the PCP and the A-150 formed a clear solution, 5.6 g of TMAOH solution (25 wt % in methanol, 0.015 mol) was added. At about 90° C., a total of 70.7 g of 37 wt % formaldehyde solution (0.87 mol, stabilized with 10-15% methanol) was added within 17 minutes.

After the formaldehyde addition, the reaction was kept at 90° C. for 1 hour. The reaction mixture was then heated to reflux at about 100° C. for a total of 12 hours. At the end of the reflux, the reaction mass was at about 100° C.

The reaction mass was diluted with 78.9 g more A-150 solvent. The reactor was then heated and the temperature target was set to 145° C. to remove the water (excess formaldehyde and potentially remaining methanol). About 94 minutes after the heating was started, the temperature of the reaction mass reached about 144° C. and was kept for about 10 hours. The crude reaction mass contained 3.25 wt % unreacted para-cumylphenol.

This crude reaction mass obtained above was then cooled to about 70-80° C., and the obtained slurry was filtered through a Buechner funnel. The filtered material was successively washed with a first portion of 105.2 g A-150 solvent and a second portion of 78.0 g A-150 solvent, and dried in a vacuum oven at 130° C. The final product para-cumylphenol (113.9 g) was obtained in an isolated yield of 60.6% (theoretical yield) with an HPLC purity of 91.0% (area % at 281 nm) and 0.99 wt % free PCP and less than 0.05 wt % A-150 (both determined by GC). The impurities in the final product may contain some linear resins as well as calix[6]arene and calix[7]arene.

Example 11. Synthesis of Tert-Amylcalix[8]Arenes Using Tetramethylammonium Hydroxide (TMAOH) as the Catalyst A 500 ml round bottom flask, equipped with an overhead stirrer, thermocouple, overhead addition tank, moisture trap, and condenser was loaded with 123.2 g para-tert-amylphenol (PTAP) briquettes (0.75 mol) and 88.6 g A-150 (Solvesso™ 150 Fluid). A gentle nitrogen flow was applied on the surface of the reaction mass and the reactor was heated to about 75° C. Over the course of 3 minutes, 5.5 g of TMAOH solution (25 wt % in methanol, 0.015 mol) was added dropwise. At 90° C., a total of 51.0 g of 50.4 wt % formaldehyde solution (0.86 mol) was added within 7 minutes.

After the formaldehyde addition, the reaction was kept at 90° C. for 1 hour. The reaction mixture was set to reflux conditions and was forcefully heated (e.g., it took about 15 minutes to heat the reaction mixture from room temperature to reach about 100° C. and within 60-120 minutes the pot temperature can reach about 111° C.), while allowing the distillate to return back into the reaction flask. The pot temperature reached to about 115° C. within 4.5 hours of heating and was held at 115° C. for additional 1.5 hours. The crude reaction product contained 0.52 wt % free formaldehyde and 8.93 wt % unreacted para-tert-amylphenol.

The reactor was then heated and the temperature target was set to 145° C. to remove the water. The temperature of the reaction mass was kept at 145° C. for a total of 10 hours until the water and excess formaldehyde were distilled out. The 38.5 g of aqueous distillate removed contained 2.5 g formaldehyde (which corresponds to 9.74% of the starting formaldehyde).

The crude product tert-amylcalix[8]arene was obtained with an HPLC purity of 86.0% (area % at 281 nm) and 1.98 wt % PTAP (which corresponds to 3.6% of the starting PTAP). The solid content of the final calixarene reaction mass was determined to be about 60%.

This crude reaction mass obtained above was then cooled to about 60-70° C., and was filtered through a Buechner funnel. The filter cake was successively washed with 101.7 g A-150 and dried in vacuum oven at 130° C. to result in a tert-amylcalix[8]arene product in an isolated yield of 81.3% (theoretical yield), with an HPLC purity of 99.0% (area % at 281 nm), 0.44 wt % free PTAP and 1.17 wt % A-150.

Example 12. Synthesis of Tert-Amylcalix[8]Arenes Using Tetramethylammonium Hydroxide (TMAOH) as the Catalyst and Paraformaldehyde as the Aldehyde Source in Diphenylether A 500 ml round bottom flask, equipped with an overhead stirrer, thermocouple, overhead addition tank, moisture trap, and condenser was loaded with 123.2 g para-tert-amylphenol (PTAP) briquettes (0.75 mol), 27.0 g paraformaldehyde (95%, 0.85 mol), and 88.5 g diphenylether. A gentle nitrogen flow was applied on the surface of the reaction mass and the reactor was heated to about 68° C. To the reaction suspension, at a temperature of 68-80° C., 5.5 g of TMAOH solution (25 wt % in methanol, 0.015 mol) was added dropwise over the course of 3 minutes.

The reaction mixture was then further heated with the temperature target set to 145° C. to remove the water through the moisture trap, with the gentle nitrogen flow assisting in transporting the water to the trap. The temperature of the reaction mass reached about 143° C. within 41 minutes, and was kept for about 5 hours between 143-155° C. The 16.0 g aqueous distillate removed contained 2.4 g formaldehyde (which corresponds to 9.4% of the starting formaldehyde).

The crude product tert-amylcalix[8]arene was obtained with an HPLC purity of 85.1% (area % at 281 nm) and 1.27 wt % PTAP (which corresponds to 2.3% of the starting PTAP). The solid content of the final calixarene reaction mass was determined to be about 60%.

This crude reaction mass obtained above was then cooled to about 75° C., and was filtered through a Buechner funnel. The filter cake was successively washed with portions of 108.1 g xylene and dried in vacuum oven at 130° C. to result in a tert-amylcalix[8]arene product in an isolated yield of 82.6% (theoretical yield), with an HPLC purity of 96.5% (area % at 281 nm), 0.09 wt % free PTAP and 3.91% diphenylether.

Example 13. Synthesis of Tert-Amylcalix[8]Arenes Using 4-(Dimethylamino)Pyridine (DMAP) as the Catalyst

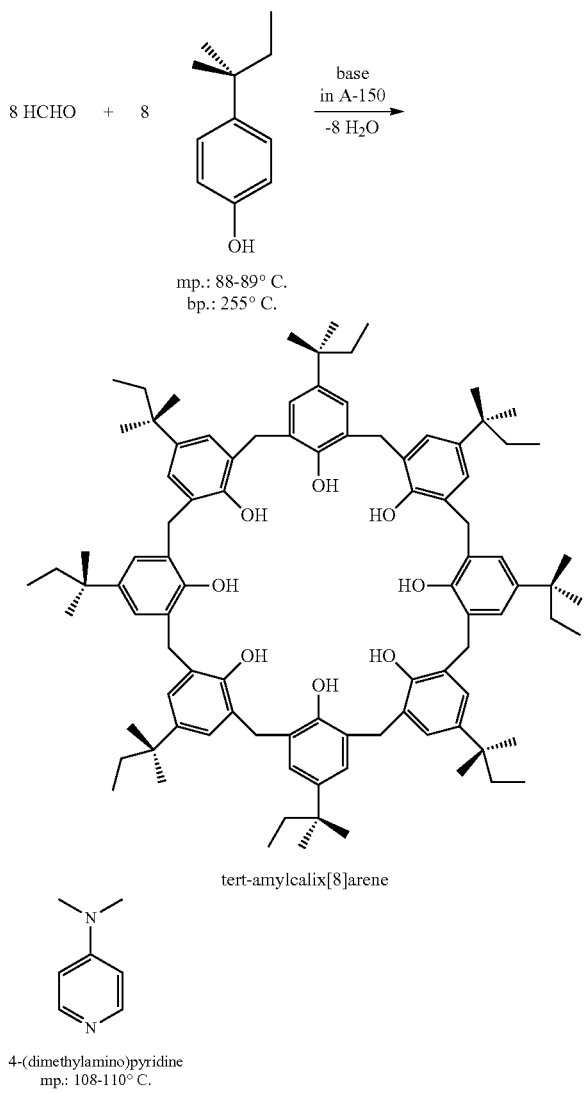

A 500 ml round bottom flask, equipped with an overhead stirrer, thermocouple, overhead addition tank, moisture trap, and condenser was loaded with 123.2 g para-tert-amylphenol (PTAP) briquettes (0.75 mol) and 100.8 g A-150 (Solvesso™ 150 Fluid). A gentle nitrogen flow was applied on the surface of the reaction mass and the reactor was heated to about 90° C. When all the PTAP and the A-150 formed a clear solution, 1.8 g 4-(dimethylamino)pyridine (0.015 mol) was added at about 93° C., and the temperature was held for 46 minutes. At about 73° C., a total of 55.9 g of 45.9 wt % formaldehyde solution (0.85 mol) was added within 17 minutes.

After the formaldehyde addition, the reaction was kept at 90° C. for 1 hour. The reaction mixture was then heated to reflux at about 99° C. for a total of 12 hours. At the end of the reaction, the reaction mass was at about 99° C.

The reaction mass was diluted with 50.1 g more A-150 solvent. The reactor was then heated to distillation conditions with the temperature target set to 145° C. to remove the water. The temperature of the reaction mass was kept at 145° C. for about 10 hours until a lower layer of 35.4 g was removed, which contained 11.6 wt % formaldehyde (which corresponds to 16.0% of the starting formaldehyde). The crude reaction mass contained 0.85 wt % PTAP (which corresponds to 1.9% of the starting PTAP).

This crude reaction mass obtained above was then cooled to about 74° C., and was easily filtered through a Buechner funnel. The filter cake was successively washed with 105.0 g A-150 and dried in vacuum oven at 130° C. to result in a tert-amylcalix[8]arene product in an isolated yield of 79.9% (theoretical yield), with an HPLC purity of 99.0% (area % at 281 nm), 0.18 wt % free PTAP and 0.32 wt % A-150.

Example 14. One-Pot Synthesis of Tert-Amylcalix[4]Arenes from In-Situ Conversion of Tert-Amylcalix[8]Arenes (Using TMAOH Catalyst) Using Sodium Hydroxide as the Catalyst, with an Antisolvent

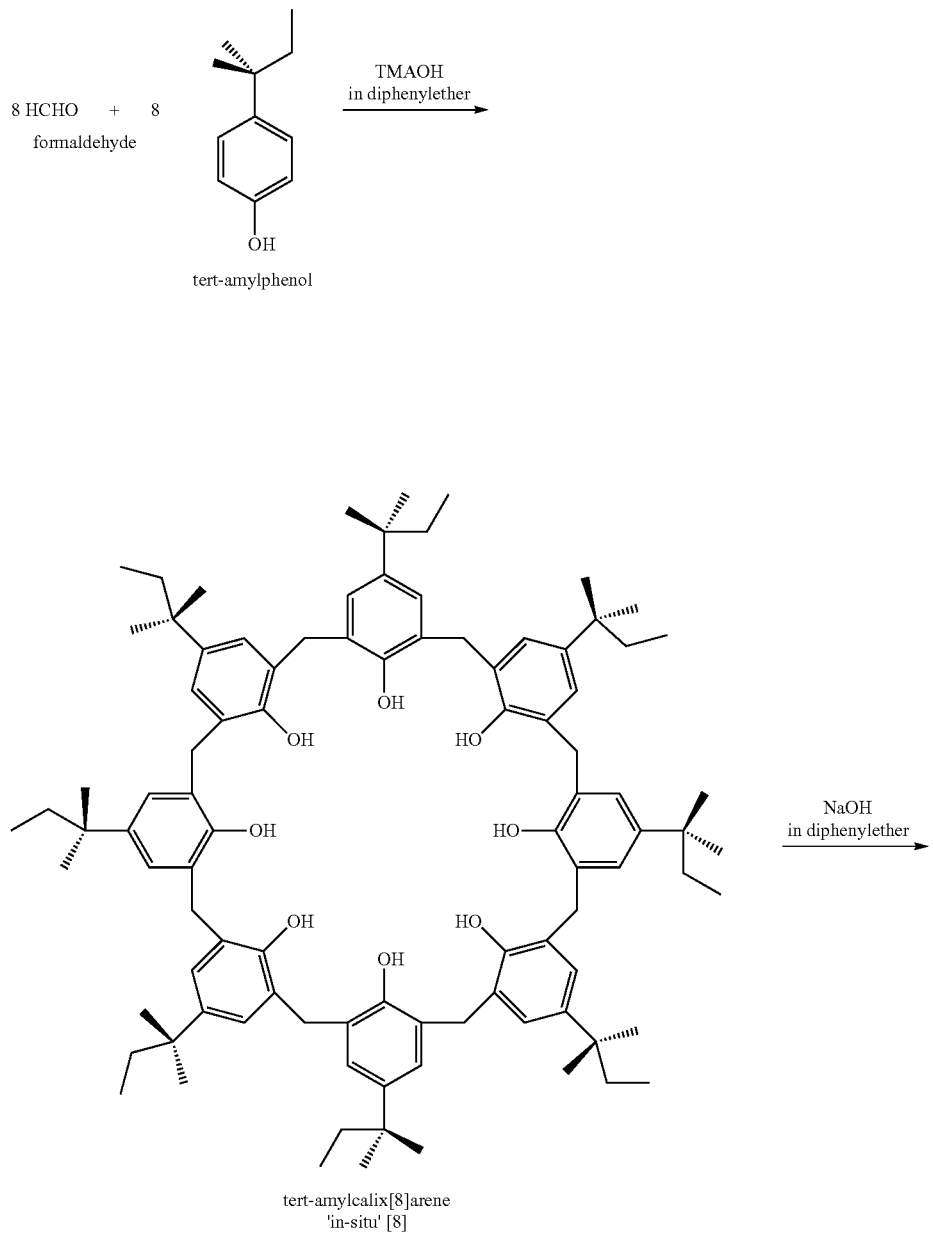

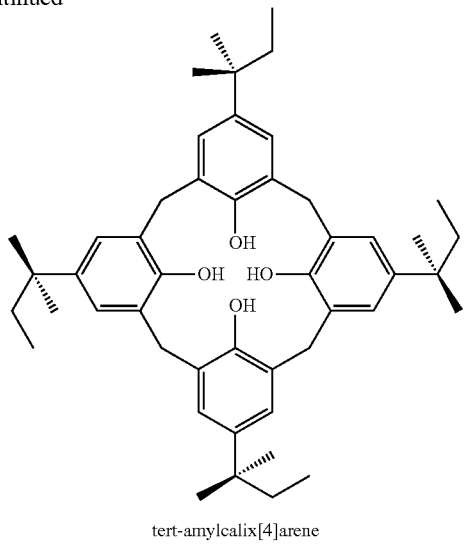

tert-amylcalix[4]arene

Preparation of Tert-Amylcalix[8]Arene

A 500 ml round bottom flask, equipped with an overhead stirrer, thermocouple, overhead addition tank, moisture trap, and condenser, was loaded with 122.85 g para-tert-amylphenol (PTAP) briquettes (0.75 mol) and 115.1 g diphenyl ether. A gentle nitrogen flow was applied on the surface of the hot reaction mass and the reactor was heated to about 85° C. When all the PTAP and the diphenyl ether formed a clear solution, 5.5 g of TMAOH solution (25 wt % in methanol, 0.015 mol) was added dropwise at a temperature of 87.5° C. over the course of about 5 minutes. At about 86° C., a total of 50.8 g of 50.7 wt % aqueous formaldehyde solution (0.86 mol) was added within 55 minutes.

After the formaldehyde addition, the reaction was kept at 90° C. for about 1 hour. The reaction mixture was then heated to reflux at about 100° C. for a total of about 12 hours. At the end of the reflux, the reaction mass was at about 100° C.

Figure 1B:
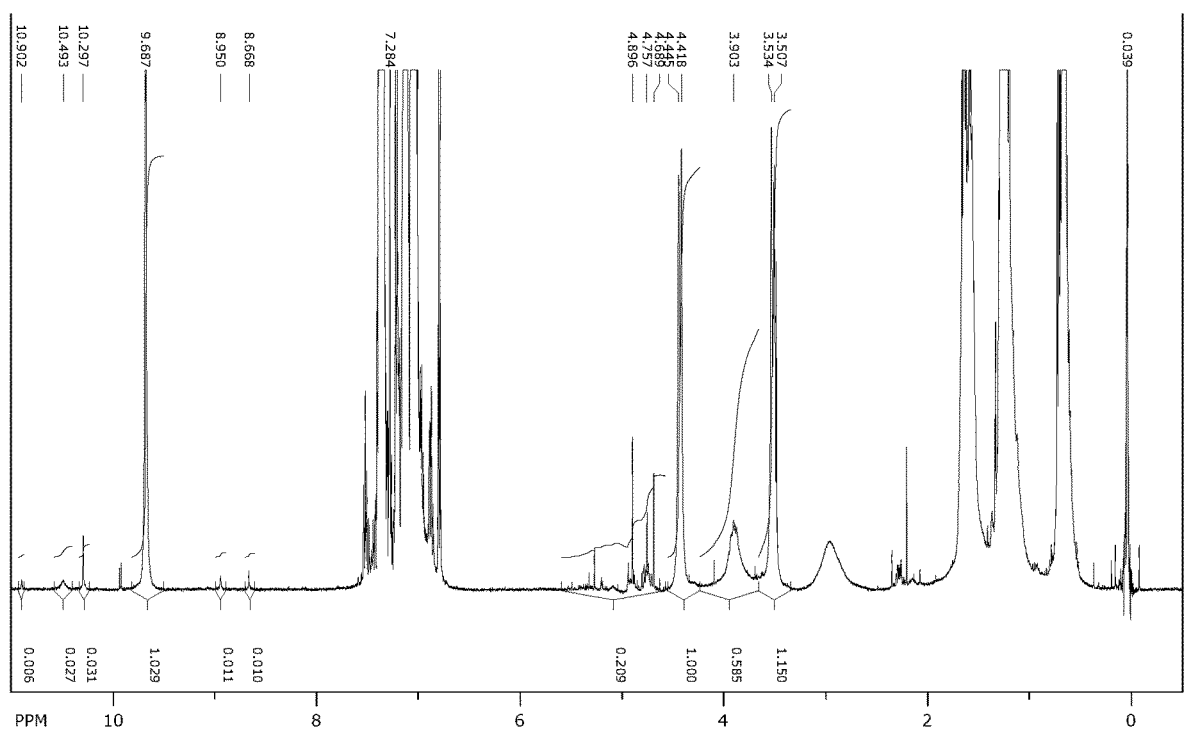

The reaction mass was diluted with 86.3 g more diphenyl ether solvent. The reactor was then heated and the temperature target was set to 145° C. to remove the water, the excess formaldehyde, and methanol. About 2.5 hours after the heating was started, the temperature of the reaction mass reached about 145° C., and a lower layer of 38.1 g was removed. The temperature of the reaction mass was kept at about 145° C. for about 10 hours. The crude reaction mass contained 1.5 wt % PTAP. The GPC and $^1$H-NMR results (solvent $CDCl_3$) for the intermediate tert-amylcalix[8]arene reaction mass are shown in FIG. 1A and FIG. 1B, respectively.

In-Situ Cleavage of Tert-Amylcalix[8]Arene

After cooling to room temperature, 0.82 g NaOH solution (aqueous 50%, 0.01 mol, 10.9 mol % relative to tert-amylcalix[8]arene) was added, and the reaction mass was gradually heated to a temperature of 250-260° C., over the course of about 3 hours, with stirring to avoid caking. The reaction mass became a clear dark liquid, and was kept at about 260° C. for about 3 hours. A sample of the crude reaction mass was taken to measure the $^1$H-NMR and GPC of the formed tert-amylcalix[4]arene, and the heating was turned off.

Figure 1C:
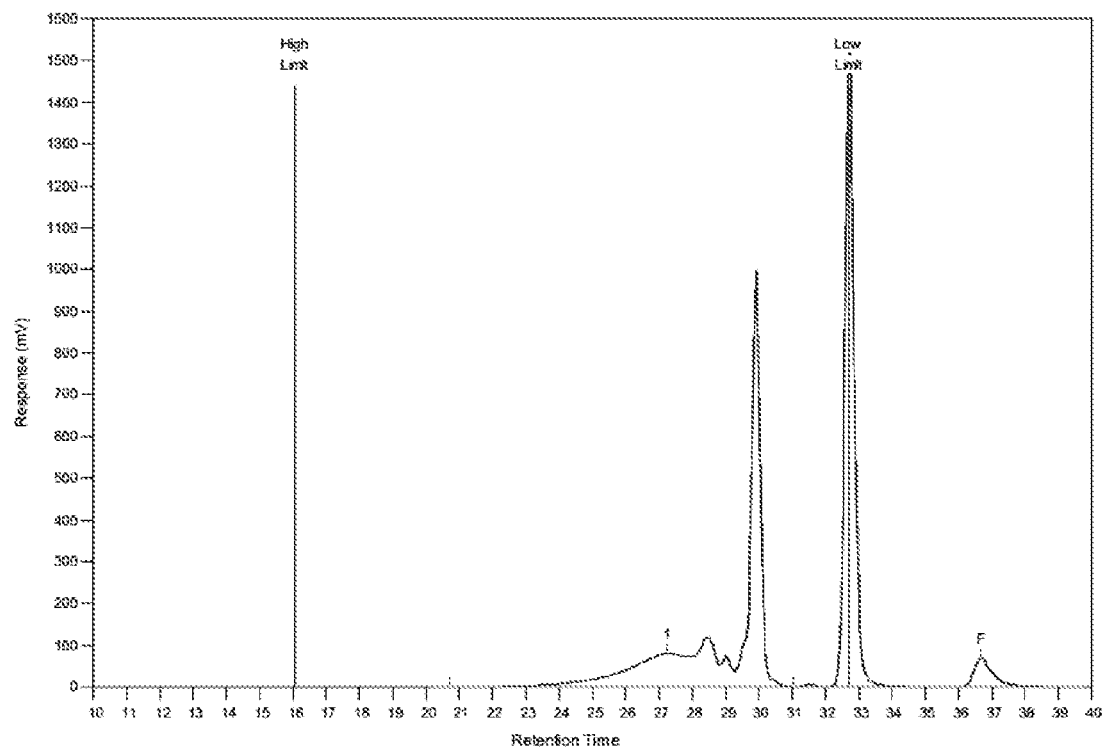
Figure 1D:
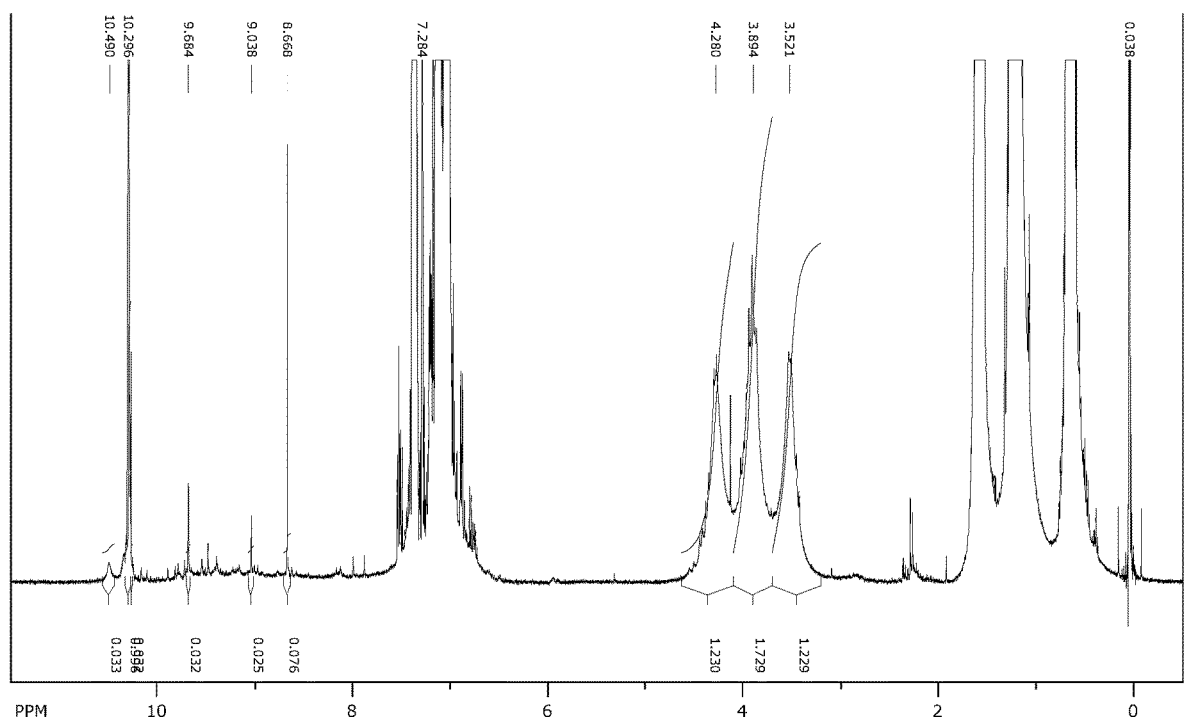

The GPC and $^1$H-NMR results of the crude reaction mass of the formed tert-amylcalix[4]arene are shown in FIG. 1C and FIG. 1D, respectively. It was understood that the $^1$H-NMR does not allow the quantification of the free monomer content; but the GPC results of the final reaction mass display all components in the crude reaction mass (with their respective resonances at the picked wavelength (here 280 nm)).

The crude reaction mass was cooled to room temperature. A 184.1 g ethyl acetate was added, and the precipitated product was filtered through a Büchner funnel, obtaining a 371.6 g mother liquor. It was then washed with a total of 155.6 g ethyl acetate in three portions. After an extended suction, a dry filter cake was obtained. The product contained less than 0.05 wt % free PTAP, 1.3% ethyl acetate, and 2.1% diphenyl ether. The HPLC purity (at 281 nm, does not show solvent or monomer) was 98.0% with 1.2% tert-amylcalix[8]arene. The sodium content was determined to be 146 ppm, which equals to 0.010 g sodium ions or 4.3% of the total sodium ions added as the cleavage catalyst. The theoretical yield was 50.9% in relation to the starting PTAP.

Example 15. One-Pot Synthesis of Tert-Amylcalix[4]Arene from In-Situ Conversion of Tert-Amylcalix[8]Arene (Using TMAOH Catalyst) Using Sodium Hydroxide as the Catalyst-without an Antisolvent
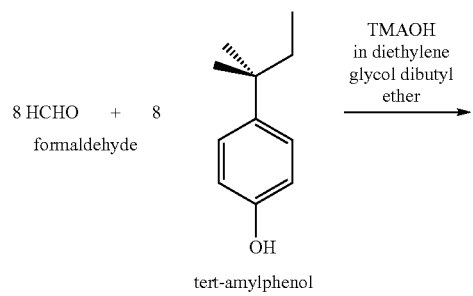
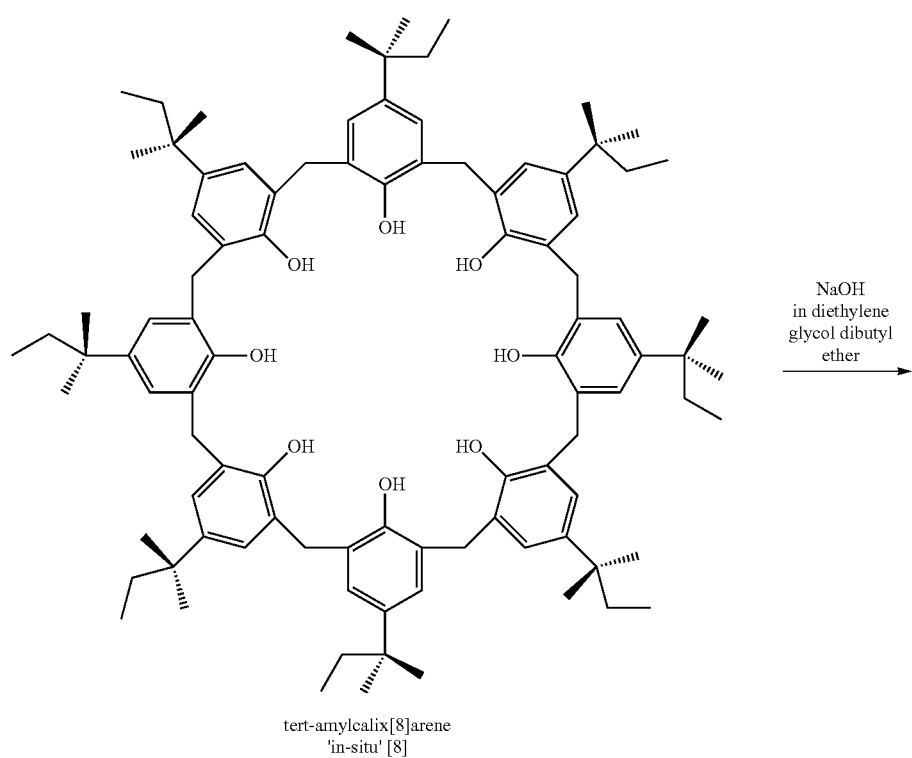

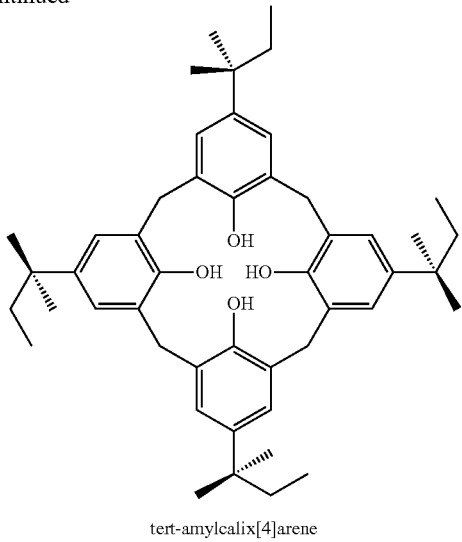

tert-amylcalix[4]arene

Preparation of Tert-Amylcalix[8]Arene

A 500 ml round bottom flask, equipped with an overhead stirrer, thermocouple, overhead addition tank, moisture trap, and condenser, was loaded with 123.2 g PTAP briquettes (0.75 mol) and 100.1 g diethylene glycol dibutyl ether. A gentle nitrogen flow was applied on the surface of the hot reaction mass and the reactor was heated to about 85° C. When all the PTAP and the diethylene glycol dibutyl ether formed a clear solution, 8.2 g of TMAOH solution (25 wt % in methanol, 0.022 mol) was added dropwise over the course of about 17 minutes. At about 88-90° C., a total of 65.8 g of 44.5 wt % aqueous formaldehyde solution (0.98 mol) was added within 39 minutes.

After the formaldehyde addition, the reaction was kept at 90° C. for about 1 hour. The reaction mixture was then heated to reflux at about 100° C. for a total of about 12 hours. At the end of the reflux, the reaction mass was at about 100° C.

Figure 2A:
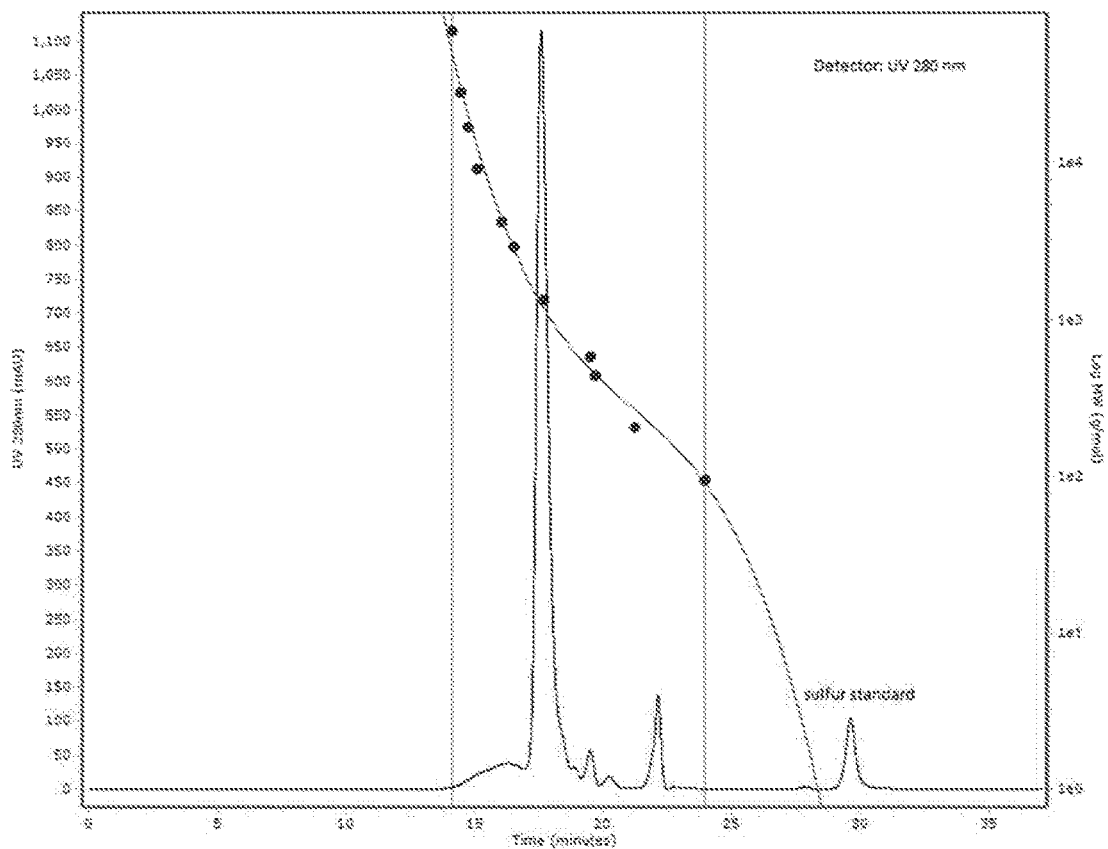
FIG. 2 shows the GPC results (FIG. 2A) and $^1$H-NMR results (FIG. 2B) of the intermediate tert-amylcalix[8]arene reaction mass, and the GPC results (FIG. 2C) and $^1$H-NMR results (FIG. 2D) of the tert-amylcalix[4]arene crude reaction mass prepared from the one-pot, in-situ process illustrated in Example 15.
Figure 2B:
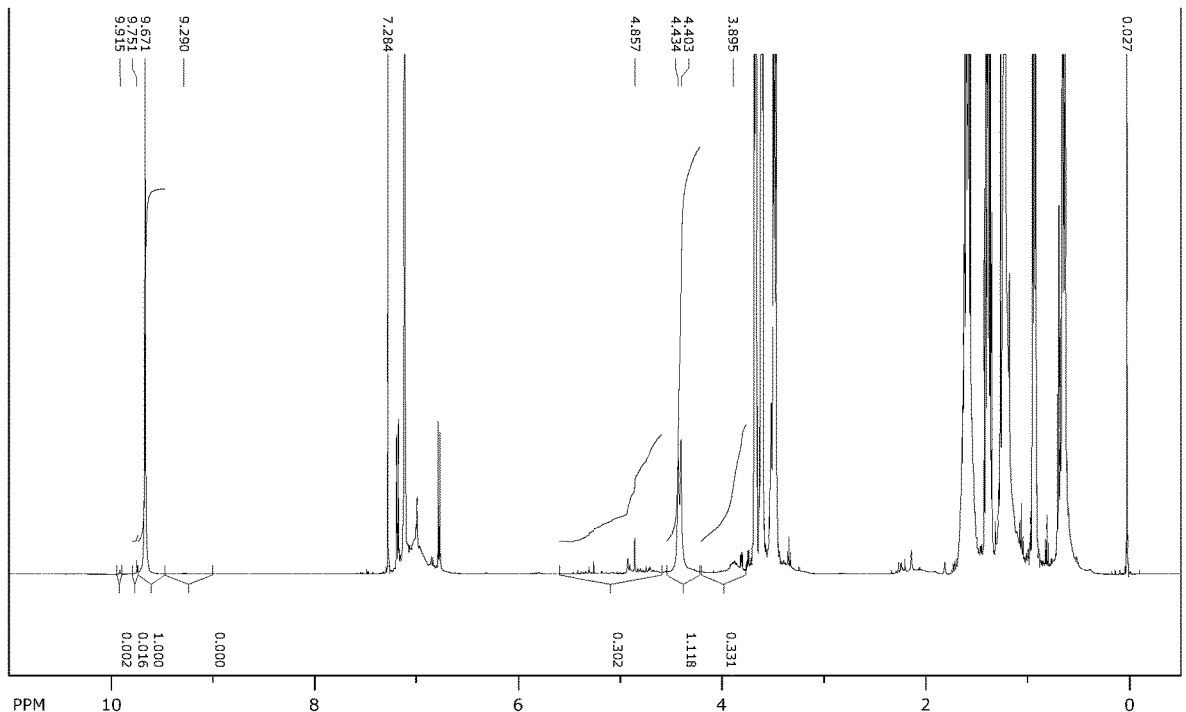

The reaction mass was diluted with 51.2 g more diethylene glycol dibutyl ether solvent. The reactor was then equipped with a Dean-Stark trap and gradually heated with the temperature target set to 143-145° C. to remove the water, the excess formaldehyde, and methanol. About 2.5 hours after the heating was started, the temperature of the reaction mass reached 143-145° C., and was kept at this temperature for a total of about 10 hours until a total of 48.7 g of the lower layer was removed from the Dean-Stark trap, which contained 22.8% formaldehyde (0.37 mol). The crude reaction mass contained 1.9 wt % PTAP. The GPC and $^1$H-NMR results (solvent $CDCl_3$) for the intermediate tert-amylcalix[8]arene reaction mass are shown in FIG. 2A and FIG. 2B, respectively.

In-Situ Cleavage of Tert-Amylcalix[8]Arene

After cooling to about 90° C., 2.4 g NaOH solution (aqueous 50%, 0.03 mol, 32 mol % relative to tert-amylcalix[8]arene) was added, and the reaction mass was gradually heated to a temperature of 250-260° C. over the course of about 2 hours while applying a gentle nitrogen flow to remove the water, with stirring to avoid caking. The reaction mass was kept at about 250-260° C. for about 2 hours. A sample of the crude reaction mass was taken to measure the $^1$H-NMR and GPC of the formed tert-amylcalix[4]arene, and the heating was turned off.

Figure 2C:
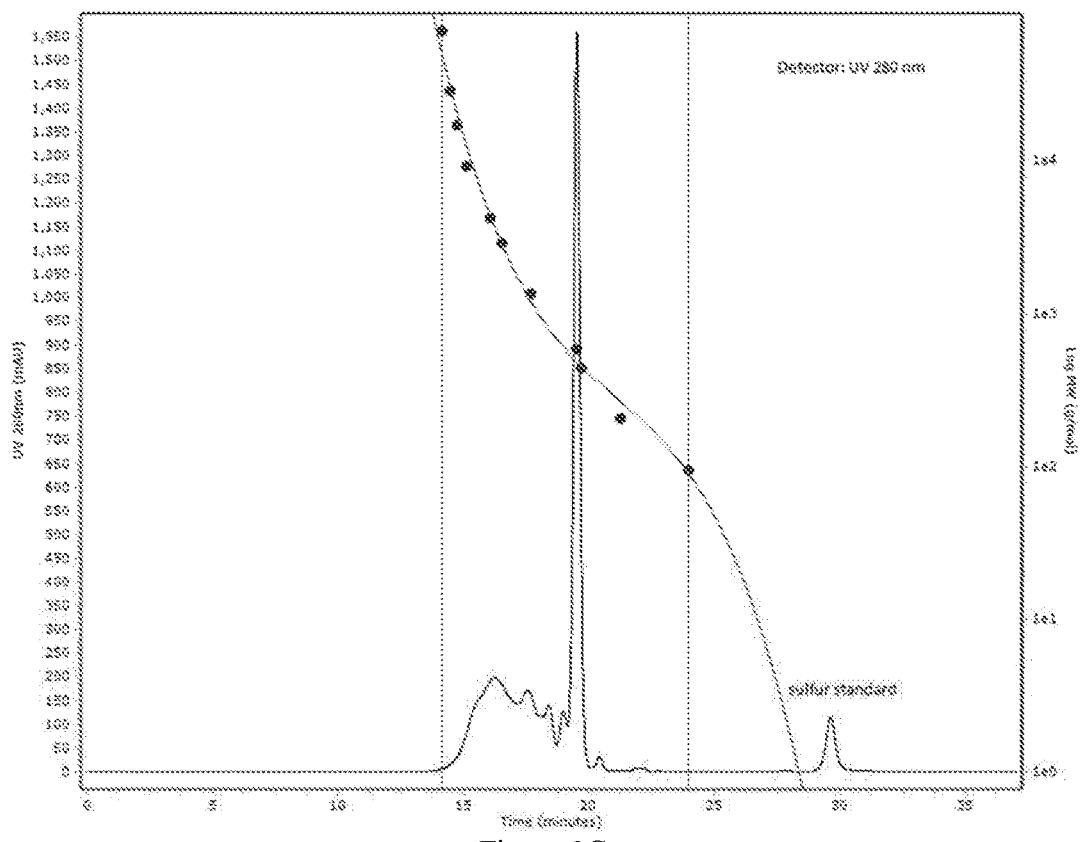
Figure 2D:
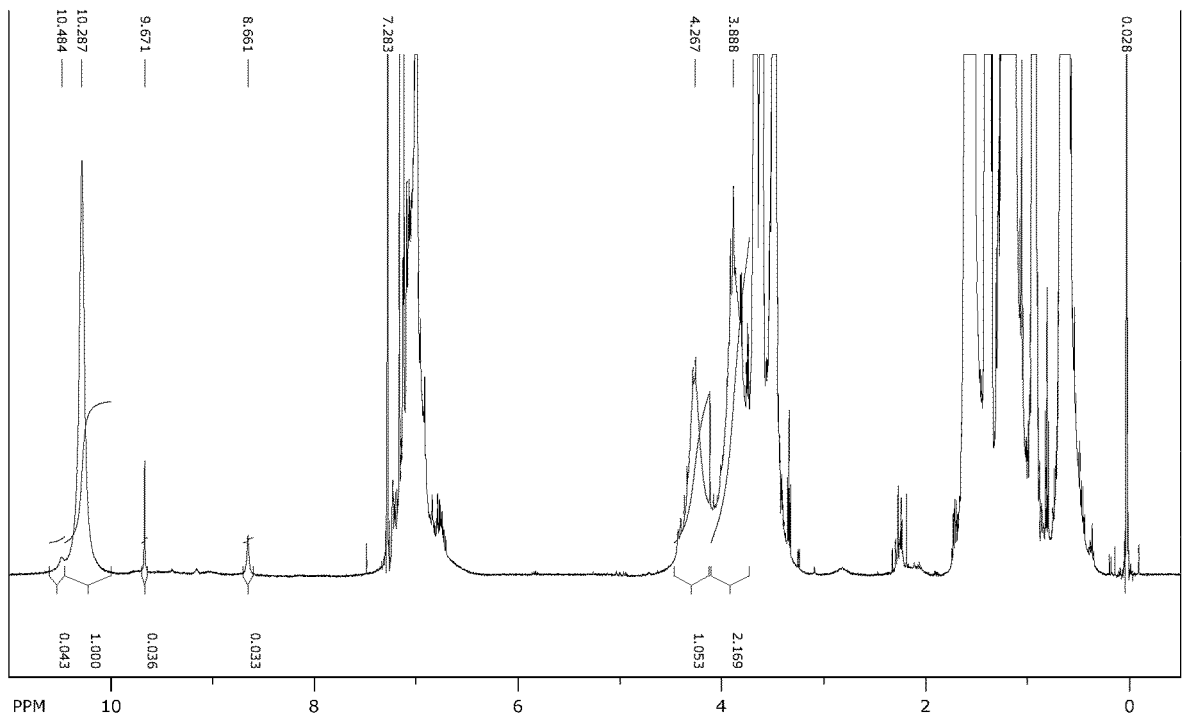

The GPC and $^1$H-NMR results of the crude reaction mass of the formed tert-amylcalix[4]arene are shown in FIG. 2C and FIG. 2D, respectively. It was understood that the $^1$H-NMR does not allow the quantification of the free monomer content; but the GPC results of the final reaction mass display all components in the crude reaction mass (with their respective resonances at the picked wavelength (here 280 nm)).

The crude reaction mass was cooled down to room temperature and the obtained suspension was filtered through a Buchner funnel and washed with a total of 100.7 g ethyl acetate. After drying under vacuum at 130° C., the final product was obtained. The product contained less than 0.05 wt % free PTAP, less than 0.05% ethyl acetate, and 0.31% diethyleneglycol dibutyl ether. The HPLC purity (area % at 281 nm; does not show solvent or monomer) was 96.0% tert-amylcalix[4]arene with 3.3% tert-amylcalix[8] arene. The sodium content was determined to be 843 ppm, which is calculated to be 7.3% of the total sodium ions added as the cleavage catalyst. The theoretical yield was 45.2% in relation to the starting PTAP. The combined mother liquor and wash fluid contained about 2% of the total yield of tert-amyl calix[4]arene.

In this example, no antisolvent was needed to precipitate the high-purity tert-amylcalix[4]arene.

Example 16. Synthesis of Tert-Amylcalix[4]Arene from Tert-Amylcalix[8]Arene Using Sodium Hydroxide as the Catalyst—without an Antisolvent A 250 ml round bottom flask, equipped with an overhead stirrer, thermocouple, and condenser, was loaded with 10.1 g tert-amylcalix[8]arene (0.007 mol) and 80.2 g diethylene glycol dibutylether. 0.097 g NaOH solution (aqueous 50%, 0.001 mol, 17 mol % relative to tert-amylcalix[8]arene) was added. A gentle nitrogen flow was applied over the reaction mass and the reaction mass was heated to a temperature of about 255° C. over the course of 35 minutes. After one hour, the reaction mass formed a clear solution, and was kept at this temperature for about 5 hours. The crude reaction mass was cooled to room temperature and the precipitated solid product was filtered through a Buchner funnel. The residual product in the reactor was rinsed out with a total of 18.1 g diethylene glycol dibutylether.

The obtained filter cake was washed with a total of 36.9 g ethyl acetate and then dried under vacuum. The obtained product had a HPLC-purity of 99.7% (area % at 281 nm; does not show residual solvent), with 0.06% diethylene glycol dibutyl ether and 1.2% ethyl acetate. The overall theoretical yield was 69.6%.

In this example, no antisolvent was needed to precipitate the high-purity tert-amylcalix[4]arene.

Example 17. One-Pot Synthesis of Sec-Butylcalix[4]Arene from In-Situ Conversion of Sec-Butylcalix[8]Arene (Using TMAOH Catalyst) Using Sodium Hydroxide as the Catalyst, with an Antisolvent

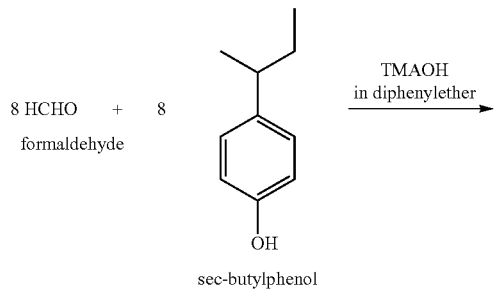

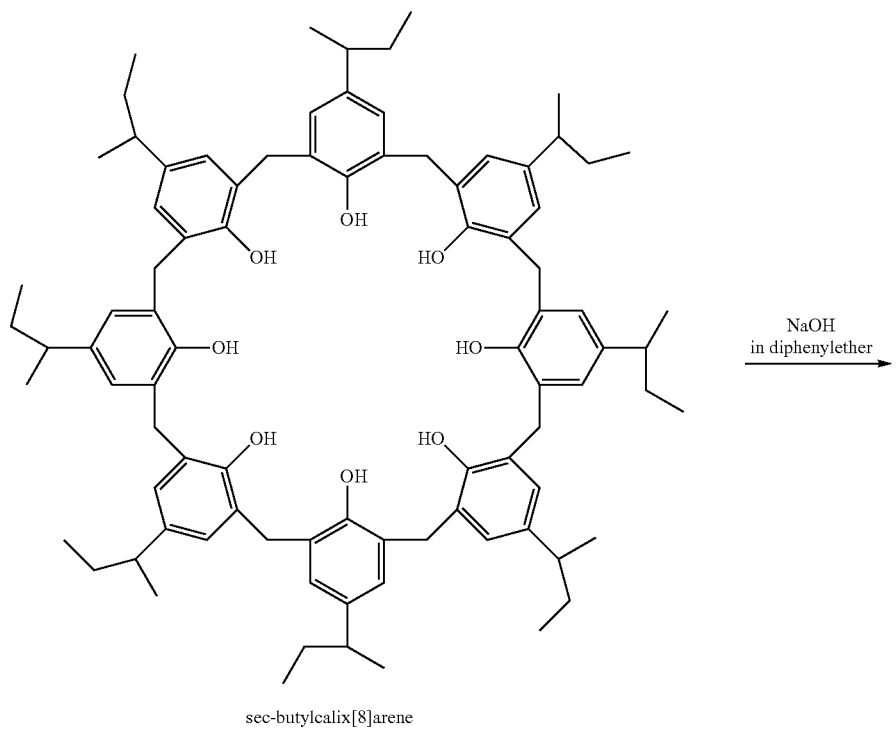

sec-butylcalix[8]arene

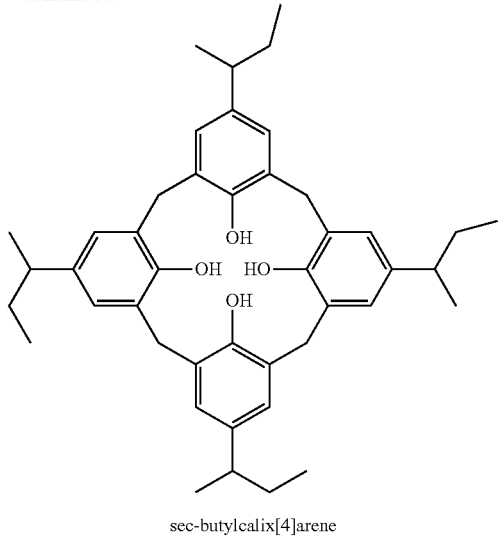

sec-butylcalix[4]arene

Preparation of Sec-Butylcalix[8]Arene

A 500 ml round bottom flask, equipped with an overhead stirrer, thermocouple, overhead addition tank, moisture trap, and condenser, was loaded with 112.7 g para-sec-butylphenol (PSBP) (0.75 mol), 10.1 g xylene and 90.4 g diphenyl ether. A gentle nitrogen flow was applied on the surface of the hot reaction mass and the reactor was heated to about 89° C. When all the PSBP, xylene, and diphenyl ether formed a clear solution, 5.5 g of TMAOH solution (25 wt % in methanol, 0.015 mol) was added dropwise at a temperature of 89° C. over the course of about 3 minutes. At about 90° C., a total of 50.3 g of 49.2 wt % aqueous formaldehyde solution (0.82 mol) was added within 8 minutes.

After the formaldehyde addition, the reaction was kept at 90° C. for about 1 hour. The reaction mixture was then heated to reflux at about 100° C. for a total of about 12 hours. At the end of the reflux, the reaction mass was at about 100° C.

Figure 3A:
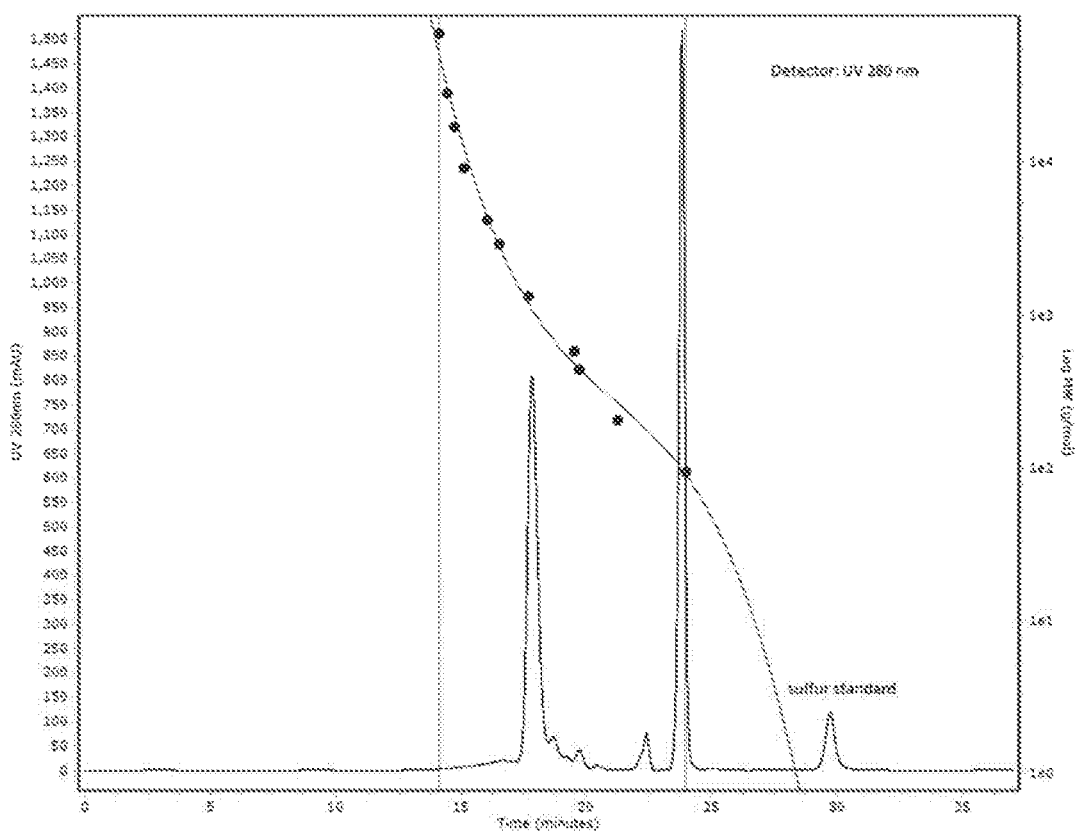
FIG. 3 shows the GPC results (FIG. 3A) and $^1$H-NMR results (FIG. 3B) of the intermediate sec-butylcalix[8]arene reaction mass, and the GPC results (FIG. 3C) and $^1$H-NMR results (FIG. 3D) of the sec-butylcalix[4]arene crude reaction mass prepared from the one-pot, in-situ process illustrated in Example 17.
Figure 3B:
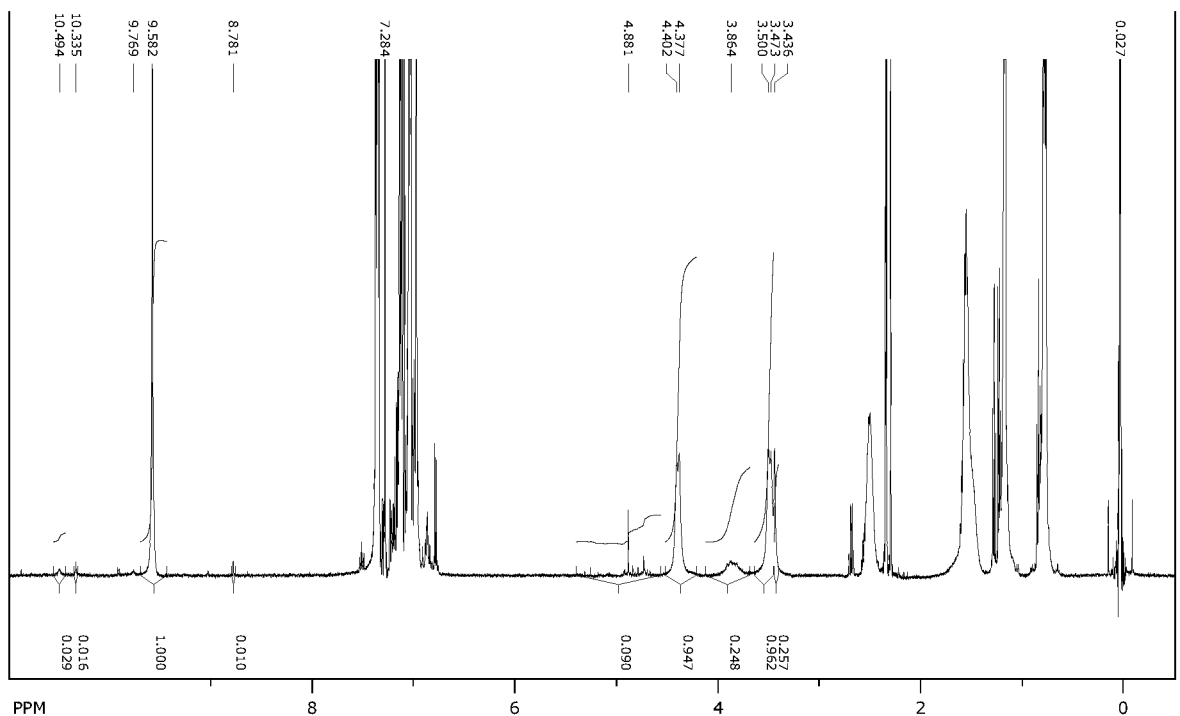

The reaction mass was diluted with 29.9 g xylene and 109.7 g diphenyl ether solvent. The reactor was then heated and the temperature target was set to 145° C. to remove the water, the excess formaldehyde, and methanol. The xylene solvent was added to control the water removal by forming azeotropes and avoiding boilovers. About 2.25 hours after the heating was started, the temperature of the reaction mass reached about 145° C., and was kept at this temperature for a total of about 10 hours until a total of 30.1 g of the lower layer was removed, which contained 7.6% formaldehyde. The crude reaction mass contained 1.46 wt % PSBP. The GPC and $^1$H-NMR results (solvent CDCl$_3$) for the intermediate sec-butylcalix[8]arene reaction mass are shown in FIG. 3A and FIG. 3B, respectively.

In-Situ Cleavage of Sec-Butylcalix[8]Arene

After cooling to about 80° C., 2.4 g NaOH solution (aqueous 50%, 0.03 mol, 32 mol % relative to sec-butylcalix[8]arene) was added, and 41.1 g xylene and 12.4 g ethyl acetate were also added. The additional xylene and ethyl acetate solvents were added to control the water removal to avoid boilovers. The reaction mass was gradually heated to a temperature of 250-260° C. over the course of about 1 hour, with stirring to avoid caking. The reaction mass became a clear dark liquid, and was kept at about 255-260° C. for about 1 hour. A sample of the crude reaction mass was taken to measure the $^1$H-NMR and GPC of the formed sec-butylcalix[4]arene, and the heating was turned off.

Figure 3C:
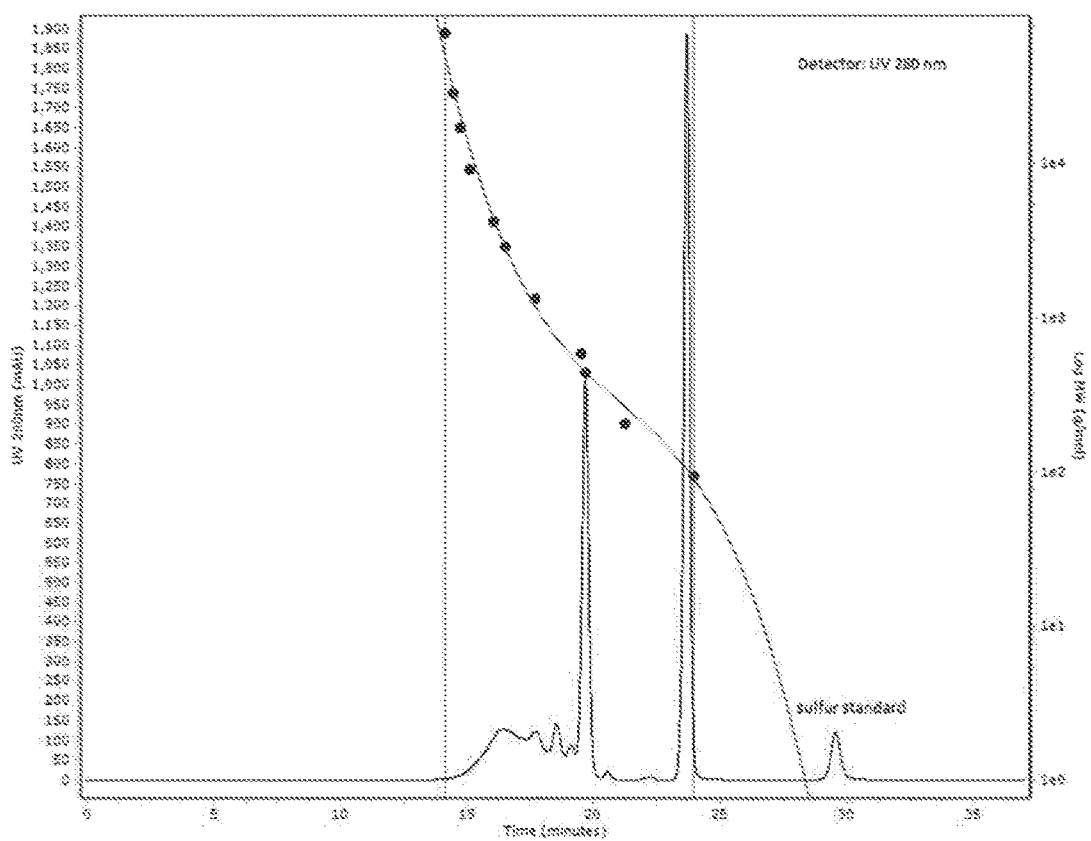
Figure 3D:
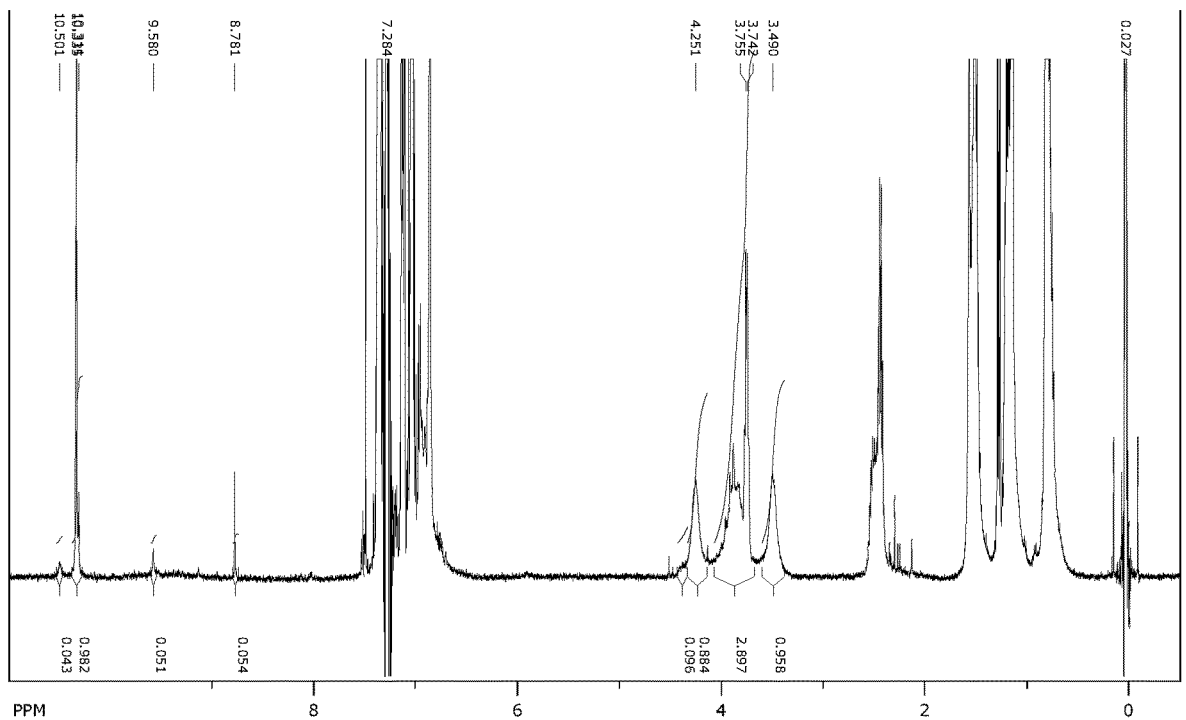

The GPC and $^1$H-NMR results of the crude reaction mass of the formed sec-butylcalix[4]arene are shown in FIG. 3C and FIG. 3D, respectively. It was understood that the $^1$H-NMR does not allow the quantification of the free monomer content; but the GPC results of the final reaction mass display all components in the crude reaction mass (with their respective resonances at the picked wavelength (here 280 nm)).

Isolation of Sec-Butylcalix[8]Arene

Because the obtained sec-butylcalix[4]arene was very soluble in standard solvents, such as the reaction solvent diphenyl ether used in this example, the following procedures were developed to isolate sec-butylcalix[4]arene, based on its relatively poorer solubility in acetone (~1.0% at room temperature).

The sodium hydroxide catalyst in the crude reaction mass was neutralized by the addition of 3.0 g 37% aqueous HCl (0.03 mol). 22.6 g ethyl acetate and 22.1 g xylene were added, to prevent boilovers with the water from the aqueous HCl. A distillation was started to reduce the diphenyl ether content in the reaction mass, under a reduced pressure (28 Torr) and a temperature of about 215° C.

The reaction mass was then cooled down to room temperature and a total of 101.4 g acetone was added, causing the product to solidify during the cooling phase. Acetone helped to dissolve the linear resins (which was facilitated by heating to reflux), but did not dissolve the main calixarene product. When all the linear resins were dissolved, it was cooled to room temperature and the less soluble calix[4]arene and calix[8]arene products remained as solids. The obtained suspension was filtered through a Büchner funnel and washed with a total of 102 g acetone. The filter cake after drying (at 130° C. under vacuum) weighed 42.2 g. The HPLC purity was 94.6% sec-butylcalix[4]arene with 4.7% sec-butylcalix[8]arene. The theoretical yield on dry base was 33.8% in relation to starting PSBP.

The 106.4 g of mother liquor still contained 5.6 wt % sec-butylcalix[4]arene, which equals to 6.0 g or 4.9% of the theoretical yield.

The crude sec-butylcalix[4]arene can be further purified by dissolving the filter cake in boiling acetone (whereas the sec-butylcalix[8]arene stays undissolved) and then by hot filtration. After crystallization of the filtrate, a product with a purity of greater than 97% sec-butylcalix[4]arene and less than 1% sec-butylcalix[8]arene was obtained from this crude product.

Figure 4:
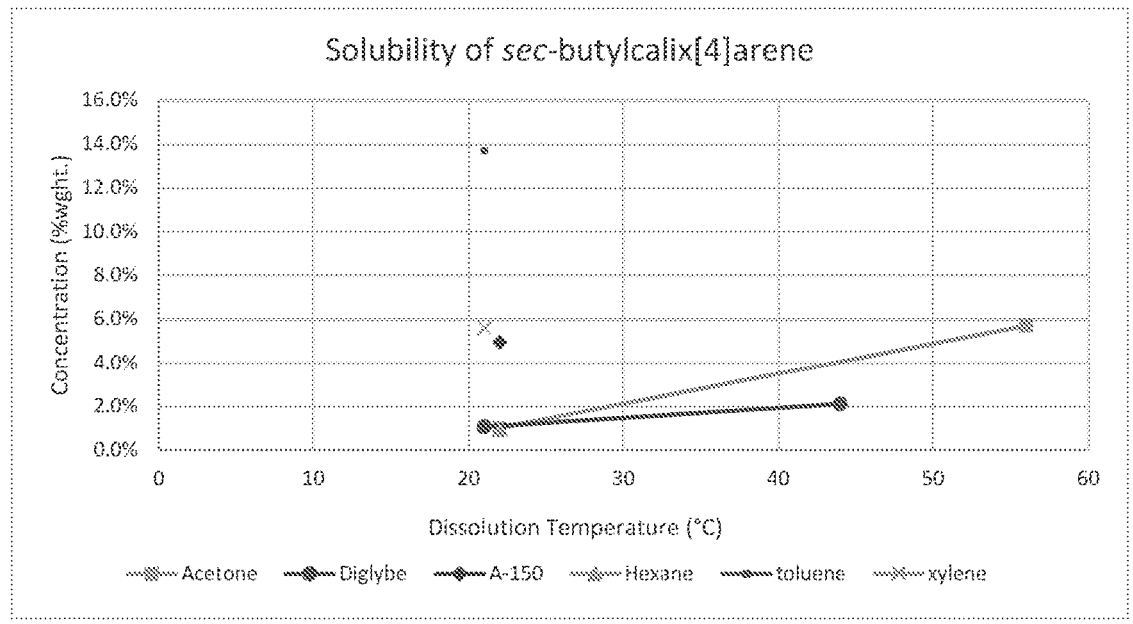
FIG. 4 shows the solubility of sec-butylcalix[4]arene in various organic solvents, at various dissolution temperatures. "Diglybe" refers to diethylene glycol dibutyl ether.

The solubility (concentration) of sec-butylcalix[4]arene in various organic solvents, at various dissolution temperatures were evaluated and the results are shown in FIG. 4. The solubility (concentration) of sec-butylcalix[4]arene in various organic solvents, such as diethylene glycol dibutyl ether and A-150 solvent, at various dissolution temperatures were compared against the solubility of tert-butylcalix[4]arene in the same solvent at the same dissolution temperature. The results are shown in FIG. 5.

Example 18. One-Pot Synthesis of Tert-Octylcalix[4]Arenes from In-Situ Conversion of Tert-Octylcalix[8]Arenes (Using TEAOH Catalyst) Using Sodium Hydroxide as the Catalyst, without an Antisolvent

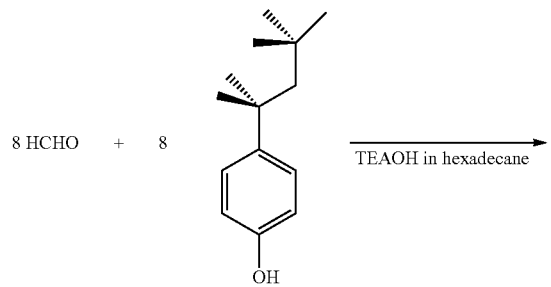

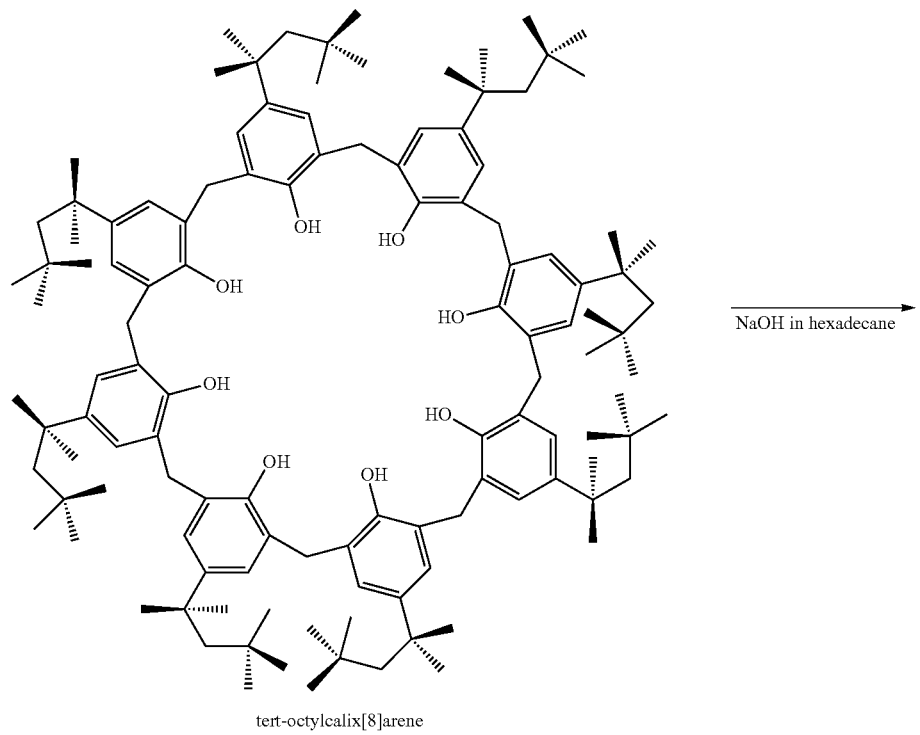

tert-octylcalix[8]arene

-continued

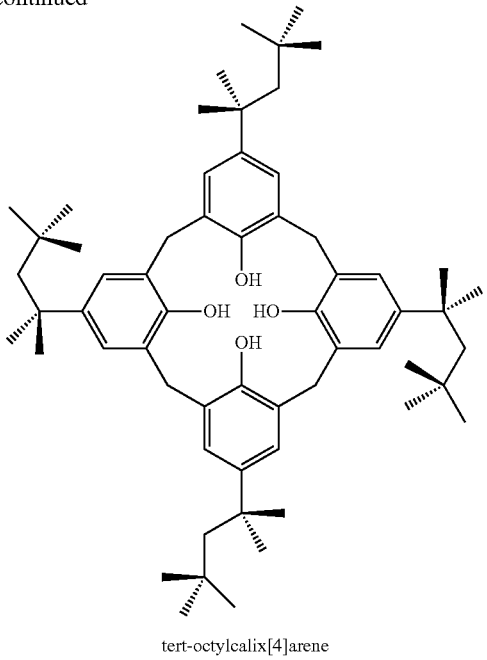

tert-octylcalix[4]arene

Preparation of Tert-Octylcalix[8]Arene

A 500 ml round bottom flask, equipped with an overhead stirrer, thermocouple, overhead addition tank, moisture trap, and condenser, was loaded with 154.7 g para-tert octylphenol (PTOP) briquettes (0.75 mol) and 100.0 g hexadecane. A gentle nitrogen flow was applied on the surface of the reaction mass and the reactor was heated to about 105° C. When all the PTOP and the hexadecane formed a clear solution, 5.5 g of TEAOH solution (40 wt % in water, 0.015 mol) was added dropwise at about 90° C. over the course of about 8 minutes. At about 91° C., a total of 54.6 g of 47.4 wt % aqueous formaldehyde solution (0.86 mol) was added within 44 minutes.

After the formaldehyde addition, the reaction was kept at 90° C. for about 1 hour. The reaction mixture was then heated to reflux at about 100° C. for a total of about 12 hours. At the end of the reflux, the reaction mass was at about 103° C.

Figure 6A:
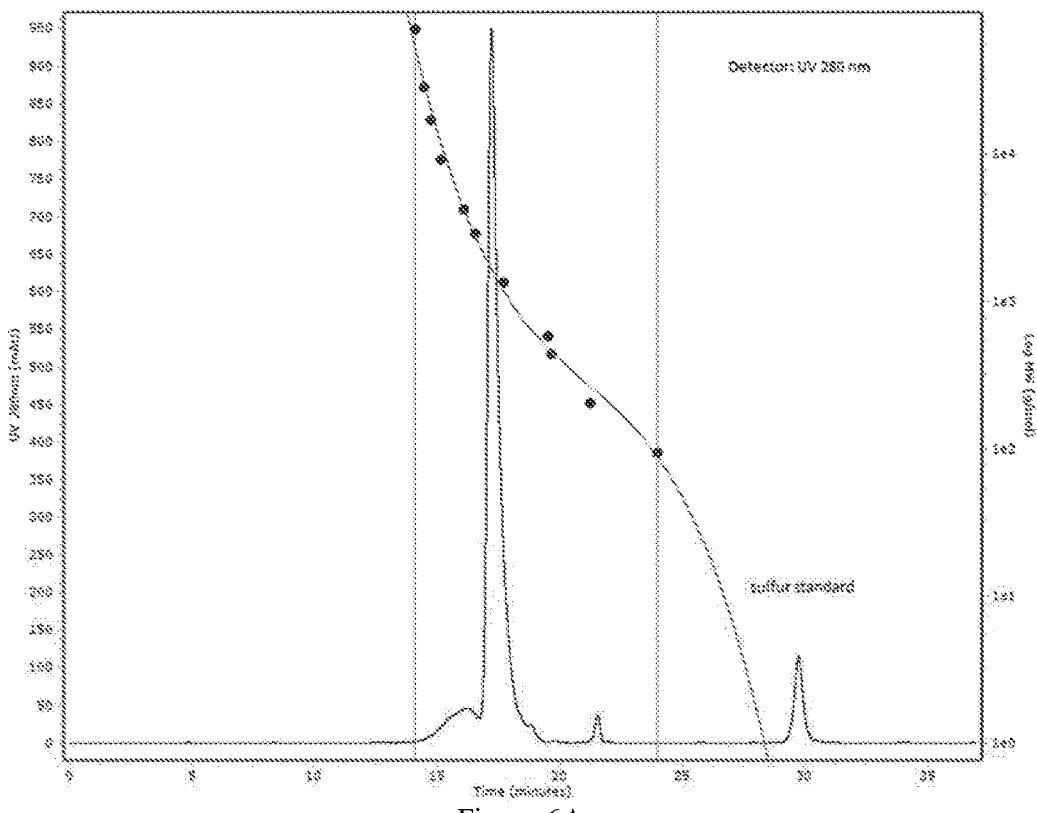
FIG. 6 shows the GPC result (FIG. 6A) and $^1$H-NMR result (FIG. 6B) of the intermediate tert-octylcalix[8]arene reaction mass, and the GPC result (FIG. 6C) and $^1$H-NMR result (FIG. 6D) of the tert-octylcalix[4]arene crude reaction mass prepared from the one-pot, in-situ process illustrated in Example 18.
Figure 6B:
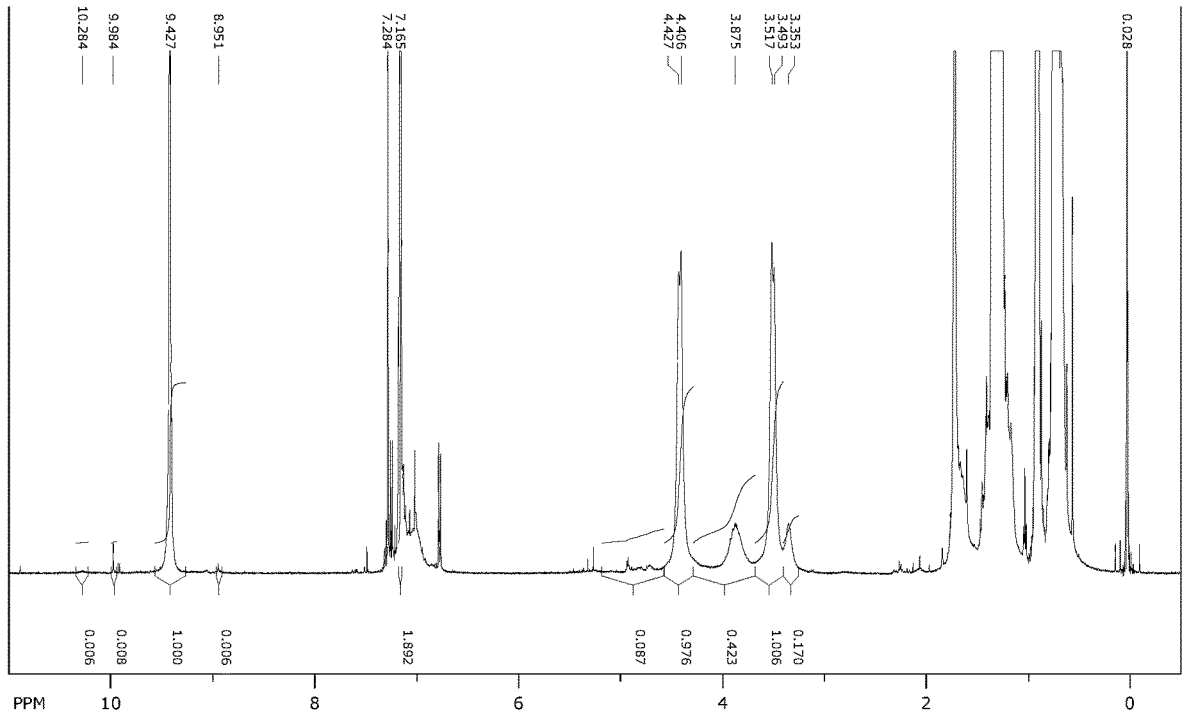

The reaction mass was diluted with 50.3 g more hexadecane solvent. The reactor was then heated and the temperature target was set to 145° C. to remove the water and excess formaldehyde, with the nitrogen stream over the surface of the reaction mass to facilitate further water removal. About 71 minutes after the heating was started, the temperature of the reaction mass reached about 145° C. When the reaction mass became foamy, the foaming was mitigated by heating the reaction vessel with a heat gun. The temperature of the reaction mass was kept at about 145° C. for about 10 hours until a lower layer of 39.6 g was removed. This aqueous distillate lower layer contained 6.8% formaldehyde. The crude product tert-octylcalix[8]arene was obtained with an HPLC purity of 82.0% (area % at 281 nm) and 0.9 wt % PTOP. The GPC and $^1$H-NMR results (solvent CDCl$_3$) for the intermediate tert-octylcalix[8]arene reaction mass are shown in FIG. 6A and FIG. 6B, respectively.

In-Situ Cleavage of Tert-Octylcalix[8]Arene

Figure 6C:
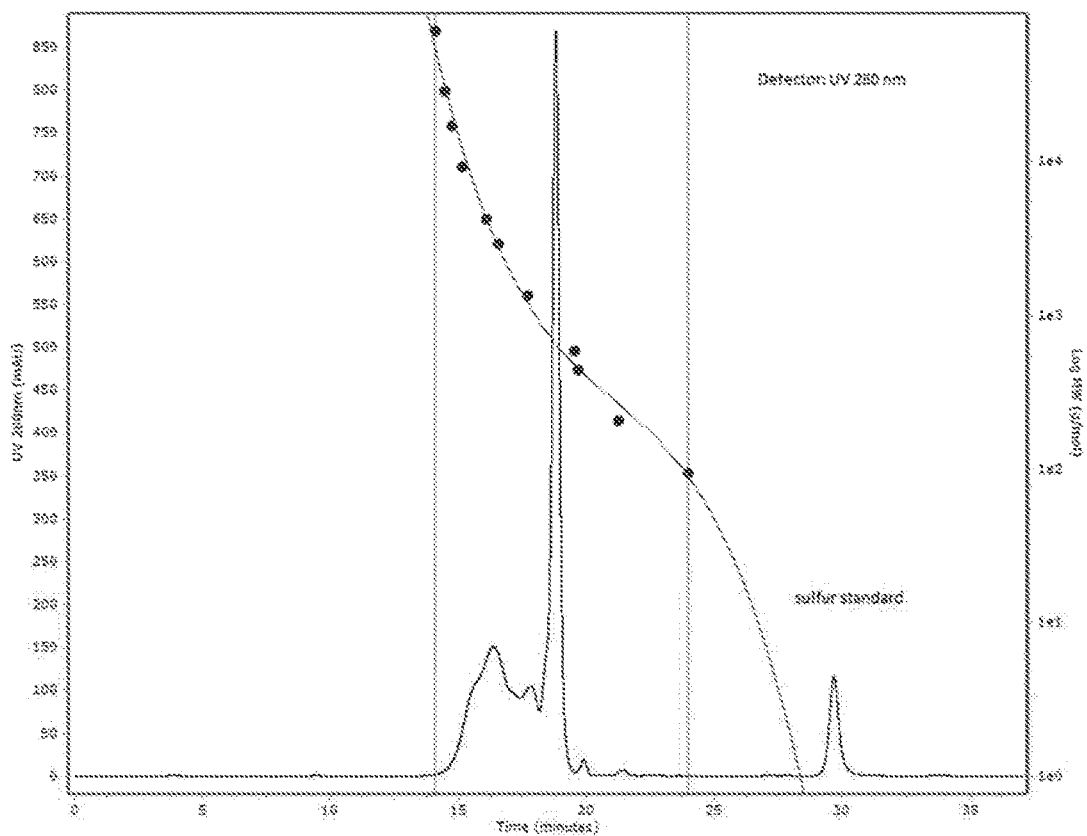
Figure 6D:
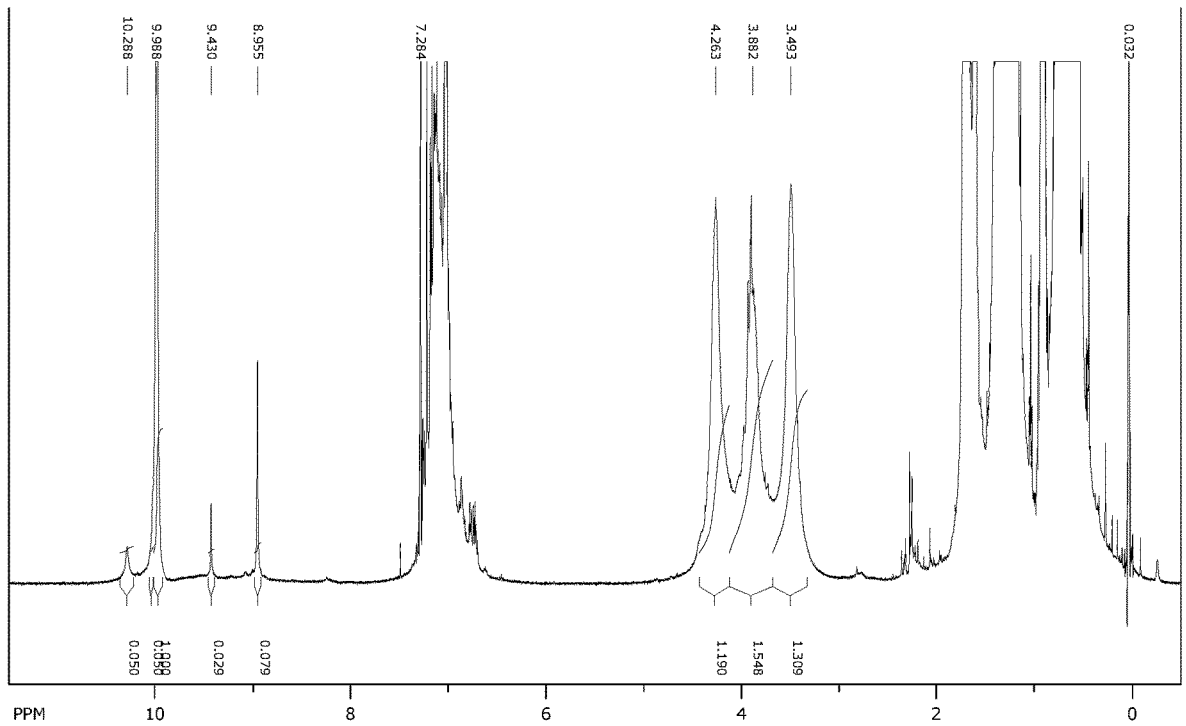

After cooling to room temperature, 1.2 g NaOH solution (aqueous 50%, 0.015 mol, 2.0 mol % relative to the starting PTOP) was added, and the reaction mass was gradually heated to a temperature of 250-260° C. over the course of about 30 minutes, with stirring to avoid caking. The reaction mass became a clear dark liquid. The reaction mass was kept at about 250-260° C. for about 4 hours. A sample of the crude reaction mass was taken to measure the $^1$H-NMR and GPC of the formed tert-amylcalix[4]arene, and the heat was turned off. The GPC and $^1$H-NMR results of the crude reaction mass of the formed tert-amylcalix[4]arene are shown in FIG. 6C and FIG. 6D, respectively.

The crude reaction mass was cooled down to room temperature and the obtained suspension was filtered through a Büchner funnel and washed in portions with a total of 102.4 g isopropanol. After drying under vacuum at 130° C., the final product was obtained. The product contained about 0.05 wt % free PTOP, less than 0.05% isopropanol, and 0.4% hexadecane. The HPLC purity (area % at 281 nm; does not show solvent or monomer) was 96.7% tert-octylcalix[4]arene. The theoretical yield was 43.2% in relation to the starting PTOP.

In this example, no antisolvent was needed to precipitate the high-purity tert-amylcalix[4]arene.

Example 19. One-Pot Synthesis of Tert-Amylcalix[4]Arenes from In-Situ Conversion of Tert-Amylcalix[8]Arenes (Using TMAOH Catalyst and Paraformaldehyde) Using Sodium Hydroxide as the Catalyst, without an Antisolvent Preparation of Tert-Amylcalix[8]Arene A 500 ml round bottom flask, equipped with an overhead stirrer, thermocouple, overhead addition tank, moisture trap, and condenser, was loaded with 123.2 g para-tert-amylphenol (PTAP) briquettes (0.75 mol), 27.0 g paraformaldehyde (95%, 0.85 mol), and 88.5 g diphenylether. A gentle nitrogen flow was applied on the surface of the reaction mass and while the reactor was heated to about 84-106° C., 5.5 g of TMAOH solution (25 wt % in methanol, 0.015 mol) was added dropwise over the course of about 4 minutes.

The reaction mixture was then further heated with the temperature target set to 145° C. to remove the water through the moisture trap, with the gentle nitrogen flow assisting in transporting the water to the trap. The temperature of the reaction mass reached about 143° C. within 26 minutes, and was kept for about 5 hours between 143-154° C. The 18.5 g aqueous distillate removed contained 2.3 g formaldehyde (which corresponds to 9.1% of the starting formaldehyde).

Figure 7A:
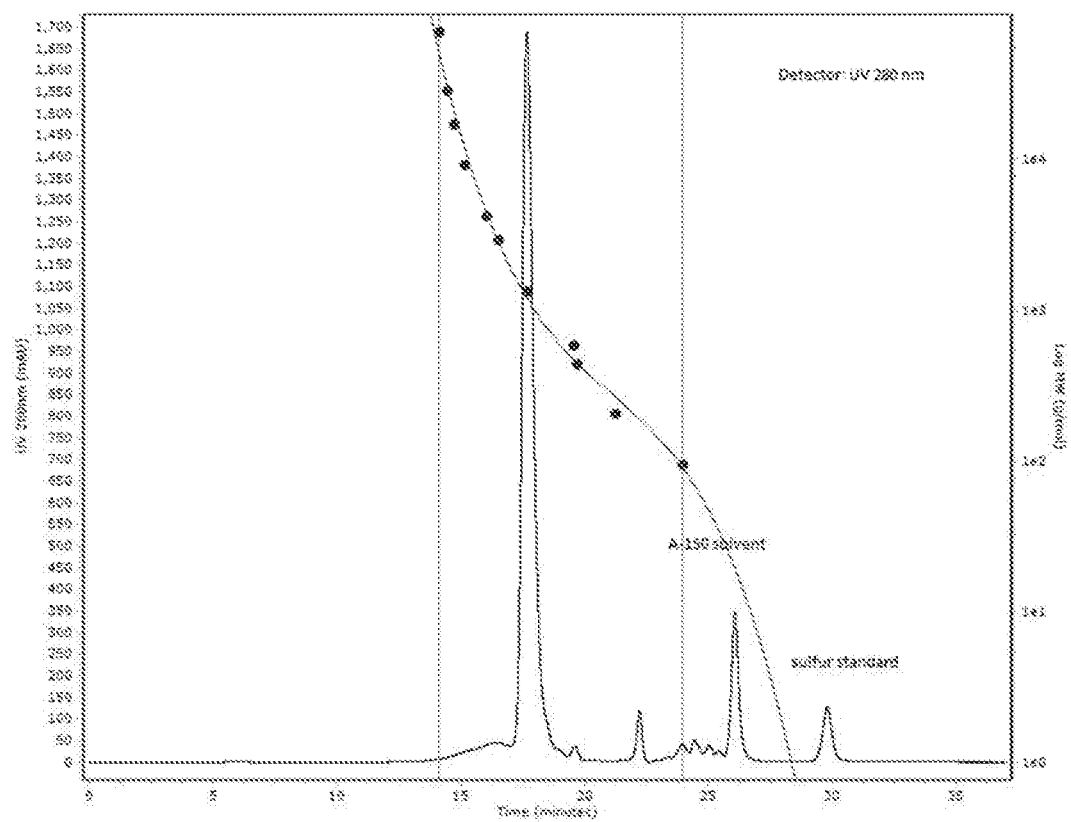
FIG. 7 shows the GPC result (FIG. 7A) of the intermediate tert-amylcalix[8]arene reaction mass, and the GPC result (FIG. 7B) of the tert-amylcalix[4]arene crude reaction mass prepared from the one-pot, in-situ process illustrated in Example 19.

The crude product tert-amylcalix[8]arene was obtained with an HPLC purity of 83.2% (area % at 281 nm) and 1.12 wt % PTAP (which corresponds to 2.0% of the starting PTAP). The GPC result for the intermediate tert-amylcalix[8]arene reaction mass is shown in FIG. 7A.

In-Situ Cleavage of Tert-Amylcalix[8]Arene

Figure 7B:
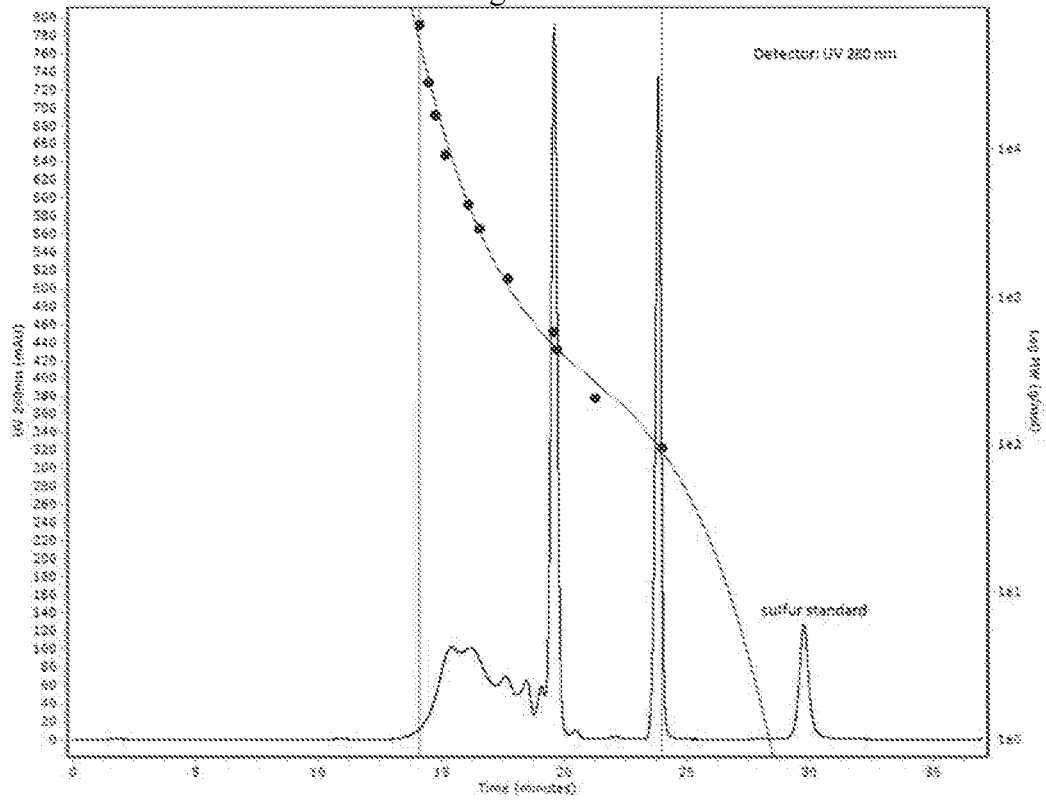

After cooling to 72° C., 1.2 g NaOH solution (aqueous 50%, 0.015 mol, 16.0 mol % relative to tert-amylcalix[8]arene assuming all PTAP converted to calix[8]arenes) was added, and the reaction mass was gradually heated to a temperature of 250-260° C. over the course of about 22 minutes, with stirring to avoid caking. The reaction mass became a clear yellow liquid. The reaction mass was kept at about 260° C. for about 3 hours. A sample of the crude reaction mass was taken to measure and GPC of the formed tert-amylcalix[4]arene, and the heating was turned off. The GPC result of the crude reaction mass of the formed tert-amylcalix[4]arene is shown in FIG. 7B.

The crude reaction mass was cooled down to room temperature, diluted with 139.4 g isopropanol and the obtained suspension was filtered through a Büchner funnel and washed in portions with a total of 209.4 g isopropanol. The final product contained less than 0.05 wt % free PTAP, less than 0.05% isopropanol, and 0.11% diphenylether. The HPLC purity (area % at 281 nm; does not show solvent or monomer) was 96.0% tert-amylcalix[4]arene with 3.1% tert-amylcalix[8]arene. The theoretical yield was 39.6% in relation to the starting PTAP.

In this example, no antisolvent was needed to precipitate the high-purity tert-amylcalix[4]arene.

Sample Characterization Methods.

The reaction products in above examples were characterized by various methods, including ¹H-NMR, GPC, and HPLC.

¹H-NMR spectra was recorded at 500 MHz frequency in δ (ppm) using CDCl₃ as internal standard.

Gel permeation chromatography (GPC) was conducted with a three-column set PLGel 5 μm (500 Å, 100 Å, 50 Å) (column temperature of 40° C.) with the 99/1 THF/MeOH as the mobile phase and the flow rate at 1.0 mL/minute, equipped with a UV detector at 280 nm. The sample concentration was 2.5 mg/mL with 50 μL injection volume.

High-Performance Liquid Chromatography (HPLC) was performed on a Hewlett Packard 1100 Series HPLC System using Agilent InfinityLab Poroshell 120 EC-C18 HPLC columns 3.0×150 mm, 2.7 μm (Agilent Technologies) and a UV detector set at 281 nm. HPLC grade solvents were used. Samples were dissolved in stabilized chloroform (in ethanol or alkane). To obtain a high peak resolution for calixarene compounds with varying ring sizes, particularly from ring size 4 to ring size 8, the following combinations of solvents, gradients, and flow rates were used:

| Flow rate: | 0.4 ml/minute | | |
|---|---|---|---|
| Gradient: | Time (min) | % C | % D |
| | 0 | 90 | 10 |
| | 5 | 90 | 10 |
| | 20 | 80 | 20 |
| | 30 | 40 | 60 |
| | 35 | 20 | 80 |
| | 40 | 20 | 80 |
| | 42 | 90 | 10 |

C = 99/1 acetonitrile/glacial acetic acid;
D = 12:9:1 MeCl₂:MTBE (methyl tert butyl ether):glacial acetic acid

We claim:

1. A process for a one-pot synthesis of a high-purity calix[4]arene compound, comprising:
   reacting a phenolic compound and an aldehyde in the presence of at least one nitrogen-containing base as a catalyst to form a calix[8]arene compound; and
   cleaving the calix[8]arene compound into a high-purity calix[4]arene compound, directly, without carrying out a purification step before the cleaving step.

2. The process of claim 1, wherein the phenolic compound is phenol, an alkyl phenol, or an arylalkyl phenol.

3. The process of claim 1, wherein the phenolic compound is a para-tert-butyl phenol, para-tert-amyl phenol, para-tert-octyl phenol, para-benzyl phenol, or para-cumylphenol.

4. The process of claim 1, wherein the aldehyde is formaldehyde or paraformaldehyde.

5. The process of claim 1, wherein the process is carried out in the absence of a recrystallization step.

6. The process of claim 1, wherein the reacting step is carried out in the presence of an organic solvent.

7. The process of claim 6, wherein the organic solvent is an aromatic hydrocarbon, a straight-chain hydrocarbon having 11 to 20 carbon atoms, an ether, or a mixture containing thereof.

8. The process of claim 6, wherein the step of cleaving comprises:
   heating the calix[8]arene compound to a temperature of at least about 200° C., in the presence of a metal hydroxide catalyst.

9. The process of claim 8, wherein the step of cleaving comprises:
   heating the calix[8]arene compound at a temperature ranging from about 250 to about 260° C., in the presence of an alkali metal hydroxide catalyst, for a period of 30 minutes or longer.

10. The process of claim 8, further comprises:
    lowering the temperature to precipitate the high-purity calix[4]arene compound.

11. A process for a one-pot synthesis of a high-purity calix[4]arene compound, comprising:
    reacting a phenolic compound and an aldehyde in the presence of at least one nitrogen-containing base as a catalyst, in an organic solvent, to form a calix[8]arene compound;
    cleaving the calix[8]arene compound into a high-purity calix[4]arene compound, directly, without carrying out a purification step before the cleaving step; and
    adding an antisolvent to precipitate the calix[4]arene compound having a purity of at least 95%.

12. The process of claim 11, wherein the antisolvent is an ester, ketone, alcohol, or acetonitrile.

13. The process of claim 1, wherein the high-purity calix[4]arene compound comprises 4 units of formula (A-1):

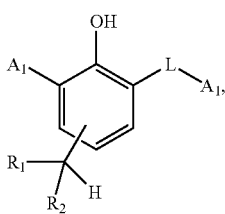

(A-1)

wherein:
each of $R_1$ and $R_2$ is independently linear, branched, or cyclic $C_1$-$C_{30}$ alkyl, aryl, alkylaryl, or arylalkyl;
each L is independently selected from the group consisting of —$CH_2$—, —C(O)—, —CH($R_3$)—, —($CH_2$)$_{n'}$—O—($CH_2$)$_{n'}$—, —C($R_3$)$_2$—;
each $R_3$ is independently a $C_1$-$C_6$ alkyl;
each n' is independently an integer from 1-2; and
each $A_1$ represents a direct covalent bond to an adjacent unit of formula (A-1) such that there is one L group between adjacent units, whereby the total units in the calixarene compound form a ring.

14. The process of claim 13, wherein each $R_1$ is methyl, and each $R_2$ is methyl, ethyl, propyl, or hexyl.

15. The process of claim 13, wherein the calix[4]arene compound is at least partially soluble in a hydrocarbon solvent at room temperature.

16. The process of claim 15, wherein the solubility of the calix[4]arene compound in toluene is at least 5 wt % at about 21° C.

17. The process of claim 13, wherein the reacting step is carried out in the presence of an organic solvent, and wherein the process further comprises:
adding an antisolvent to precipitate the calix[4]arene compound having a purity of at least 94%.

18. The process of claim 17, wherein the antisolvent is acetone or isopropanol.

19. The process of claim 17, further comprising, prior to adding the antisolvent:
neutralizing the metal hydroxide catalyst by adding an acid; and
removing, at least partially, the organic solvent by distillation.

20. A process for improved conversion of a calix[8]arene compound to a calix[4]arene compound, comprising:
providing a calix[8]arene compound; and
cleaving the calix[8]arene compound in a glycol ether solvent having a boiling point of at least about 200° C., to result in a high-purity calix[4]arene compound, without using an antisolvent.

21. The process of claim 20, wherein the glycol ether solvent has a boiling point ranging from about 250 to about 260° C.

22. The process of claim 21, wherein the glycol ether solvent is diethylene glycol dibutyl ether.

23. The process of claim 20, wherein the step of cleaving comprises:
heating the calix[8]arene compound at a temperature of at least about 200° C., in the presence of a metal hydroxide catalyst.

24. The process of claim 23, wherein the step of cleaving comprises:
heating the calix[8]arene compound at a temperature ranging from about 250 to about 260° C., in the presence of an alkali metal hydroxide catalyst, for a period of about 30 minutes or longer; and
lowering the temperature to precipitate the calix[4]arene compound having a purity of at least 98%.

25. The process of claim 20, wherein the calix[8]arene compound comprises 8 units of formula (A-1):

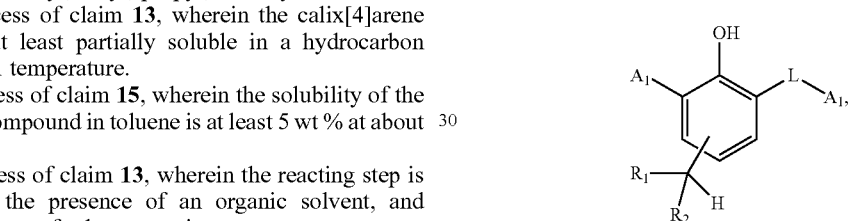

(A-1)

wherein:
each of $R_1$ and $R_2$ is independently linear, branched, or cyclic $C_1$-$C_{30}$ alkyl, aryl, alkylaryl, or arylalkyl;
each L is independently selected from the group consisting of —$CH_2$—, —C(O)—, —CH($R_3$)—, —($CH_2$)$_{n'}$—O—($CH_2$)$_{n'}$—, —C($R_3$)$_2$—;
each $R_3$ is independently a $C_1$-$C_6$ alkyl;
each n' is independently an integer from 1-2; and
each $A_1$ represents a direct covalent bond to an adjacent unit of formula (A-1) such that there is one L group between adjacent units, whereby the total units in the calixarene compound form a ring.

* * * * *